US012648530B2

(12) United States Patent
Puglisi et al.

(10) Patent No.: US 12,648,530 B2
(45) Date of Patent: Jun. 9, 2026

(54) PARTHENOCARPIC WATERMELON PLANTS

(71) Applicant: NUNHEMS B.V., Nunhem (NL)

(72) Inventors: Daniel Puglisi, Sant Agata Bolognese (IT); Alberto Sirizzotti, Sant Agata Bolognese (IT); Courtney Hu, Davis, CA (US); Mona Mazaheri, Davis, CA (US)

(73) Assignee: Nunhems B.V., Nunhem (NL)

( * ) Notice: Subject to any disclaimer, the term of this patent is extended or adjusted under 35 U.S.C. 154(b) by 340 days.

(21) Appl. No.: 18/035,906

(22) PCT Filed: Nov. 2, 2021

(86) PCT No.: PCT/EP2021/080366
§ 371 (c)(1),
(2) Date: May 8, 2023

(87) PCT Pub. No.: WO2022/096451
PCT Pub. Date: May 12, 2022

(65) Prior Publication Data
US 2023/0404007 A1 Dec. 21, 2023

Related U.S. Application Data

(60) Provisional application No. 63/117,791, filed on Nov. 24, 2020, provisional application No. 63/111,941, filed on Nov. 10, 2020.

(30) Foreign Application Priority Data

Nov. 9, 2020 (EP) ..................................... 20206517

(51) Int. Cl.
*A01H 5/08* (2018.01)
*A01H 1/00* (2006.01)
*A01H 6/34* (2018.01)

(52) U.S. Cl.
CPC ............. *A01H 6/342* (2018.05); *A01H 1/106* (2021.01); *A01H 5/08* (2013.01)

(58) Field of Classification Search
None
See application file for complete search history.

(56) References Cited

U.S. PATENT DOCUMENTS

| | | | |
|---|---|---|---|
| 5,210,015 A | 5/1993 | Gelfand et al. | |
| 5,487,972 A | 1/1996 | Gelfand et al. | |
| 7,615,620 B2 | 11/2009 | Robinson | |

FOREIGN PATENT DOCUMENTS

| | | | | |
|---|---|---|---|---|
| EP | 1726664 B1 | 1/2010 | | |
| EP | 2959771 A1 | 12/2015 | | |
| WO | 2012/069539 A1 | 5/2012 | | |
| WO | 2017/098508 A1 | 6/2017 | | |
| WO | 2017/202715 A1 | 11/2017 | | |
| WO | WO2018/060444 A1 * | 4/2018 | .............. | A01H 5/08 |
| WO | 2019/238832 A1 | 12/2019 | | |

OTHER PUBLICATIONS

Seebach et al., *Arabidopsis nicotianamine* synthases comprise a common core-NAS domain fused to a variable autoinhibitory C terminus, 2023, Journal of Biological Chemistry, vol. 299(6), pp. 1-14. (Year: 2023).*

"Gene: Cla97C07G135900—Summary—Citrullus_lanatus—Ensembl Genomes 50", Database Ensembl [Online], retrieved from Database accession No. Cla97C07G135900, XP055782450, Jul. 18, 2020, 1 page.

"Transcript: Cla97C07G135900.1—cDNA sequence—Citrullus_lanatus—Ensembl Genomes 50", Database Ensembl [Online], retrieved from Database accession No. Cla97C07G135900.1, XP055782447, Jul. 18, 2020, 5 pages.

"Transcript: Cla97C07G135900.1—Protein sequence—Citrullus_lanatus—Ensembl Genomes 50", Database Ensembl [Online], retrieved from Database accession No. Cla97C07G135900.1, XP055782449, Jul. 18, 2020, 1 page.

Acciarri, et al., "Genetically modified parthenocarpic eggplants: improved fruit productivity under both greenhouse and open field cultivation", BMC biotechnology, vol. 2, Article No. 4, Apr. 4, 2002, 7 pages.

Allen, et al., "Transcript-specific, single-nucleotide polymorphism discovery and linkage analysis in hexaploid bread wheat (*Triticum aestivum* L.)", Plant biotechnology journal, vol. 9, Issue 9, Jun. 1, 2011, pp. 1086-1099.

Bhatta, et al., "Improving Horticultural Crops via CRISPR/Cas9: Current Successes and Prospects", Plants, vol. 9, Issue 10, Oct. 14, 2020, pp. 1-19.

Erpen-Dalla Corte, et al., "Development of improved fruit, vegetable, and ornamental crops using the CRISPR/Cas9 genome editing technique", Plants, vol. 8, Issue 12, Dec. 13, 2019, pp. 1-22.

European Search Report for EP Patent Application No. 20206517.3, Issued on Mar. 16, 2021, 3 pages.

Guner, et al., "The genes of watermelon", HortScience, vol. 39, Issue 6, 2004, pp. 1175-1182.

H. Kihara, "Triploid Watermelons", American Society for Horticultural Science, vol. 58, 1951, pp. 217-230.

He, et al., "SNP genotyping: the KASP assay", Crop breeding: methods and protocols, vol. 1145, 2014, pp. 75-86.

International Search Report for PCT Patent Application No. PCT/EP2021/080366, Issued on Feb. 16, 2022, 4 pages.

Lohmann, et al., "Slow Motion is required for within-plant auxin homeostasis and normal timing of lateral organ initiation at the shoot meristem in *Arabidopsis*", The Plant Cell, vol. 22, Issue 2, Feb. 5, 2010, pp. 335-348.

(Continued)

*Primary Examiner* — Amjad Abraham
*Assistant Examiner* — Christina L Meadows
(74) *Attorney, Agent, or Firm* — ArentFox Schiff LLP

(57) ABSTRACT

The present invention is directed to seedless fruit producing watermelon. The present invention also comprises methods for production of said plants and methods for producing seedless watermelon.

14 Claims, 5 Drawing Sheets

Figure 1:
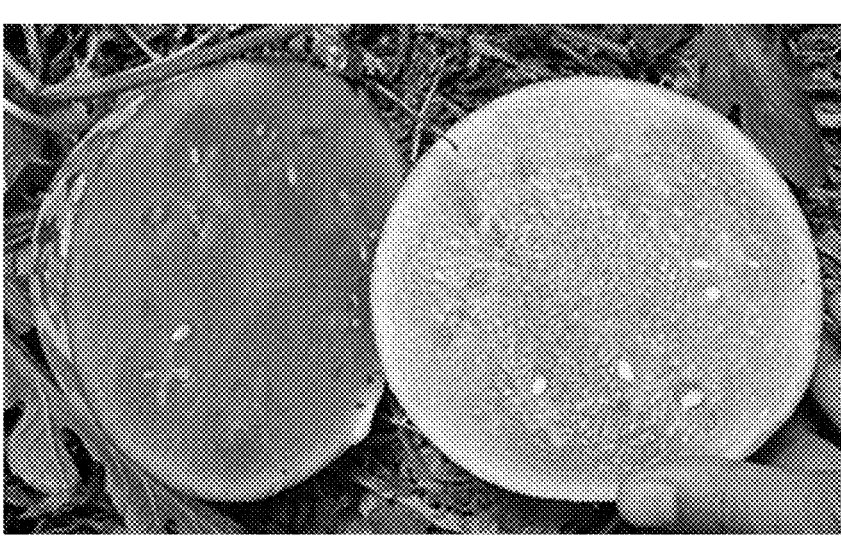

Specification includes a Sequence Listing.

(56) References Cited

OTHER PUBLICATIONS

Noh, et al., "Screening different methods of tetraploid induction in watermelon [*Citrullus lanatus* (thunb.) Manst. and Nakai", Horticulture, Environment, and Biotechnology, vol. 53, Jan. 11, 2013, pp. 521-529.

O. J. Eigsti, "About Our Cover", HortScience, vol. 6, Issue 1, Feb. 1971, 1 page.

Rotino, et al., "Open field trial of genetically modified parthenocarpic tomato: seedlessness and fruit quality", BMC biotechnology, vol. 5, Article No. 32, Dec. 21, 2005, 8 pages.

Ruan, et al., "Molecular regulation of seed and fruit set", Trends in Plant Science, vol. 17, Issue 11, Nov. 2012, pp. 656-665.

Sari, et al., "Comparison of ploidy level screening methods in watermelon: *Citrullus lanatus* (Thunb.) Matsum. and Nakai", Scientia Horticulturae, vol. 82, Issues 3-4, Dec. 23, 1999, pp. 265-277.

Sirizzotti, et al., Unpublished European Patent Application No. 16171462.1, titled "Seedless fruit producing plants", filed on May 26, 2016.

Sun, et al., "Engineering herbicide-resistant rice plants through CRISPR/Cas9-mediated homologous recombination of acetolactate synthase", Molecular plant, vol. 9, Issue 4, Apr. 2016, pp. 628-631.

Wang, et al., "CRISPR/Cas9-mediated mutagenesis of CIBG1 decreased seed size and promoted seed germination in watermelon", Horticulture Research, vol. 8, Issue 70, Apr. 1, 2021, 12 pages.

Xu, et al., "Evolution of F-box genes in plants: different modes of sequence divergence and their relationships with functional diversification", Proceedings of the National Academy of Sciences, vol. 106, Issue 3, Jan. 20, 2009, pp. 835-840.

Yin, et al., "The DefH9-iaaM-containing construct efficiently induces parthenocarpy in cucumber", Cellular and Molecular Biology Letters, vol. 11, Issue 2, Jun. 1, 2006, pp. 279-290.

Yu, et al., "Generation of transgenic watermelon resistant to Zucchini yellow mosaic virus and Papaya ringspot virus type W", Plant cell reports, vol. 30, Nov. 16, 2010, pp. 359-371.

Zhang, et al., "Characteristics of a novel male-female sterile watermelon (*Citrullus lanatus*) mutant", Scientia horticulturae, vol. 140, Jun. 1, 2012, pp. 107-114.

Zhang, et al., "Development of genic male-sterile watermelon lines with delayed-green seedling marker", HortScience, vol. 31, Issue 1, 1996, pp. 123-126.

Zhang, et al., "Tissue culture-induced heritable genomic variation in rice, and their phenotypic implications", PloS one, vol. 9, Issue 5, May 7, 2014, pp. 1-10.

* cited by examiner

Figure 2

```
WAP7.1WT      1 MDKPLDPPLDFYKPPLQPDDPTPPPPDASVLGNSHHPPHLMDSHIDDSKL    50
                |||||||||||||||||||||||||||||||||||||||||||||||||||
wap7.1        1 MDKPLDPPLDFYKPPLQPDDPTPPPPDASVLGNSHHPPHLMDSHIDDSKL    50

WAP7.1WT     51 VGVPVAGPLLPADSSPAAKLNAKFKDKVLVVDKTLGIRRRGRPPPGQVKP   100
                |||||||||||||||||||||||||||||||||||||||||||||||||||
wap7.1       51 VGVPVAGPLLPADSSPAAKLNAKFKDKVLVVDKTLGIRRRGRPPPGQVKP   100
                             Zn-binding domain
WAP7.1WT    101 PPLPPRQKKDEEDVCFICFDGGSLVLCDRRGCPKAYHPSCIKRDESFFRS   150
                |||||||||||||||||||||||||||||||||||||||||||||||||||
wap7.1      101 PPLPPRQKKDEEDVCFICFDGGSLVLCDRRGCPKAYHPSCIKRDESFFRS   150

WAP7.1WT    151 KAKWNCGWHICTNCQKASYYMCYTCPFSLCKGCIKGADYQCVRGTKGFCG   200
                |||||||||||||||||||||||||||||||||||||||||||||||||||
wap7.1      151 KAKWNCGWHICTNCQKASYYMCYTCPFSLCKGCIKGADYQCVRGTKGFCG   200

WAP7.1WT    201 TCMKIIMLFEKSAPDGESVQVDFDDKSSWEYLFKVYWIYLKEKLSLTVDE   250
                |||||||||||||||||||||||||||||||||||||||||||||||||||
wap7.1      201 TCMKIIMLFEKSAPDGESVQVDFDDKSSWEYLFKVYWIYLKEKLSLTVDE   250

WAP7.1WT    251 LVRAKNSWKGSIIMDHKVASSEILDGSIDKSQGAHNSFPNPKSQRKRPNR   300
                |||||||||||||||||||||||||||||||||||||||||||||||||||
wap7.1      251 LVRAKNSWKGSIIMDHKVASSEILDGSIDKSQGAHNSFPNPKSQRKRPNR   300

WAP7.1WT    301 QQSSLNKFGSLVDRPSSNEQFSVSTKWATTELMDFVAHVRNGDTTRLSPL   350
                |||||||||||||||||||||||||||||||||||||||||||||||||||
wap7.1      301 QQSSLNKFGSLVDRPSSNEQFSVSTKWATTELMDFVAHVRNGDTTRLSPL   350
                         Peptide Binding Domain
WAP7.1WT    351 DVQALLLEYVKKNNLRDPQQQSQINCDLRLTNLFGKSRIGHFEMLNLLQS   400
                |||||||||||||||||||||||||||||||||||||||||||||||||||
wap7.1      351 DVQALLLEYVKKNNLRDPQQQSQINCDLRLTNLFGKSRIGHFEMLNLLQS   400

WAP7.1WT    401 HVHIKGTTADNATSSGAGVVINPVESKEKYDCEVVDDCERKRKTRKKADE   450
                |||||||||||||||||||||||||||||||||||||||||||||||||||
wap7.1      401 HVHIKGTTADNATSSGAGVVINPVESKEKYDCEVVDDCERKRKTRKKADE   450
                              Plus3 Domain
WAP7.1WT    451 SRQQLHAIVDEYAAIDIQNINLIYLRRDLIVSLIDDEKFNDMVIGSIVRI   500
                |||||||||||||||||||||||||||||||||||||||||||||||||||
wap7.1      451 SRQQLHAIVDEYAAIDIQNINLIYLRRDLIVSLIDDEKFNDMVIGSIVRI   500

WAP7.1WT    501 QIPNNDEKHDFHRLVQVVGISKISTPYTVGEKTIDVMLDILNLDKRESVS   550
                |||||||||||||||||||||||||||||||||||||||||||||||||||
wap7.1      501 QIPNNDEKHDFHRLVQVVGISKISTPYTVGEKTIDVMLDILNLDKRESVS   550

WAP7.1WT    551 VQGISNQEFTEEECRRLRRSIKCGLVKRFRVSEILDKGRELQALKIKDLL   600
                |||||||||||||||||||||||||||||||||||||||||||||||||||
wap7.1      551 VQGISNQEFTEEECRRLRRSIKCGLVKRFRVSEILDKGRELQALKIKDLL   600

WAP7.1WT    601 QKEISQLTHLHDQASEKGNVDELRYFAERLHRLKSPEECQRRLLEILEVR   650
                |||||||||||||||||||||||||||||||||||||||||||||||||||
wap7.1      601 QKEISQLTHLHDQASEKGNVDELRYFAERLHRLKSPEECQRRLLEILEVR   650

WAP7.1WT    651 SDPTMDPSYESEEDKDESNKKRQGSLKRSPNYDFDEKEVELTSPRRGTNS   700
```

Figure 2 (continued)

```
                        |||||||||||||||||||||||||||||||||||||||||||||||||
wap7.1        651 SDPTMDPSYESEEDKDESNKKRQGSLKPSRNYDFDEKEVELTSPRRGTNS  700

WAP7.1WT      701 NVSGSDVQQNSTSTSEQSRNISLLAHENKEGDCLASDRTGETSWAGRGLV  750
                  |||||||||||||||||||||||||||||||||||||||||||||||||
wap7.1        701 NVSGSDVQQNSTSTSEQSRNISLLAHENKEGDCLASDRTGETSWAGRGLV  750

WAP7.1WT      751 PNNWNVPSQAKTATPLSSDGNYQVVLPEASIPPLSIGLGTSSNDAEVERI  800
                  |||||||||||||||||||||||||||||||||||||||||||||||||
wap7.1        751 PNNWNVPSQAKTATPLSSDGNYQVVLPEASIPPLSIGLGTSSNDAEVERI  800
                              Proline Binding Motif
WAP7.1WT      801 WQYQDPTGKVQGPFSMTQLRNWNNSGHFTPDLRVWRITESQNDAVLLTNA  850
                  |||||||||||||||||||||||||||||||||||||||||||||||||
wap7.1        801 WQYQDPTGKVQGPFSMTQLRNWNNSGHFTPDLRVWRITESQNDAVLLTNA  850

WAP7.1WT      851 LNGCYTKASSIWHNSHILSLGRGNGLSLGGSDNHHNGQSNGGTDSGTNLI  900
                  |||||||||||||||||||||||||||||||||||||||||||||||||
wap7.1        851 LNGCYTKASSIWHNSHILSLGRGNGLSLGGSDNHHNGQSNGGTDSGTNLI  900

WAP7.1WT      901 RFGVDPIRNSNSEQKDHIAVCDAENEPMMSTGSSSPSKDLCAPADTVNSI  950
                  |||||||||||||||||||||||||||||||||||||||||||||||||
wap7.1        901 RFGVDPIRNSNSEQKDHIAVCDAENEPMMSTGSSSPSKDLCAPADTVNSI  950

WAP7.1WT      951 QSPARNLEVAHESLKNNNSWSYPSLMNLLSSATLSLQPPVTEVHQAKENH  1000
                  |||||||||||||||||||||||||||||||||||||||||||||||||
wap7.1        951 QSPARNLEVAHESLKNNNSWSYPSLMNLLSSATLSLQPPVTEVHQAKENH  1000

WAP7.1WT     1001 SPNNEDQNSQTITLGGIHSQTGRKKRSSSEDCSSQSSGQNWIAPPATDTS  1050
                  |||||||||||||||||||||||||||||||||||||||||||||||||
wap7.1       1001 SPNNEDQNSQTITLGGIHSQTGRKKRSSSEDCSSQSSGQNWIAPPATDTS  1050

WAP7.1WT     1051 SREWNSNCSGLSLMDSFKPSEKIGEILPDIPHSTLKPVTADAEIKQSASS  1100
                  |||
wap7.1       1051 SRE----------------------------------------------  1053

WAP7.1WT     1101 SVLVQNSGLSWSSASSLPGGRQLPSHVAAGAWGGGYLAAPGRAIEDLNSS  1150 wap7.1       1054 -------------------------------------------------  1053

WAP7.1WT     1151 FITASGMKSSDIIDDHETTGATINWIDDEPNDFNSLVDESVSDLLAEVEA  1200 wap7.1       1054 -------------------------------------------------  1053

WAP7.1WT     1201 MECLSGLASTASMMNCNEGLTRDSRSDCFFSVDGFNPAAEMGKVDALSST  1250 wap7.1       1054 -------------------------------------------------  1053

WAP7.1WT     1251 ANLQFPFNIKVKDEQP    1266 wap7.1       1054 ----------------    1053
```

Figure 3

```
WAP7.1   MDKPLDPPLDFYKPRLQPDDPTPPPPDASVLGNSHHPPHLMDSHIDDSKLVGVPVAGPLL
97103    MDKPLDPPLDFYKPRLQPDDPTPPPPDASVLGNSHHPPHLMDSHIDDSKLVGVPVAGPLL
CG       MDKPLDPPLDFYKPRLQPDDPTPPPPDASVLGNSHHPPHLMDSHIDDSKLVGVPVAGPLL
         ************************************************************

WAP7.1   PADSSPAAKLNAKFKDKVLVVDKTLGIRRRGRPPRGQVKPPPLPPRQKKDEEDVCFICFD
97103    PADSSPAAKLNAKFKDKVLVVDKTLGIRRRGRPPRGQVKPPPLPPRQKKDEEDVCFICFD
CG       PADSSPAAKLNAKFKDKVLVVDKTLGIRRRGRPPPPGQVKPPPLPPRQKKDEEDVCFICFD
         ************************************************************
                                                          Zn-binding domain
WAP7.1   GGSLVLCDRRGCPKAYHPSCIKRDESFFRSKAKWNCGWHICTNCQKASYYMCYTCPFSLC
97103    GGSLVLCDRRGCPKAYHPSCIKRDESFFRSKAKWNCGWHICTNCQKASYYMCYTCPFSLC
CG       GGSLVLCDRRGCPKAYHPSCIKRDESFFPSKAKWNCGWHICTNCQKASYYMCYTCPFSLC
         ************************************************************

WAP7.1   KGCIKGADYQCVRGTKGFCGTCMKIIMLFEKSAPDGESVQVDFDDKSSWEYLFKVYWIYL
97103    KGCIKGADYQCVRGTKGFCGTCMKIIMLFEKSAPDGESVQVDFDDKSSWEYLFKVYWIYL
CG       KGCIKGADYQCVRGTKGFCGTCMKIIMLFEKSAPDGESVQVDFDDKSSWEYLFKVYWIYL
         ************************************************************

WAP7.1   KEKLSLTVDELVRAKNSWKGSIIMDHKVASSEILDGSIDKSQGAHNSFRNPKSQRKRPNR
97103    KEKLSLTVDELVRAKNSWKGSIIMDHKVASSEILDGSIDKSQGAHNSFRNPKSQRKRPNR
CG       KEKLSLTVDELVRAKNSWKGSIIMDHKVASSEILDGSIDKSQGAHNSFRNPKSQRKRPNR
         ************************************************************

WAP7.1   QQSSLNKFGSLVDRPSSNEQFSVSTKWATTELMDFVAHVRNGDTTRLSPLDVQALLLEYV
97103    QQSSLNKFGSLVDRPSSNEQFSVSTKWATTELMDFVAHVRNGDTTRLSPLDVQALLLEYV
CG       QQSSLNKFGSLVDRPSSNEQFSVSTKWATTELMDFVAHVRNGDTTRLSPLDVQALLLEYV
         ************************************************************
         Peptide Binding Domain
WAP7.1   KKNNLRDPQQQSQINCDLRLTNLFGKSRIGHFEMLNLLQSHVHIKGTTADNATSSGAGVV
97103    KKNNLRDPQQQSQINCDLRLTNLFGKSRIGHFEMLNLLQSHVHIKGTTADNATSSGAGVV
CG       KKNNLRDPQQQSQINCDLRLTNLFGKSRIGHFEMLNLLQSHVHIKGTTADNATSSGAGVV
         ************************************************************
                                                          Plus3 Domain
WAP7.1   INPVESKEKYDCEVVDDCERKRKTRKKADESRQQLHAIVDEYAAIDIQNINLIYLRRDLI
97103    INPVESKEKYDCEVVDDCERKRKTRKKADESRQQLHAIVDEYAAIDIQNINLIYLRRDLI
CG       INPVESKEKYDCEVVDDCERKPKTRKKADESRQQLHAIVDEYAAIDIQNINLIYLRRDLI
         ************************************************************

WAP7.1   VSLIDDEKFNDMVIGSIVRIQIPNNDEKHDFHRLVQVVGISKISTPYTVGEKTIDVMLDI
97103    VSLIDDEKFNDMVIGSIVRIQIPNNDEKHDFHRLVQVVGISKISTPYTVGEKTIDVMLDI
CG       VSLIDDEKFNDMVIGSIVRIQIPNNDEKHDFHPLVQVVGISKISTPYTVGEKTIDVMLDI
         ************************************************************

WAP7.1   LNLDKRESVSVQGISNQEFTEEECRRLRRSIKCGLVKRFRVSEILDKGRELQALKIKDLL
97103    LNLDKRESVSVQGISNQEFTEEECRRLRRSIKCGLVKRFRVSEILDKGRELQALKIKDLL
CG       LNLDKRESVSVQGISNQEFTEEECRRLRPSIKCGLVKRFPVSEILDKGRELQALKIKDLL
         ************************************************************

WAP7.1   QKEISQLTHLHDQASEKGNVDEL----------------------------RYFAERLHR
97103    QKEISQLTHLHDQASEKGNVDEYPFMPCHPEITLLCYRACRQWTTRSTGAEKYFAERLHR
CG       QKEISQLTHLHDQASEKGN-----------------------------------RLHR
         *******************                                   ****
```

Figure 3 (continued)

```
WAP7.1   LKSPEECQRRLLEILEVRSDPTMDPSYESEEDKDESNKKRQGSLKRSRNYDFDEKEVELT
97103    LKSPEECQRRLLEILEVRSDPTMDPSYESEEDKDESNKKRQGSLKRSRNYDFDEKEVELT
CG       LKSPEECQRRLLEILEVRSDPTMDPSYESEEDKDESNKKPQGSLKRSRNYDFDEKEVELT
         ************************************************************

WAP7.1   SPRRGTNSNVSGSDVQQNSTSTSEQSRNISLLAHENKEGDCLASDRTGETSWAGRGLVPN
97103    SPRRGTNSNVSGSDVQQNSTSTSEQSRNISLLAHENKEGDCLASDRTGETSWAGRGLVPN
CG       SPRRGTNSNVSGSDVQQNSTSTSEQSPNISLLAHENKEGDCLASDRTGETSWAGRGLVPN
         ************************************************************

WAP7.1   NWNVPSQAKTATPLSSDGNYQVVLPEASIPPLSIGLGTSSNDAEVERIWQYQDPTGKVQG
97103    NWNVPSQAKTATPLSSDGNYQVVLPEASIPPLSIGLGTSSNDAEVERIWQYQDPTGKVQG
CG       NWNVPSQAKTATPLSSDGNYQVVLPEASIPPLSIGLGTSSNDAEVERIWQYQDPTGKVQG
         ************************************************************
         Proline Binding Motif
WAP7.1   PFSMTQLRNWNNSGHFTPDLRVWRITESQNDAVLLTNALNGCYTKASSIWHNSHILSLGR
97103    PFSMTQLRNWNNSGHFTPDLPVWPITESQNDAVLLTNALNGCYTKASSIWHNSHILSLGR
CG       PFSMTQLRNWNNSGHFTPDLPVWPITESQNDAVLLTNALNGCYTKASSIWHNSHILSLGR
         ************************************************************

WAP7.1   GNGLSLGGSDNHHNGQSNGGTDSGTNLIRFGVDPIRNSNSEQKDHIAVCDAENEPMMSTG
97103    GNGLSLGGSDNHHNGQSNGGTDSGTNLIRFGVDPIPNSNSEQKDHIAVCDAENEPMMSTG
CG       GNGLSLGGSDNHHNGQSNGGTDSGTNLIRFGVDPIPNSNSEQKDHIAVCDAENEPMMSTG
         ************************************************************

WAP7.1   SSSPSKDLCAPADTVNSIQSPARNLEVAHESLKNNNSWSYPSLMNLLSSATLSLQPPVTE
97103    SSSPSKDLCAPADTVNSIQSPARNLEVAHESLKNNNSWSYPSLMNLLSSATLSLQPPVTE
CG       SSSPSKDLCAPADTVNSIQSPARNLEVAHESLKNNNSWSYPSLMNLLSSATLSLQPPVTE
         ************************************************************

WAP7.1   VHQAKENHSPNNEDQNSQTITLGGIHSQTGRKKRSSSEDCSSQSSGQNWIAPPATDTSSR
97103    VHQAKENHSPNNEDQNSQTITLGGIHSQTGPKKPSSSEDCSSQSSGQNWIAPPATDTSSR
CG       VHQAKENHSPNNEDQNSQTITLGGIHSQTGRKKRSSSEDCSSQSSGQNWIAPPATDTSSR
         ************************************************************

WAP7.1   EWNSNCSGLSLMDSFKPSEKIGEILPDIPHSTLKPVTADAEIKQSASSSVLVQNSGLSWS
97103    EWNSNCSGLSLMDSFKPSEKIGEILPDIPHSTLKPVTADAEIKQSASSSVLVQNSGLSWS
CG       EWNSNCSGLSLMDSFKPSEKIGEILPDIPHSTLKPVTADAEIKQSASSSVLVQNSGLSWS
         ************************************************************

WAP7.1   SASSLPGGRQLPSHVAAGAWGGGYLAAPGRAIEDLNSSFITASGMKSSDIIDDHETTGAT
97103    SASSLPGGRQLPSHVAAGAWGGGYLAAPGRAIEDLNSSFITASGMKSSDIIDDHETTGAT
CG       SASSLPGGRQLPSHVAAGAWGGGYLAAPGPAIEDLNSSFITASGMKSSDIIDDHETTGAT
         ************************************************************

WAP7.1   INWIDDEPNDFNSLVDESVSDLLAEVEAMECLSGLASTASMMNCNEGLTRDSRSDCFFSV
97103    INWIDDEPNDFNSLVDESVSDLLAEVEAMECLSGLASTASMMNCNEGLTRDSRSDCFFSV
CG       INWIDDEPNDFNSLVDESVSDLLAEVEAMECLSGLASTASMMNCNEGLTRDSRSDCFFSV
         ************************************************************

WAP7.1   DGFNPAAEMGKVDALSSTANLQFPFNIKVKDEQP
97103    DGFNPAAEMGKVDALSSTANLQFPFNIKVKDEQP
CG       DGFNPAAEMGKVDALSSTANLQFPFNIKVKDEQP
         **********************************
```

PARTHENOCARPIC WATERMELON PLANTS

CROSS-REFERENCE TO RELATED APPLICATIONS

This application is a National Stage Entry of PCT/EP2021/080366, filed Nov. 2, 2021, which claims priority to European Application No. 20206517.3, filed Nov. 9, 2020, U.S. Provisional Application No. 63/111,941, filed Nov. 10, 2020, and U.S. Provisional Application No. 63/117,791, filed Nov. 24, 2020, the disclosures of each of which are hereby incorporated by reference in their entireties.

FIELD

The present invention is directed to parthenocarpic watermelon plants, producing seedless fruits without pollination of the female flowers, due to the presence of a mutant allele of a recessive gene referred to as WAP7.1. When the mutant allele is in homozygous form, the unpollinated flowers produce seedless fruits. However, when the flowers are pollinated, normal seeded fruits are produced. This trait is referred to as facultative parthenocarpy. The present invention also comprises methods for production of said plants and the use of the mutant allele, referred to as wap7.1, for the production of seedless watermelon fruits.

BACKGROUND

Most commercial seedless fruits have been developed from plants whose fruits normally contain numerous relatively large hard seeds distributed throughout the flesh of the fruit. Seedless fruits are e.g. known for watermelon, tomato, cucumber, eggplant, grapes, banana, citrus fruits, such as orange, lemon and lime. As consumption of seedless fruits is generally easier and more convenient, they are considered valuable.

Fruit development normally begins when one or more egg cells in the ovular compartment of the flower are fertilized by sperm nuclei from pollen.

Seedless fruits can result from two different phenomena. In some cases fruit develops without fertilization of the ovule by pollen, a phenomenon known as parthenocarpy. In other cases seedless fruits occur after pollination when seed (embryo and/or endosperm) growth is inhibited or the seed dies early, while the remainder of the fruit continues to grow (stenospermocarpy). In contrast to parthenocarpy, stenospermocarpy requires pollination for initiation of fruit growth.

Seedless orange fruits are an example for parthenocarpy. Some orange varieties (e.g. Navel) do not produce viable pollen. They however can be cross-pollinated with pollen from other varieties. In case only the male sterile variety is grown in an orchard, there will be no pollination and parthenocarp seedless fruits will be produced. Propagation of the respective orange trees is commonly done by cuttings followed by grafting to another rootstock.

Seedless bananas are triploid. Although pollination in some cases can be normal the vast majority of fruits is seedless. This is explained by the uneven sets of chromosomes (3×) leading to improper division of chromosomes during meiosis and as a consequence to the production of non-viable pollen. Without fertilization, triploid bananas are also able to set and develop seedless fruits. Even when pollination takes place, at most one in three hundred fruits comprises a few seeds. This may be due to the triploid pollen being non-viable, for the reasons explained. Therefore, banana plants can in general be seen to be parthenocarpic. Banana plants are commonly propagated asexually from side shoots or suckers at the base of the main stalk, which can be removed and replanted to continue the cultivar. Growers also propagate bananas by means of tissue culture, in particular for producing disease free material.

Seedless cucumber, seedless squash and seedless eggplant are examples for crops which can produce seedless fruits without pollination (parthenocarpy), e.g. under conditions where pollination is impaired (e.g. low temperatures). Nevertheless, commercial quality fruit can be produced under these conditions. All these crops however can produce seed bearing fruits upon pollination. Therefore, these crops are facultative parthenocarpic. Propagation of the crops can be done by self- or cross pollination, in vitro propagation, and grafting.

From tomato mutants it is also known that they can produce seedless fruits under conditions where normal pollination/fertilization is impaired (e.g. under circumstances of low temperature). Thus, these mutants are also facultative parthenocarpic. Mutants known for showing this phenotype are pat, pat-2 and the pat-31pat-4 system. The genes underlying these mutations are not known and the pat-3 pat-4 system seems to depend on multiple loci.

Parthenocarpy has also been introduced into several plant species by means of genetic modification. Expression of a bacterial tryptophan monooxygenase (iaaM) conferring auxin synthesis under control of the ovule and placenta specific DefH9 promoter did induce parthenocarpy in cucumbers (Yin et al., 2006, Clular & molecular Biotech. Letters 11, 279-290), eggplant (Acciarri et al., 2002, BMC Biotech. 2(4)), tomato (Rotino et al., 2005, BMC Biotech. 5(32)) and tobacco.

These transgenic plants demonstrate the importance of plant hormones in seed and fruit development. That seed and fruit development are besides other factors strongly under control of several plant hormones is well known in the art. Parthenocarpy, including the logical consequence of fruit's seedlessness, can also be induced e.g. by exogenous application of plant hormones, in particular auxin or gibberellin (Ruan et al., Trends in Plant Sci. 17(11), 1360-1385).

Seedless watermelons produced currently by breeders are examples for stenospermocarp crops. Normal watermelon plants are diploid (2n). Seedless fruit producing watermelons are hybrids produced by crossing a male diploid (2n) watermelon plant with a female tetraploid (4n) watermelon plant. The resulting F1 hybrid seeds are triploid (3n). Induction of fruit setting of the triploid F1 hybrid plants requires pollination. As the triploid (3n) F1 hybrid plants do not produce fertile pollen, so called pollinator or polliniser plants have to be planted in the same field. The pollinator plants are diploid (2n). Generally a ratio of pollinator to hybrid plants of around 1 to 3 must be planted in a given scheme for providing sufficient pollen for pollinating all the F1 hybrid plants. The cross-pollination between the diploid (2n) pollinator and the flowers of the female triploid (3n) hybrid plant induces fruit set and leads to the production of seedless triploid fruits on the triploid hybrid plant. The diploid (2n) and tetraploid (4n) parents of the F1 hybrid each produce seed bearing fruits and can both be propagated independently from each other by self-pollination.

Seedless grapes can be produced from plants being either parthenocarp or stenospermocarp. The variety Black Corinth is parthenocarp, whereas Sultanina is stenospermocarp. Vine plants are in general propagated by cuttings and successive grafting to another rootstock.

Irregularities in meiosis can be a factor leading to plants producing seedless fruit. An example for plants producing seedless fruits is given in Zhang et al. (2012, Scientia Horticulture 140, 107-114), disclosing seedless watermelons. A male and female sterile (MFS) mutant was obtained from the progeny of a F1-hybrid after irradiation of its seeds with gamma-rays. Pollen from the MFS mutant was not viable at all. Seedless fruits are produced by the MFS plants, when pollinated with pollen from male fertile plants. The MFS watermelon plant therefore can be classified as being stenospermocarpic. Ovules were also nearly entirely non-viable, as almost no seeds were produced upon cross-pollination of MFS mutants with pollen from different male fertile plants. Incomplete synapsis and abnormal separation of chromatids during meiosis were observed in the MFS mutant and seen to be the cause of male and female sterility. The genes responsible for the effects present in the MFS mutant have not been identified but it seems likely that the phenotype in the MFS mutant is due to a single recessive gene.

From above discussion it is evident, that the factors determining if plants produce seedless fruits are multiple in nature and can reside in several, e.g. morphologic, physiologic and/or genetic causes.

For producing seedless fruits in stenospermocarpic crops, such as triploid (3n) watermelon plants, a female flower part of a plant must be pollinated. The stenospermocarpic crops grown today are male sterile. As a consequence, besides the female plant, a different male fertile plant (pollinator or polliniser) has to be grown in addition in the same field. As the area used for the pollinator plants is at the expense of the area which is available for the seedless fruit producing female plants, the yield per area under cultivation is reduced. In general, the pollinator plants are normal plants which can also be self-pollinated. Fruits produced by pollinator plants however do produce seeds. In watermelon, the pollinator plants are normally diploid (2n), which upon self-pollination produce seeded fruits, which may in some instances also be harvested and sold separately (see WO2012069539). For commercial reasons these seeded fruits from the pollinator plants must not be mixed with the seedless fruits. Therefore, it has to be ensured, that seedless fruits and seeded fruits are separated upon or after harvest, which may make machine harvesting difficult or impossible or require a further processing step after harvesting. Those additional precautions to be taken increase the input costs in seedless fruit production. In addition, pollinator plants are developed so that they flower and produce sufficient viable pollen at the same time the female plant flowers and its stigma can accept pollen for the induction of fruit set. Thus, the pollinator plant has to fit with the female plant producing seedless fruit in respect to flowering and fertilisation time. If flowering time of the pollinator pant and the respective female plant is not sufficiently synchronised, pollination will not take place or only take place in an insufficient amount of cases. As a result fewer fruits are produced by the stenospermocarpic female plant. Furthermore, it is well known in the art that climate conditions, like rain, heat etc., may influence pollen production of a polliniser plant differently than stigma fertility time of the genotypic different female plant. Therefore, climate conditions can also lead to asynchrony of fertility time of pollinator and female plant with the effect of lowering the yield.

The present inventors have found that mutating a single recessive gene in cultivated watermelon, referred herein to as the WAP7.1 gene, results in the watermelon plants developing seedless fruits when the flowers are not pollinated, i.e. parthenocarpy. If the flowers are pollinated, the fruits that develop produce normal viable seeds. This type of parthenocarpy is, therefore, referred to as facultative parthenocarpy, as it is only seen in the absence of pollination. The WAP7.1 gene is, therefore, responsible for facultative parthenocarpy in watermelon. Thus, when the mutant wap7.1 allele is present in homozygous form in a diploid watermelon plant, indicated herein as wap7.1/wap7.1, the plants are facultative parthenocarp and produce seedless fruits from non-pollinated flowers and normal seeded fruits from pollinated flowers.

This gene has great advantages in diploid watermelons, especially if combined with male sterility (MS) to ensure absence of pollination of the female flowers (as the male flowers produced on the plant are sterile) or combined with the emb1 mutant (e.g. in homozygous form, emb1/emb1) to ensure that, in case pollination does occur, the fruits are seedless due to the homozygous presence of the emb1 mutant in the plant. The emb1 mutant is a stenospermocarpy mutant, resulting in seedless fruits being produced upon pollination. Seeds comprising an emb1 mutant allele have been deposited by Nunhems B. V. on 27 Jan. 2016 under accession number NCIMB42532.

The WAP7.1 gene has also great advantages in triploid watermelons having e.g. two or three copies of the mutant allele because there is no need anymore to interplant such triploid watermelon plants with a pollenizer plant (which is normally needed to induce fruit set in normal tripoids, having three copies of the wild type WAP7.1 allele). These parthenocarp triploid plants produce seedless fruits without the need for pollination to induce fruit set. Therefore, basically the stenospermocarp nature of the normal triploid watermelons is changed into parthenocarpy. Yield of seedless triploid fruits is thereby increased greatly, as the pollenizer plants are not required anymore in a field and the entire field can comprise triploid watermelon plants.

In a population of mutagenized M2 diploid watermelon plants grown in insect-proof greenhouses so that no pollination could occur, a plant producing seedless fruits from un-pollinated female flowers (see FIG. 1) was observed when screening more than 20.000 plants. The fruits contained only some traces of teguments of maternal origin, similar to what is seen in known triploid seedless fruits. Genetic analysis showed that the trait segregated as a single recessive gene. The gene was designated WAP7.1, and the mutant allele was designated wap7.1.

Several F2 mapping populations were generated with different genetic backgrounds from a single plant line, which was able to produce parthenocarpic fruits. Two F2 populations were phenotyped and genotyped, derived from two different backgrounds. A QTL was mapped to a 5.6 Mb region on chromosome 7, which contained 16 mutations, of which 15 were in intergenic regions and one mutation (a single nucleotide substitution) was in a gene provided herein in SEQ ID NO: 6 (wild type, comprising a G at nucleotide 7394) and SEQ ID NO: 7 (mutant, comprising an A at nucleotide 7394), changing the codon coding for W1054 (codon TGG) into a STOP codon (codon TGA), and thereby truncating the encoded protein. FIG. 2 shows the amino acid sequences of the wild type and mutant WAP7.1 protein of SEQ ID NO: 1 and SEQ ID NO: 2, respectively. The W1054* (also referred to as W1054STOP) mutant protein thus lacks amino acids 1054 to 1266, i.e. to the end of the protein.

In the reference genome of watermelon the wild type gene is found on chromosome 7, e.g. in the Charleston Grey genome found at cucurbitgenomics.org the WAP7.1 gene is labelled ClCG07G008850.1 and is found on the plus strand starting at nucleotide 23357225 (ATG) and ending at nucleotide 23365257 (TGA). Similarly, in the reference genome of variety 97103 (genome 97103 V2) the wild type gene, labelled as Cla97C07G135900.1, is found on chromosome 7 starting at nucleotide 21927587 and ending at nucleotide Further mutants were generated and/or identified in the watermelon TILLING population having mutations in the endogenous wap7.1 allele and their phenotype will be confirmed by generating a plant homozygous for the mutant allele. Therefore, so far, the following mutants were found:

TABLE 1

| Single Nucleotide change (SNP) in the codon | Amino acid change in SEQ ID NO: 1 (and SEQ ID NO: of mutant protein comprising the amino acid change) | Position in the protein (see also FIG. 3) | Phenotype of plants homozygous for the mutant allele |
|---|---|---|---|
| G/A (AGG → AAG) | R346K (SEQ ID NO: 11) | Preceding the Peptide Binding Domain | To be determined |
| G/A (AGC → AAC) | S324N (SEQ ID NO: 12) | Preceding the Peptide Binding Domain | To be determined |
| C/T (CCT → TCT) | P830S (SEQ ID NO: 13) | Shortly after the Proline Binding Motif | To be determined |
| G/A (GCA → ACA) | A328T (SEQ ID NO: 14) | Preceding the Peptide Binding Domain | To be determined |
| G/A (TGG → TGA) | W1054* (SEQ ID NO: 2) | C-terminal part of the protein | Parthenocarpy |
| C/T (CAA → TAA) | Q373* (SEQ ID NO: 10) | In Peptide Binding Domain | To be determined |

21935619. Both genes are said to encode a "Zinc Finger CCCH domain containing protein", but no in vivo function or phenotype is known.

Although the genomic sequences are identical applicant found that the proteins which are said to be encoded by ClCG07G008850.1 and by Cla97C07G135900.1 (herein included in SEQ ID NO: 8 and SEQ ID No: 9) are different. By analyzing the mRNA sequences, applicant concluded that the differences are due to errors in the intron and exon information provided in the databases and based on mRNA sequence data the correct protein sequence was found to be that of SEQ ID NO: 1. See also FIG. 3, wherein all three proteins are shown, i.e. the CGprotein (said to be encoded by ClCG07G008850.1), the 97103 protein (said to be encoded by Cla97C07G135900.1) and the wild type WAP7.1 protein (SEQ ID NO: 1), as determined by the RNA data.

Zinc finger proteins are known to be regulators of transcription and the WAP7.1 protein contains several conserved domains, which are known to play a role in transcriptional regulation of other genes. SEQ ID NO: 1 contains four conserved domains, also shown in FIG. 2:

a) a 'Zn binding domain' starting at amino acid 114 and ending at amino acid 159, b) a 'Peptide Binding Domain' starting at amino acid 350 and ending at amino acid 395, c) a 'Plus3 domain' staring at amino acid 464 and ending at amino acid 572 and d) a 'Proline Binding Motif' starting at amino acid 812 and ending at amino acid 828 of SEQ ID NO: 1.

These conserved domains are also shown in FIG. 2 (underlined).

Even though all of the conserved domains are still present in the truncated W1054* mutant wap7.1 protein, it is highly unlikely that the truncated protein will have a function in vivo, and it is assumed that the mutation is a loss-of-function allele. As mentioned, the presence of this mutant wap7.1 allele in homozygous form in a diploid watermelon plant leads to facultative parthenocarpy, the plant produces seedless fruits in the absence of pollination of the flowers.

Therefore, one aspect herein is a watermelon plant comprising at least one mutant allele of the wap7.1 gene, whereby the mutant allele results in parthenocarpy when the mutant allele is in homozygous form, due to either a mutant protein being produced which has reduced function or loss of function compared to the wild type WAP7.1 protein, or due to the mutant allele having reduced gene expression or no gene expression compared to the wild type WAP7.1 allele, resulting in less or no wild type WAP7.1 protein being made in the plant.

A mutant wap7.1 allele may thus comprise one or more amino acids inserted, deleted or replaced compared to the wild type WAP7.1 protein, or a mutant wap7.1 allele may comprise one or more mutations in a regulatory region of the protein, such as a promoter or enhancer, resulting in reduced or no active wild type protein being made, which would thereby equally result in facultative parthenocarpy when the mutant allele is in homozygous form.

The above mutants, or other mutants in the endogenous WAP7.1 gene of a plant, can be generated by e.g. random mutagenesis or targeted mutagenesis, such as CRISPR-based methods. A review of targeted gene editing is provided e.g. by Erpen-Dalla Corte et al. in Plants 2019, 8, 601 (doi: 10.3390/plants8 120601) and by Bed Prakash Bhatta and Subas Malla in Plants 2020, 9, 1360; doi: 10.3390/plants9101360. Crispr-based editing has also already been carried out in watermelon and other cucurbit crops and can thus be used by the skilled person to edit the endogenous WAP7.1 gene of watermelon or other cucurbit species comprising an orthologous gene. For example CRISPR has been used in cucumber to generate mutants in a target gene as described in WO2017098508. Also in watermelon Crispr has been successfully used to modify target genes, see e.g. Wang, Y., Wang, J., Guo, S. et al. CRISPR/Cas9-mediated mutagenesis of ClBG1 decreased seed size and promoted seed germination in watermelon. Hortic Res 8, 70 (2021). world wide web at doi.org/10.1038/s41438-021-00506-1.

Regarding mutations in any of the four conserved domains (or in other parts of the protein), in one aspect especially mutations which lead to amino acid replacements, whereby the properties of the wild type amino acid and the replaced amino acid are different, are one aspect herein, as such different amino acid properties will reduce or abolish the proper folding and/or the normal function of the protein or of the domain. So, for example a replacement of a non-polar amino acid by a polar amino acid (comprising a hydrophilic side chain), or vice versa, or the replacement of an amino acid having a charged side chain with a non-charged or differently charged side-chain. Non-polar amino acids are Alanine (A or Ala), Cysteine (C or Cys), Glycine (G or Gly), Isoleucine (I or Ile), Leucine (L or Leu), Methionine (M or Met), Phenylalanine (F or Phe), Proline (P or Pro), Tryptophan (W or Trp), Valine (V or Val). Polar amino acids are Arginine (R or Arg), Asparagine (N or Asn), Aspartate (D or Asp), Glutamate (E or Glu), Glutamine (Q or Gln), Histidine (H or His), Lysine (K or Lys), Serine (S or Ser), Threonine (T or Thr), Tyrosine (Y or Tyr).

Thus, in one aspect any one (or more) of the non-polar amino acids of a conserved domain (selected from the four conserved domains) are replaced by a polar amino acid and/or any one (or more) of the polar amino acids of a conserved domain are replaced by a non-polar amino acid. The resulting mutant allele can then be tested for its function by generating a plant homozygous for the mutant allele and analysing the phenotype. If the mutant allele results in the plant becoming facultative parthenocarpic, then the mutant allele is an allele encodes a mutant wap7.1 protein having reduced function or no function in vivo.

In another aspect the mutant wap7.1 allele encodes a truncated protein, whereby at least 50, 60, 70, 80, 90, 100, 110, 120, 130, 140, 150, 160, 170, 180, 190, 200, 201, 202, 203, 204, 205, 206, 207, 208, 209, 210, 211, 212, 213 or more amino acids of the C-terminal end of the wild type Wap7.1 protein are missing (e.g. at least 200, 300, 400, 500, 600, 700, 800, 850, 890, 892, 893, 894 amino acids are missing) or are optionally replaced by different amino acids, rendering the protein to have a reduced in vivo function or no in vivo function. Two examples of mutant alleles encoding truncated proteins are given herein in the Examples: encoding a W1054* in SEQ ID NO: 1 (or a stop codon for the W at the equivalent position in a WAP7.1 protein comprising at least 94%, 95%, 96%, 97%, 98% or 99% sequence identity to SEQ ID NO: 1); or encoding a Q373* in SEQ ID NO: 1 (or a stop codon for the Q at the equivalent position in a WAP7.1 protein comprising at least 94%, 95%, 96%, 97%, 98% or 99% sequence identity to SEQ ID NO: 1).

In one aspect the watermelon WAP7.1 gene is the gene encoding a WAP7.1 protein, wherein a WAP7.1 protein is the protein of SEQ ID NO: 1 or a protein comprising at least 94%, 95%, 96%, 97%, 98% or 99% sequence identity to SEQ ID NO: 1. It is noted that the proteins said to be encoded by ClCG07G008850.1 (SEQ ID NO: 8) and Cla97C07G135900.1 (SEQ ID NO: 9) have 99.3% and 97.7% sequence identity to SEQ ID NO: 1. Thus, in case these protein sequences are not due to errors in intron/exon information, and these might be functional proteins (which is not believed, as explained above), these are encompassed herein. As mentioned before, the genomic sequences are 100% identical to the wild type WAP7.1 genomic gene sequence provided herein in SEQ ID NO: 6.

The watermelon WAP7.1 gene may also be referred to as ClWAP7.1, for *Citrullus lanatus* WAP7.1 and is provided herein in SEQ ID NO: 6, encoding the protein of SEQ ID NO: 1. Other cultivated watermelons may contain a allelic variant of the WAP7.1 gene, having at least 90%, 91%, 92%, 93%, 94%, 95%, 96%, 97%, 98% or 99% nucleotide sequence identity to SEQ ID NO: 6, and may encode a wild type (functional) WAP7.1 protein having at least 94%, 95%, 96%, 97%, 98% or 99% sequence identity to SEQ ID NO: 1. Such proteins are herein also referred to as functional variants of the protein of SEQ ID NO: 1 and such genes are referred to as allelic variants of the gene of SEQ ID NO: 6. Importantly, they should lead to facultative parthenocarpy when mutated to either knock-down or knock-out gene expression or when mutated to encode a reduced function or loss of function protein. E.g. an allelic variant into which the same mutation is introduced as generated herein, such as the single nucleotide change (G to A) of nucleotide 7394 of SEQ ID NO: 6 (leading to codon TGG being changed into codon TGA, i.e. W1054STOP), should give the same phenotype when homozygous present in a diploid plant.

In one aspect of the invention a plant or plant cell is provided, characterized in that the plant or plant cell has decreased activity of a WAP7.1 protein compared to a corresponding wild type plant cell, wherein the WAP7.1 protein of the wild type plant cell is encoded by nucleic acid molecules selected from the group consisting of:

a) nucleic acid molecules, which encode a protein with the amino acid sequence given under SEQ ID NO: 1 (watermelon);
  b) nucleic acid molecules, which encode a protein, the sequence of which has an identity of at least 94%, 95%, 96%, 97%, 98% or 99% with the amino acid sequence given under SEQ ID NO: 1 (watermelon);
  c) nucleic acid molecules, which encode a protein, the sequence of which has an identity of at least 94%, 95%, 96%, 97%, 98% or 99% with the amino acid sequence given under SEQ ID NO: 1 (watermelon) and wherein the protein comprises the amino acid sequence of the Zn Binding Domain, i.e. amino acids 114 to 159 of SEQ ID NO: 1, and/or it comprises the amino acid sequence of the Peptide Binding Domain, i.e. amino acids 350 to 395 of SEQ ID NO: 1, and/or it comprises the amino acids of the Plus3 Domain, i.e. amino acids 464 to 572 of SEQ ID NO: 1, and/or it comprises the amino acids of the Proline Binding Motif, i.e. amino acids 812 to 828 of SEQ ID NO: 1;
  d) a nucleic acid molecule of SEQ ID NO: 6 or a sequence comprising at least 90%, 91%, 92%, 93%, 94%, 95%, 96%, 97%, 98% or 99% sequence identity to SEQ ID NO:6 and encoding a WAP7.1 protein.

The decreased activity of the WAP7.1 protein is caused by a mutant wap7.1 allele. Decreased activity may be caused by a knock-down or knock-out of the expression of the mutant wap7.1 allele (e.g. through a mutation in the promoter or other regulatory sequence) or through the mutant wap7.1 allele encoding a loss-of-function or decreased-function WAP7.1 protein (mutant WAP7.1 protein).

In one aspect the mutant wap7.1 allele encodes a mutant WAP7.1 protein having decreased function or loss-of-function compared to the wild type protein, e.g. the mutant WAP7.1 protein comprises one or more amino acids replaced, deleted and/or inserted compared to the wild type protein. In one aspect amino acid R346, S324, P830, A328, Q373 and/or W1054 of SEQ ID NO: 1 (or the equivalent amino acid of a sequence comprising at least 94%, 95%, 96%, 97%, 98% or 99% with the amino acid sequence given under SEQ ID NO: 1) is deleted or is replaced by a different amino acid or replaced by a stop codon, leading to a reduced function or loss of function WAP7.1 protein.

In one aspect the mutant WAP7.1 protein comprises one or more amino acids replaced, deleted and/or inserted in a conserved domain of the protein selected from the group: 1.

the conserved "Zn Binding domain" domain of the protein, 2. The conserved "Peptide Binding domain", 3. the conserved "Plus3 domain" and/or 4. the conserved 'Proline Binding Domain' of the protein.

In one aspect, at least one amino acid in a conserved domain (of the 4 domains) is replaced by another amino acid or by a STOP codon, resulting in a loss of function or decreased function protein and facultative parthenocarpy when the allele is in homozygous form (when no wild type allele is present in the diploid plant or plant cell).

In another aspect one or more amino acids of a conserved domain (of the 4 domains) are missing, e.g. through a mutation causing a premature STOP codon, resulting in a loss of function or decreased function protein and facultative parthenocarpy when the allele is in homozygous form (when no wild type allele is present in the diploid plant or plant cell).

In another aspect the mutant protein is truncated, missing at least 50, 60, 70, 80, 90, 100, 110, 120, 130, 140, 150, 160, 170, 180, 190, 200, 201, 202, 203, 204, 205, 206, 207, 208, 209, 210, 211, 212, 213 or more amino acids of the C-terminal end of the wild type Wap7.1 protein of SEQ ID NO: 1 (or of a wild type protein comprising at least 94% identity to SEQ ID NO: 1) are missing or are optionally replaced by different amino acids, rendering the protein to have a reduced in vivo function or no in vivo function. In one aspect the W at position 1054 of SEQ ID NO: 1, or at the equivalent position of a protein comprising at least 94% identity to SEQ ID NO: 1, is deleted, or replaced by a different amino acid, or is replaced by a stop codon. In one aspect the Q at position 373 of SEQ ID NO: 1, or at the equivalent position of a protein comprising at least 94% identity to SEQ ID NO: 1, is deleted, or replaced by a different amino acid, or is replaced by a stop codon.

A reduced function or a loss-of function or reduced function of the protein is present when the mutant allele changes the in vivo phenotype from the wild type phenotype, i.e. fruits developing only after pollination when the wild type allele is present in homozygous form, into facultative parthenocarpy when the mutant allele is in homozygous form in a diploid plant.

The equivalent amino acids in a sequence comprising at least 94%, 95%, 96%, 97%, 98% or more sequence identity to SEQ ID NO: 1 can be identified by pairwise alignment (e.g. using the program Needle) with SEQ ID NO: 1, see e.g. FIG. 3. The equivalent amino acid of the W1054 of SEQ ID NO: 1, or of the other mutants shown in Table 1, can for example easily be identified in SEQ ID NO: 8 and 9, see FIG. 3, in which it is highlighted in bold. The equivalent amino acid in a variant sequence of at least 94% identity to SEQ ID NO: 1 is, thus, the same amino acid, but it may have a slightly different position in the variant sequence, e.g. the W1054 of SEQ ID NO: 1 may be e.g. W1055 or W1052 or W1053 in a variant protein.

In one aspect W1054 of the watermelon protein of SEQ ID NO: 1 (or the equivalent amino acid in a sequence comprising at least 94%, 95%, 96%, 97% or more sequence identity to SEQ ID NO: 1), is replaced by a different amino acid, is deleted or is replaced by a stop codon.

In one aspect Q373 of the watermelon protein of SEQ ID NO: 1 (or the equivalent amino acid in a sequence comprising at least 94%, 95%, 96%, 97% or more sequence identity to SEQ ID NO: 1), is replaced by a different amino acid, is deleted or is replaced by a stop codon.

In one aspect R346 of the watermelon protein of SEQ ID NO: 1 (or the equivalent amino acid in a sequence comprising at least 94%, 95%, 96%, 97% or more sequence identity to SEQ ID NO: 1), is replaced by a different amino acid, is deleted or is replaced by a stop codon.

In one aspect S324 of the watermelon protein of SEQ ID NO: 1 (or the equivalent amino acid in a sequence comprising at least 94%, 95%, 96%, 97% or more sequence identity to SEQ ID NO: 1), is replaced by a different amino acid, is deleted or is replaced by a stop codon.

In one aspect P830 of the watermelon protein of SEQ ID NO: 1 (or the equivalent amino acid in a sequence comprising at least 94%, 95%, 96%, 97% or more sequence identity to SEQ ID NO: 1), is replaced by a different amino acid, is deleted or is replaced by a stop codon.

In one aspect A328 of the watermelon protein of SEQ ID NO: 1 (or the equivalent amino acid in a sequence comprising at least 94%, 95%, 96%, 97% or more sequence identity to SEQ ID NO: 1), is replaced by a different amino acid, is deleted or is replaced by a stop codon.

In one aspect the mutant allele encodes the mutant protein of SEQ ID NO: 2, SEQ ID NO: 11, SEQ ID NO: 12, SEQ ID NO: 13, SEQ ID NO: 14, or SEQ ID NO: 10.

SUMMARY

A cultivated watermelon plant or plant part is provided comprising at least one copy of a mutant allele of a gene named WAP7.1, said mutant allele conferring facultative parthenocarpy when the mutant allele is in homozygous form.

In one aspect the gene is located on chromosome 7 of the watermelon genome, especially the gene is located in a region starting at base pair 23357225 and ending at base pair 23365257 of chromosome 7 of the Charleston Grey chromosome, on which it is referred to a ClCG07G08850.

In one embodiment the plant or plant part comprising the mutant allele of the WAP7.1 gene is diploid, tetraploid, triploid or polyploid. Preferably the mutant allele is present in two copies in a diploid plant or plant part, in four copies in a tetraploid plant or plant part or in one, two or three copies in a triploid plant or plant part.

Optionally the plant or plant part which comprises the mutant allele of the WAP7.1 gene further comprises a gene conferring male sterility or a gene conferring stenospermocarpy, such as the gene described in WO2017202715 and/or in WO2019238832.

Optionally the plant or plant part which comprises the mutant allele of the WAP7.1 gene further comprises a gene conferring parthenocarpy, e.g. the gene described in WO2018/060444.

The plant part comprising the mutant allele of the WAP7.1 gene may be a cell, a flower, a leaf, a stem, a cutting, an ovule, pollen, a root, a rootstock, a scion, a fruit, a protoplast, an embryo, an anther.

Also encompassed is a vegetatively propagated watermelon plant propagated from such a plant part comprising at least one mutant allele of the WAP7.1 gene.

Likewise a seed from which a plant of the invention can be grown is provided.

Further, a seedless fruit produced by a plant according to the invention is provided.

A method of producing seedless watermelon fruits is provided, said method comprising growing a diploid plant comprising two copies of a mutant allele of a WAP7.1 gene and harvesting the fruits produced by said plants. In particular the fruits develop without pollination of the female flowers, while seeded fruits are produced upon pollination of the flowers.

A method of producing seedless watermelon fruits is provided, said method comprising growing a triploid plant comprising one, two or three copies of a mutant allele of a WAP7.1 gene and harvesting the fruits produced by said plants. In particular the fruits develop without pollination of the female flowers, i.e. no pollen is required to induce fruit development.

A method for growing watermelon plants is provided, comprising growing a triploid watermelon plant comprising one, two or three copies of a mutant allele of a WAP7.1 gene, especially in a field without pollenizer plants, and optionally harvesting the seedless watermelon fruits from said plants.

A method for production of a facultative parthenocarpic cultivated watermelon plant is provided comprising the steps of:

a) introducing mutations in a population of watermelon plants or seeds; or providing a population of mutant plants or seeds (e.g. a TILLING population, e.g. M2, M3, M4 or further generation), b) selecting a plant producing seedless fruits without pollination of the female flowers and producing a seeded fruit after pollination of the female flowers;

c) optionally verifying if the plant selected under b) comprises a mutant allele of a WAP7.1 gene; and d) optionally growing the plants obtained under c).

A method for production of a facultative parthenocarpic cultivated watermelon plant is provided comprising the steps of:

a) introducing mutations in a watermelon plant or seed; or providing a population of mutant plants or seeds (e.g. a TILLING population, e.g. M2, M3, M4 or further generation), b) selecting a plant comprising a mutant allele of the WAP7.1 gene;

c) optionally selfing the selected plant to generate a plant homozygous for the mutant allele of the WAP7.1 gene;

d) optionally growing the plants.

A watermelon plant, seed or fruit produced by the method is encompassed herein.

Use of a facultative parthenocarpic watermelon plant for producing seedless watermelon fruits, preferably without pollination of the female flowers of the plant is also an aspect of the invention.

Use of a mutant wap7.1 allele of a WAP7.1 gene as described herein for producing facultative parthenocarpic watermelon plants is also an aspect of the invention.

A method for production of a cultivated watermelon plant producing seedless fruits in the absence of pollination and seeded fruits in the presence of pollination is provided comprising the steps of:

a) introducing random or targeted mutations into one or more watermelon plants, plant parts or seeds; or providing a population of mutant plants or seeds (e.g. a TILLING population, e.g. M2, M3, M4 or further generation), b) selecting a plant comprises a mutant allele of a wap7.1 gene, e.g. a mutant allele which produces significantly reduced or no wild type WAP7.1 protein (e.g. a knockout allele) or which encodes a protein which comprises one or more amino acids deleted, replaced, inserted or duplicated compared to the wild type protein, c) optionally removing any transgenic construct (e.g. CRISPR construct) from the plant, and/or d) optionally generating a plant homozygous for the mutant allele and analyzing whether seedless fruits develop in the absence of pollination and seeded fruits develop in the presence of pollination.

A method for selecting or identifying watermelon plants, seeds or plant parts is provided comprising the steps of:

a) analyzing whether the genomic DNA of the plant or plant part or seed comprises a mutant allele and/or comprises a wild type allele of the WAP7.1 gene in their genome and optionally b) selecting a plant or plant part or seed comprising one or two copies of a mutant allele of the wap7.1 gene in the genome, wherein the wild type allele of the watermelon WAP7.1 gene encodes the protein of SEQ ID NO: 1 (or a wild type protein comprising at least 94%, 95%, 96%, 97%, 98%, 99% identity to SEQ ID NO: 1.

Step a) can be carried out in various ways, using e.g. PCR based methods, sequencing based methods, nucleic acid hybridization based methods, gene expression levels, etc. In one aspect for example a KASP assay may be used.

A method for screening (e.g. genotyping) genomic DNA of watermelon plants, seeds or plant parts is provided comprising the steps of:

a) providing a sample (or a plurality of samples) of genomic DNA of a watermelon plant or of a plurality of plants (e.g. a F2 population, inbred lines, a backcross population, a breeding population, hybrid plants, etc.), b) providing a pair of PCR primers or an oligonucleotide probe, which primers or (oligonucleotide) probe comprise at least 10, 11, 12, 13, 14, 15, 16, 17, 18, 19, 20, 21, 22 or more consecutive nucleotides of the genomic WAP7.1 allele of the watermelon WAP7.1 gene and can hybridize to the genomic allele and/or amplify part of the genomic allele in a PCR assay, and c) carrying out a PCR assay using the primer pair or a hybridization assay using the probe of step b) on the sample(s) of step a), and optionally d) selecting a plant or plant part or seed comprising one or two copies of an allele (e.g. a wild type allele and/or a mutant allele) of the watermelon WAP7.1 gene in the genome, wherein the wild type allele of the watermelon WAP7.1 gene encodes the protein of SEQ ID NO: 1 (or a wild type protein comprising at least 94%, 95%, 96%, 97%, 98%, 99% identity to SEQ ID NO: 1.

In step b) a PCR primer pair is at least one forward primer, complementary to one of the DNA strands of the WAP7.1 allele and one reverse primer complementary to the other DNA strand of the WAP7.1 allele, which primer pair hybridizes to the denatured genomic DNA and amplifies part of the WAP7.1 allele in a PCR reaction. Primers can be designed to amplify the wild type or any mutant WAP7.1 allele using primer design tools. In one aspect two forward primers are used, one designed to amplify the wild type allele and one designed to amplify a mutant allele of the WAP7.1 gene, and one common reverse primer. These three primers can be used in a KASP-assay to genotype the samples of step a). Thus, in one aspect the assay in step c) is a KASP-assay, but also other genotyping assays can be used, such as those described in world wide web at biosearchtech.com/sectors/agrigenomics/agrigenomics-pcr-qpcr-technologies.

In one aspect the assay discriminates between a wild type and a mutant allele of the WAP7.1 gene, e.g. between the wild type WAP7.1 allele and a mutant allele of Table 1, or another mutant allele.

For analyzing the genomic DNA at least crude genomic DNA extraction may be necessary. The presence of a mutant allele or a wild type allele in the genomic DNA can be detected directly or indirectly. Directly may for example be by nucleic acid hybridization of e.g. oligonucleotide probes.

Indirectly may for example be by nucleic acid amplification using e.g. PCR primers which comprise e.g. a tail sequence attached to the primer and during PCR the allele-specific primer binds to the template DNA and elongates, thereby attaching the tail sequence to the newly synthesized strand and in subsequent PCR rounds a FRET cassette (fluorescent resonant energy transfer cassette) binds to the tail and emits fluorescence. The fluorescent signal can then be detected. This is used e.g. in the KASP-assay.

The mutant allele may differ from the wild type allele in various aspects, e.g. in the promoter sequence or in the protein coding sequence or in the intron/exon splice sites. The mutant allele may have a reduced gene expression or no gene expression or it may result in the production of a protein comprising one or more amino acids deleted, replaced, or inserted or duplicated compared to the wild type protein.

In one aspect the mutant allele is an allele encoding a mutant protein as described in Table 1, wherein the mutation of Table 1 is in the wild type allele of the watermelon WAP7.1 gene which encodes the protein of SEQ ID NO: 1 or at the equivalent position in a wild type allele encoding a wild type WAP7.1 protein comprising at least 94%, 95%, 96%, 97%, 98%, 99% identity to SEQ ID NO: 1.

In one aspect the plant or plant part is watermelon and the mutant allele encodes the mutant protein of SEQ ID NO: 2 or of SEQ ID NO: 10 or of SEQ ID NO: 11, SEQ ID NO: 12, SEQ ID NO: 13 or SEQ ID NO: 14.

Also methods of generating and/or selecting plants or plant parts comprising at least one mutant allele of the watermelon WAP7.1 gene in the genome is provided.

In one aspect also a method for detecting the presence of a wild type allele and/or of a mutant allele of the watermelon WAP7.1 gene in the genome is provided.

In one aspect a method for detecting whether a watermelon plant or plant part or seed comprises at least one copy of the wild type allele, e.g. encoding the protein of SEQ ID NO: 1 (or a wild type allele comprising at least 94%, 95%, 96%, 97%, 98% or 99% sequence identity to SEQ ID NO: 1), and/or comprises at least one copy of a mutant allele comprising e.g. one or more amino acids replaced, inserted or deleted with respect to the wild type allele, e.g. encoding the protein of SEQ ID NO: 2, 10, 11, 12, 13 or 14, or a mutant protein as shown in Table 1, is provided and optionally selecting a plant, plant part or seed comprising at least one copy of a mutant wap7.1 allele.

Also a KASP-assay (Kbioscience Kompetitive Allele specific PCR-genotyping Assay) is provided comprising two allele specific forward primers, e.g. a FAM primer and a VIC primer and a Common reverse primer. Obviously, other allele specific primers can be developed to detect and/or discriminate between the wild type allele and any other mutant allele comprising e.g. one or more amino acids replaced, duplicated, deleted or inserted with respect to the wild type protein.

Likewise isolated sequences or molecules of the (wild type or mutant) genomic sequence, the cDNA or mRNA sequence, protein sequences, as well as oligonucleotide primers or probes for detecting a wild type or mutant allele of the watermelon WAP7.1 gene are encompassed herein.

Also a method for generating a PCR amplification product and/or a oligonucleotide hybridization product of (a part of the) genomic DNA of watermelon plants, seeds or plant parts is provided comprising the steps of:
  a) providing a sample (or a plurality of samples) of genomic DNA of a watermelon plant or of a plurality of plants (e.g. a F2 population, inbred lines, a backcross population, a breeding population, hybrid plants, etc.),
  b) providing at least a pair of PCR primers or at least one oligonucleotide probe, which primers or (oligonucleotide) probe comprise at least 10, 11, 12, 13, 14, 15, 16, 17, 18, 19, 20, 21, 22 or more consecutive nucleotides of the genomic WAP7.1 allele of the watermelon WAP7.1 gene and can hybridize to the genomic allele and/or amplify part of the genomic allele in a PCR assay, and
  c) carrying out a PCR assay using the primer pair or a hybridization assay using the probe of step b) on the sample(s) of step a) to generate a PCR amplification product and/or an oligonucleotide hybridization product, and optionally
  d) selecting a plant or plant part or seed comprising one or two copies of an allele (e.g. a wild type allele and/or a mutant allele) of the WAP7.1 gene in the genome,
wherein the wild type allele of the watermelon WAP7.1 gene encodes the protein of SEQ ID NO: 1 (or a wild type protein comprising at least 94%, 95%, 96%, 97%, 98%, 99% identity to SEQ ID NO: 1).

Further a method for amplifying and/or hybridizing (a part of the) genomic DNA of watermelon plants, seeds or plant parts is provided comprising the steps of:
  a) providing a sample (or a plurality of samples) of genomic DNA of a watermelon plant or of a plurality of plants (e.g. a F2 population, inbred lines, a backcross population, a breeding population, hybrid plants, etc.),
  b) providing at least a pair of PCR primers or at least one oligonucleotide probe, which primers or (oligonucleotide) probe comprise at least 10, 11, 12, 13, 14, 15, 16, 17, 18, 19, 20, 21, 22 or more consecutive nucleotides of the genomic WAP7.1 allele of the watermelon WAP7.1 gene and can hybridize to the genomic allele and/or amplify part of the genomic allele in a PCR assay, and
  c) carrying out a PCR assay using the primer pair or a hybridization assay using the probe of step b) on the sample(s) of step a) to generate a PCR amplification product and/or a oligonucleotide hybridization product, and optionally
  d) selecting a plant or plant part or seed comprising one or two copies of an allele (e.g. a wild type allele and/or a mutant allele) of the watermelon WAP7.1 gene in the genome,
wherein the wild type allele of the watermelon WAP7.1 gene encodes the protein of SEQ ID NO: 1 (or a wild type protein comprising at least 94%, 95%, 96%, 97%, 98%, 99% identity to SEQ ID NO: 1).

Also a genotyping kit comprising primers and/or probes and reaction components to amplify and/or hybridize part of the genomic DNA of the WAP7.1 gene is provided.

Primers and probes are preferably labelled or modified by e.g. a tail sequence or label, to be able to detect the amplification or hybridization reaction products.

General Definition

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells plants, etc. Similarly, "a fruit" or "a plant" also refers to a plurality of fruits and plants.

As used herein, the term "plant" includes the whole plant or any parts or derivatives thereof, preferably having the same genetic makeup as the plant from which it is obtained, such as plant organs (e.g. harvested or non-harvested fruits, leaves, flowers, anthers, etc.), plant cells, plant protoplasts, plant cell tissue cultures from which whole plants can be regenerated, plant calli, plant cell clumps, plant transplants, seedlings, plant cells that are intact in plants, plant clones or micropropagations, or parts of plants, such as plant cuttings, embryos, pollen, anthers, ovules, fruits (e.g. harvested tissues or organs), flowers, leaves, seeds, clonally propagated plants, roots, stems, root tips, grafts (scions and/or root stocks) and the like. Also any developmental stage is included, such as seedlings, cuttings prior or after rooting, etc. When "seeds of a plant" are referred to, these either refer to seeds from which the plant can be grown or to seeds produced on the plant, after self-fertilization or cross-fertilization.

As used herein, the term "variety" or "cultivar" means a plant grouping within a single botanical taxon of the lowest known rank, which can be defined by the expression of the characteristics resulting from a given genotype or combination of genotypes.

The term "allele(s)" means any of one or more alternative forms of a gene at a particular locus, e.g. the WAP7.1 locus (where the WAP7.1 gene is located; the alleles of the gene may be wild type alleles designated WAP7.1, or mutant alleles designated wap7.1), all of which alleles relate to one trait or characteristic at a specific locus (e.g. facultative parthenocarpy). In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous), e.g. two identical copies of the mutant wap7.1 allele (i.e. wap7.1/wap7.1) or one copy of the mutant wap7.1 allele and one copy of the wild type allele (i.e. wap7.1/WAP7.1). Likewise a triploid plant is referred to as homozygous for the gene if it has three identical alleles of a gene (e.g. three copies of the mutant wap7.1 allele, i.e. wap7.1/wap7.1wap7.1) and a tetraploid plant is referred to as homozygous for the gene if it has four identical alleles of the gene, e.g. four copies of the mutant wap7.1 allele (i.e. wap7.1 wap7.1 wap7.1 wap7.1).

"WAP7.1 gene" is a single, recessive gene identified in cultivated watermelon on chromosome 7, which when mutated results in parthenocarpy, especially facultative parthenocarpy. WAP7.1 is the wild type (WT), functional allele as present in non-parthenocarpic cultivated watermelon plants and wap7.1 is the mutant allele resulting in parthenocarpy if the allele is in homozygous form in a diploid (wap7.1/wap7.1), triploid (wap7.1/wap7.1/wap7.1), tetraploid (wap7.1/wap7.1/wap7.1/wap7.1), or other polyploidy, e.g. octaploid, etc. In one aspect the WAP7.1 gene is the gene encoding a protein of SEQ ID NO: 1 or encoding a protein comprising at least 94%, 95%, 96%, 97% or 98% sequence identity to SEQ ID NO: 1 (watermelon), when aligned pairwise.

"Parthenocarpy" or "parthenocarpic" is generally understood in the art and also to be understood in connection with the present invention to describe the development of fruits without fertilization of the female ovule. A pollination process is not needed for producing fruits which fruits however as a consequence of the lack of pollination are seedless. Thus, parthenocarpy means herein that fruits are formed on the plant without pollination of the female flowers. Likewise a "parthenocarpic plant" or a "plant comprising a mutant gene (or mutant allele of a gene) conferring parthenocarpy when in homozygous form" means that the plant produces seedless fruits without pollination of the female flowers.

"Facultative parthenocarpy" is understood to mean that the parthenocarpy trait is not seen when the flower of the facultative parthenocarpic plant is pollinated, in which case normal fertilization and normal fruit development takes place. As normal fertilization takes place, the fruits are seeded.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

"F1 hybrid" plant (or F1 hybrid seed) is the generation obtained from crossing two inbred parent lines. Thus, F1 hybrid seeds are seeds from which F1 hybrid plants grow. F1 hybrids are more vigorous and higher yielding, due to heterosis. Inbred lines are essentially homozygous at most loci in the genome.

A "plant line" or "breeding line" refers to a plant and its progeny. As used herein, the term "inbred line" refers to a plant line which has been repeatedly selfed and is nearly homozygous. Thus, an "inbred line" or "parent line" refers to a plant which has undergone several generations (e.g. at least 5, 6, 7 or more) of inbreeding, resulting in a plant line with a high uniformity.

The term "gene" means a (genomic) DNA sequence comprising a region (transcribed region), which is transcribed into a messenger RNA molecule (mRNA) in a cell, and an operably linked regulatory region (e.g. a promoter). An example is the WAP7.1 gene of the invention. Different alleles of a gene are thus different alternatives form of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Mutant wap7.1 allele" or "wap7.1 allele" refers herein to a mutant allele of the WAP7.1 gene on chromosome 7 in watermelon, which causes the plant to be facultative parthenocarpic when the mutant allele is in homozygous form. The mutation in the mutant allele can be any mutation or combination of mutations, including deletions, truncations, insertions, point mutations, non-sense mutations, mis-sense mutations or non-synonymous mutations, splice-site mutations, frame shift mutations and/or mutations in one or more regulatory sequences such as promoter sequence, or enhancer or silencer sequences. In one aspect the mutant wap7.1 allele is a mutant allele of the WAP7.1 gene whereby the WAP7.1 gene is the gene encoding a protein of SEQ ID NO: 1 or encoding a protein comprising at least 94%, 95%, 96%, 97% or 98% or 99% sequence identity to SEQ ID NO: 1 (when aligned pairwise).

"Wild type WAP7.1 allele" or "WAP7.1 allele" refers herein to the functional allele of the WAP7.1 gene, which causes the plant to have a normal fruit set, requiring normal pollination and fertilization to set fruits. The wild type WAP7.1 allele is found in any commercial variety of watermelon (e.g. Nunhems variety Premium F1, Montreal F1, and others). In one aspect the wild type WAP7.1 allele is a wild type allele of the WAP7.1 gene whereby the WAP7.1 gene is the gene encoding a protein of SEQ ID NO: 1 or encoding a protein comprising at least 94%, 95%, 96%, 97% or 98% sequence identity to SEQ ID NO: 1 (when aligned pairwise).

The term "locus" (loci plural) means a specific place or places or a site on a chromosome where for example a gene or genetic marker is found. The WAP7.1 locus is, thus, the location in the genome of watermelon, where the mutant allele and/or the wild type allele of the WAP7.1 gene is found. The WAP7.1 locus is a locus on cultivated watermelon chromosome 7 (using the chromosome assignment of the published watermelon genome found at world wide web at cucurbitgenomics.org under "Watermelon: Genome", "Charleston Grey" or "watermelon 97103", i.e. wap7.1 was generated in the cultivated watermelon genome by mutagenesis and the mutant wap7.1 allele was mapped to a defined region of chromosome 7 of cultivated watermelon.

"Induced mutant" alleles are mutant alleles in which the mutation(s) is/are/have been induced by human intervention, e.g. by mutagenesis via physical or chemical mutagenesis methods or via e.g. tissue culture (as described in e.g. Zhang et al, Plos 9(5) e96879), including also targeted gene editing techniques (such as Crispr based techniques, TALENS, etc.).

"Diploid plant" refers to a plant, vegetative plant part(s), or seed from which a diploid plant can be grown, having two sets of chromosome, designated herein as 2n.

A "DH plant" or "doubled-haploid plant" is a diploid plant produced by doubling the haploid genome of the diploid plant using e.g. in vitro techniques. A DH plant is, therefore, homozygous at all loci.

"Triploid plant" refers to a plant, vegetative plant part(s), or seed from which a triploid plant can be grown, having three sets of chromosomes, designated herein as 3n.

"Tetraploid plant" refers to a plant, vegetative plant part(s), or seed from which a tetraploid plant can be grown, having four sets of chromosomes, designated herein as 4n.

"Polyploid plant" refers to plants having a higher ploidy than diploid, i.e. triploid (3n), tetraploid (4n), hexaploid (6n), octaploid (8n), etc.

"Pollenizer plant" or "pollenizer" refers to the (inbred or hybrid) diploid plant, or parts thereof (e.g. its pollen or scion), suitable as pollenizer for inducing fruit set on triploid plants. A pollenizer plant is, thus, able to lead to good fruit set (and good triploid fruit yield) of normal triploid plants (comprising three copies of the wild type WAP7.1 allele), by producing an appropriate amount of pollen at the appropriate day-time and for an appropriate period of time.

"Hybrid triploid plant" or "F1 triploid" or "triploid hybrid" is a triploid plant grown from hybrid, triploid seed obtained from cross fertilizing a male diploid parent with a female tetraploid parent. The male parent is used for inducing fruit set and seed production on a tetraploid female parent, resulting in fruits containing F1 hybrid triploid seeds. Both the male parent and the female parent used to produce F1 triploid seeds are inbred so that each parent line is nearly homozygous and stable.

"Seedless fruit" are fruits which contain no viable mature seeds. The fruit may contain one or more small, edible, white ovules, e.g. as seen in FIG. 1. Optionally the fruit may contain a few brown or black seeds, but these are not viable. Viable mature seeds are seeds which can be germinated in soil under appropriate conditions and grow into plants.

"Planting" or "planted" refers to seeding (direct sowing) or transplanting seedlings (plantlets) into a field by machine or hand.

"Vegetative propagation" or "clonal propagation" refers to propagation of plants from vegetative tissue, e.g. by in vitro propagation or grafting methods (using scions and rootstocks). In vitro propagation involves in vitro cell or tissue culture and regeneration of a whole plant from the in vitro culture. Grafting involves propagation of an original plant by grafting onto a rootstock. Clones (i.e. genetically identical vegetative propagations) of the original plant can thus be generated by either in vitro culture or grafting. "Cell culture" or "tissue culture" refers to the in vitro culture of cells or tissues of a plant. "Regeneration" refers to the development of a plant from cell culture or tissue culture or vegetative propagation. "Non-propagating cell" refers to a cell which cannot be regenerated into a whole plant.

"Recessive" refers to an allele which expresses its phenotype (e.g. parthenocarpy or facultative parthenocarpy) when no dominant allele is present in the diploid genome, i.e. when it is homozygous in a diploid. The mutant wap7.1 allele results in a (facultative) parthenocarp plant when present in two copies in a diploid plant, optionally in four copies in a tetraploid plant or in two or three copies in a triploid plant or in the respective number of copies in another polyploidy. The dominant allele is herein also referred to as the wild type (WT) allele.

"Cultivated watermelon" or "*Citrullus lanatus*" refers herein to *Citrullus lanatus* ssp. *vulgaris*, or *Citrullus lanatus* (Thunb.) Matsum. & Nakai subsp. *vulgaris* (Schrad.), and having good agronomic characteristics, especially producing marketable fruits of good fruit quality and fruit uniformity.

"Wild watermelon" refers herein to *Citrullus lanatus* ssp. *lanatus* and *Citrullus lanatus* ssp. *mucosospermus*, producing fruits of poor quality and poor uniformity.

"SNP marker" refers to a Single Nucleotide Polymorphism between e.g. a mutant wap7.1 allele and a wild type WAP7.1 allele. For example, SEQ ID NO: 5 provides a sequence comprising a SNP at nucleotide 51, whereby the presence of a 'G' (Guanine) indicates the presence of the wild type WAP7.1 allele and the presence of a 'A' (Adenine) indicates the presence of the mutant allele, which encodes the protein of SEQ ID NO: 2 (W1054STOP mutation). Using a SNP marker assay which can distinguish between the mutant and wild type allele of the WAP7.1 gene (i.e. an allele specific assay) one can screen pants, plant parts or the DNA therefrom for the presence of the mutant allele and/or the wild type allele. For any of the SNP markers of e.g. Table 1, a SNP markers assays can be designed based on the sequences provided herein. Such a SNP marker assay can be used to detect the mutant allele, e.g. in Marker Assisted Selection and/or SNP genotyping assays. Thus, using a SNP marker assay which can distinguish between the mutant and wild type allele of the gene (e.g. in an allele specific assay) one can screen pants, plant parts or the DNA therefrom for the presence of the mutant allele.

"INDEL marker" refers to an insertion/deletion polymorphism between e.g. a mutant wap7.1 allele and a wild type WAP7.1 allele. Using an INDEL marker assay which can distinguish between the mutant and wild type allele of the gene (e.g. an allele specific assay) one can screen pants, plant parts or the DNA therefrom for the presence of the mutant allele.

"Genotyping" methods are methods whereby the genotype or allelic composition of a plant or plant part or seed can be determined. Bi-allelic genotyping assays, such as KASP-assays, can distinguish between two alleles at a locus.

"Cultivated watermelon genome" and "physical position on the cultivated watermelon genome" and "chromosome 7" refers to the physical genome of cultivated watermelon, the reference genome is found on the world wide web at cucurbitgenomics.org under "Watermelon: Genome", e.g. "Watermelon (Charleston Grey)" and the physical chromosomes and the physical position on the chromosomes.

A "chromosome region comprising the mutant wap71 allele" refers to the genomic region of e.g. chromosome 7 of cultivated watermelon which region carries the mutant wap7.1 allele. The presence of the allele can be determined phenotypically and/or by the presence of one or more molecular markers, e.g. SNP markers, INDEL markers or other markers, linked to the mutant wap7.1 allele or preferably markers distinguishing different wap7.1 alleles or by the genomic sequence of the allele sequence itself (e.g. sequencing the allele). A marker is "linked to the wap7.1 allele", if it is physically coupled to the allele. An "allele specific marker" is a marker which is specific for a particular allele (e.g. a specific mutant allele) and is thus discriminating between e.g. the mutant allele and the wild type allele. An allele-specific marker is preferably a marker in the allele itself, i.e. in the promoter region or the transcribed region of the gene, e.g. based on a polymorphism between the wild type allele sequence and the mutant allele sequence.

A pair of "flanking markers" refers to two markers, preferably two SNP markers or two sequences comprising the SNP markers, which are linked to the wap7.1 allele, and/or which are closely linked to the wap7.1 allele, whereby the wap71 allele is located in-between the two markers or in-between the two sequences comprising the markers.

"Brix" or "degree Brix" or "° brix" refers to the mean total soluble solids content as measured on several mature fruits using a refractometer. Preferably the mean of at least three fruits, each measured between the centre and the rind of the cut-open fruit, is calculated.

"Marketable" in relation to fruit quality means that the watermelon fruits are suitable for being sold for fresh consumption, having good flavour (no off-flavours), a degree brix of at least 9.0, preferably at least 10.0 or at least 11.0 and preferably also a uniform fruit flesh color, being e.g. white (e.g. variety Cream of Saskatchewan), yellow (e.g. variety Yamato Cream 1), orange (e.g. variety Tendersweet), pink (e.g. variety Sadul), pinkish red (e.g. variety Crimson Sweet), red (e.g. variety Sugar Baby) or dark red (e.g. variety Dixie Lee).

"Uniform fruit flesh color" means that the color throughout the mature fruits, when cut open through the middle (midsection), is evenly distributed throughout the fruit flesh, i.e. not patchy. Thus, a red fruit is red throughout the fruit flesh and does not contain white patches. An example of a fruit with uniform red color is the diploid variety Premium F1 (Nunhems).

"Physical distance" between loci (e.g. between molecular markers and/or between phenotypic markers) on the same chromosome is the actually distance expressed in bases or base pairs (bp), kilo bases or kilo base pairs (kb) or megabases or mega base pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of about 1%. If no recombinants can be found, the RF is zero and the loci are either extremely close together physically or they are identical. The further apart two loci are, the higher the RF.

"Uniformity" or "uniform" relates to the genetic and phenotypic characteristics of a plant line or variety. Inbred lines are genetically highly uniform as they are produced by several generations of inbreeding. Likewise, and the F1 hybrids and the triploid hybrids which are produced from such inbred lines are highly uniform in their genotypic and phenotypic characteristics and performance.

A genetic element, an introgression fragment, or a gene or allele conferring a trait (such as parthenocarpy) is said to be "obtainable from" or can be "obtained from" or "derivable from" or can be "derived from" or "as present in" or "as found in" a plant or seed or tissue or cell if it can be transferred from the plant or seed in which it is present into another plant or seed in which it is not present (such as a non-parthenocarp line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Cultivated watermelons containing the genetic element, locus, introgression fragment, gene or allele (e.g. a mutant wap7.1 allele) can be generated de novo, e.g. by mutagenesis (e.g. chemical mutagenesis, CRISPR-Cas induced, etc.) and then e.g. be crossed into other cultivated watermelons.

"Average" or "mean" refers herein to the arithmetic mean and both terms are used interchangeably. The term "average" or "mean" thus refers to the arithmetic mean of several measurements. The skilled person understands that the phenotype of a plant line or variety depends to some extent on growing conditions and that, therefore, arithmetic means of at least 10, 15, 20, 30, 40, 50 or more plants (or plant parts) are measured, preferably in randomized experimental designs with several replicates and suitable control plants grown under the same conditions in the same experiment. "Statistically significant" or "statistically significantly" different or "significantly" different refers to a characteristic of a plant line or variety that, when compared to a suitable control show a statistically significant difference in that characteristic (e.g. the p-value is less than 0.05, $p < 0.05$, using ANOVA) from the (mean of the) control.

The term "traditional breeding techniques" encompasses herein crossing, backcrossing, selfing, selection, double haploid production, chromosome doubling, embryo rescue, protoplast fusion, marker assisted selection, mutation breeding etc., all as known to the breeder (i.e. methods other than genetic modification/transformation/transgenic methods), by which, for example, a chromosome 7 comprising a mutant wap7.1 allele can be obtained, identified and/or transferred.

"Backcrossing" refers to a breeding method by which a (single) trait, such as the facultative parthenocarpy trait, can be transferred from one (often an inferior) genetic background (also referred to as "donor") into another (often a superior) genetic background (also referred to as "recurrent parent". An offspring of a cross (e.g. an F1 plant obtained by crossing e.g. the donor with the recurrent parent watermelon, or an F2 plant or F3 plant, etc., obtained from selfing the F1), is "backcrossed" to the parent with e.g. the superior genetic background. After repeated backcrossing, the trait of the one (often inferior) genetic background will have been incorporated into the other (often superior) genetic background.

"Marker assisted selection" or "MAS" is a process of using the presence of molecular markers (such as SNP markers or INDEL markers), which are genetically and physically linked to a particular locus or to a particular chromosome region or allele specific markers, to select plants for the presence of the specific locus or region or allele. For example, a molecular marker genetically and physically linked to the mutant wap7.1 allele or an allele specific marker, can be used to detect and/or select e.g. watermelon plants, or plant parts, comprising the wap7.1 allele. The closer the linkage of the molecular marker to the locus, the less likely it is that the marker is dissociated from the locus through meiotic recombination. Likewise, the closer two markers are linked to each other the less likely it is that the two markers will be separated from one another (and the more likely they will co-segregate as a unit). Allele specific markers are preferred markers, as they select for the allele directly.

A molecular marker (or a sequence comprising a molecular marker) within 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less of another marker (or a sequence comprising the molecular marker), or of a locus, refers to a marker which is physically located within the 5 Mb, 3 Mb, 2.5 Mb, 2 Mb, 1 Mb, 0.5 Mb, 0.4 Mb, 0.3 Mb, 0.2 Mb, 0.1 Mb, 74 kb, 50 kb, 20 kb, 10 kb, 5 kb, 2 kb, 1 kb or less, of the genomic DNA region flanking the marker (i.e. either side of the marker).

"LOD-score" (logarithm (base 10) of odds) refers to a statistical test often used for linkage analysis in animal and plant populations. The LOD score compares the likelihood of obtaining the test data if the two loci (molecular marker loci and/or a phenotypic trait locus) are indeed linked, to the likelihood of observing the same data purely by chance. Positive LOD scores favour the presence of linkage and a LOD score greater than 3.0 is considered evidence for linkage. A LOD score of +3 indicates 1000 to 1 odds that the linkage being observed did not occur by chance.

"Transgene" or "chimeric gene" refers to a genetic locus comprising a DNA sequence, such as a recombinant gene, which has been introduced into the genome of a plant by transformation, such as *Agrobacterium* mediated transformation. A plant comprising a transgene stably integrated into its genome is referred to as "transgenic plant".

An "isolated nucleic acid sequence" or "isolated DNA" refers to a nucleic acid sequence which is no longer in the natural environment from which it was isolated, e.g. the nucleic acid sequence in a bacterial host cell or in the plant nuclear or plastid genome. When referring to a "sequence" herein, it is understood that the molecule having such a sequence is referred to, e.g. the nucleic acid molecule.

A "host cell" or a "recombinant host cell" or "transformed cell" are terms referring to a new individual cell (or organism) arising as a result of at least one nucleic acid molecule, having been introduced into said cell. The host cell is preferably a plant cell or a bacterial cell. The host cell may contain the nucleic acid as an extra-chromosomally (episomal) replicating molecule, or comprises the nucleic acid integrated in the nuclear or plastid genome of the host cell, or as introduced chromosome, e.g. minichromosome.

"Sequence identity" and "sequence similarity" can be determined by alignment of two peptide or two nucleotide sequences using global or local alignment algorithms. Sequences may then be referred to as "substantially identical" or "essentially similar" when they are optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimising the number of gaps. Generally, the default parameters are used, with a gap creation penalty=10 and gap extension penalty=0.5 (both for nucleotide and protein alignments). For nucleotides the default scoring matrix used is DNAFULL and for proteins the default scoring matrix is Blosum62 (Henikoff & Henikoff, 1992, PNAS 89, 10915-10919). Sequence alignments and scores for percentage sequence identity may for example be determined using computer programs, such as EMBOSS as available on the world wide web under ebi.ac.uk/Tools/psa/emboss_needle/). Alternatively sequence similarity or identity may be determined by searching against databases such as FASTA, BLAST, etc., but hits should be retrieved and aligned pairwise to compare sequence identity. Two proteins or two protein domains, or two nucleic acid sequences have "substantial sequence identity" if the percentage sequence identity is at least 85%, 90%, 92%, 93%, 94%, 95%, 98%, 99% or more (as determined by Emboss "needle" using default parameters, i.e. gap creation penalty=10, gap extension penalty=0.5, using scoring matrix DNAFULL for nucleic acids and Blosum62 for proteins).

When reference is made to a nucleic acid sequence (e.g. DNA or genomic DNA) having "substantial sequence identity to" a reference sequence or having a sequence identity of at least 80%, e.g. at least 85%, 90%, 91%, 92%, 93%, 94%, 95%, 98%, 99%, 99.2%, 99.5%, 99.9% nucleic acid sequence identity to a reference sequence, in one embodiment said nucleotide sequence is considered substantially identical to the given nucleotide sequence and can be identified using stringent hybridisation conditions. In another embodiment, the nucleic acid sequence comprises one or more mutations compared to the given nucleotide sequence but still can be identified using stringent hybridisation conditions.

"Stringent hybridisation conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridises to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridisations (Northern blots using a probe of e.g. 100 nt) are for example those which include at least one wash in 0.2×SSC at 63° C. for 20 min, or equivalent conditions. Stringent conditions for DNA-DNA hybridisation (Southern blots using a probe of e.g. 100 nt) are for example those which include at least one wash (usually 2) in 0.2×SSC at a temperature of at least 50° C., usually about 55° C., for 20 min, or equivalent conditions.

"M1 generation" or "M1 plants" in context with the present invention shall refer to the first generation that is produced directly from the mutagenic treatment. A plant grown from seeds treated with a mutagen e.g. is a representative of an M1 generation.

"M2 generation" or "M2 plant" shall refer herein to the generation obtained from self-pollination of the M1 generation. A plant grown from seeds obtained from a self-pollinated M1 plant represents a M2 plant. M3, M4, etc. refers to further generations obtained after self-pollination.

"Allelism test" refers to a genetic test whereby it can be tested whether a phenotype, e.g. facultative parthenocarpy, seen in two plant lines or varieties are determined by the same gene or locus or by different genes or loci. For example, the plants to be tested are crossed with each other (preferably after selfing to ensure they are homozygous), the segregation of the phenotypes amongst the F1 or further selfing or backcross progeny is determined. The ratio of segregation indicates if the genes or loci are allelic or if they are different. So for example if the alleles are of the same gene, F1 plants (produced by crossing two homozygous plants) will all (100%) have the same phenotype, while that may not be the case if the alleles are of different genes. Likewise in F2 plants phenotypic segregation will indicate whether the same or different genes are involved.

An "mRNA coding sequence" shall have the common meaning herein. An mRNA coding sequence corresponds to the respective DNA coding (cDNA) sequence of a gene/allele apart from that thymine (T) is replaced by uracil (U).

A "mutation" in a nucleic acid molecule (DNA or RNA) is a change of one or more nucleotides compared to the corresponding wild type sequence, e.g. by replacement, deletion or insertion of one or more nucleotides. Examples of such a mutation are point mutation, nonsense mutation, missense mutation, splice-site mutation, frame shift mutation or a mutation in a regulatory sequence.

A "nucleic acid molecule" shall have the common understanding in the art. It is composed of nucleotides comprising either of the sugars deoxyribose (DNA) or ribose (RNA).

A "point mutation" is the replacement of a single nucleotide, or the insertion or deletion of a single nucleotide.

A "nonsense mutation" is a (point) mutation in a nucleic acid sequence encoding a protein, whereby a codon in a nucleic acid molecule is changed into a stop codon. This results in a pre-mature stop codon being present in the mRNA and results in translation of a truncated protein. A truncated protein may have decreased function or loss of function.

A "missense or non-synonymous mutation" is a (point) mutation in a nucleic acid sequence encoding a protein, whereby a codon is changed to code for a different amino acid. The resulting protein may have decreased function or loss of function.

A "splice-site mutation" is a mutation in a nucleic acid sequence encoding a protein, whereby RNA splicing of the pre-mRNA is changed, resulting in an mRNA having a different nucleotide sequence and a protein having a different amino acid sequence than the wild type. The resulting protein may have decreased function or loss of function.

A "frame shift mutation" is a mutation in a nucleic acid sequence encoding a protein by which the reading frame of the mRNA is changed, resulting in a different amino acid sequence. The resulting protein may have decreased function or loss of function.

A "deletion" in context of the invention shall mean that anywhere in a given nucleic acid sequence at least one nucleotide is missing compared to the nucleic sequence of the corresponding wild type sequence or anywhere in a given amino acid sequence at least one amino acid is missing compared to the amino acid sequence of the corresponding (wild type) sequence.

A "truncation" shall be understood to mean that at least one nucleotide at either the 3'-end or the 5'-end of the nucleotide sequence is missing compared to the nucleic sequence of the corresponding wild type sequence or that at least one amino acid, but preferably at least 10, 20, 30, 40, 50, 60, 70, 80, 90, 100 or more amino acids, at either the N-terminus or the C-terminus of the protein is missing compared to the amino acid sequence of the corresponding wild type protein. The 5'-end is determined by the ATG codon used as start codon in translation of a corresponding wild type nucleic acid sequence.

"Replacement" shall mean that at least one nucleotide in a nucleic acid sequence or one amino acid in a protein sequence is different compared to the corresponding wild type nucleic acid sequence or the corresponding wild type amino acid sequence, respectively, due to an exchange of a nucleotide in the coding sequence of the respective protein.

"Insertion" shall mean that the nucleic acid sequence or the amino acid sequence of a protein comprises at least one additional nucleotide or amino acid compared to the corresponding wild type nucleic acid sequence or the corresponding wild type amino acid sequence, respectively.

"Pre-mature stop codon" in context with the present invention means that a stop codon is present in a coding sequence (cds) which is closer to the start codon at the 5'-end compared to the stop codon of a corresponding wild type coding sequence.

A "mutation in a regulatory sequence", e.g. in a promoter or enhancer of a gene, is a change of one or more nucleotides compared to the wild type sequence, e.g. by replacement, deletion or insertion of one or more nucleotides, leading for example to decreased or no mRNA transcript of the gene being made.

A "mutation in a protein" is a change of one or more amino acid residues compared to the wild type sequence, e.g. by replacement, deletion, truncation or insertion of one or more amino acid residues.

"Mutant protein" is herein a protein comprising one or more mutations in the nucleic acid sequence encoding the protein, whereby the mutation results in (the mutant nucleic acid molecule encoding) a "reduced-function" or "loss-of-function" protein, as e.g. measurable in vivo, e.g. by the phenotype conferred by the mutant allele.

"Wild type 3-dimensional structure" or "wild type protein folding" refers to the in vivo folding of the wild type protein to carry out its normal function in vivo. "Modified 3-dimensional structure or modified protein folding" refers to the mutant protein having a different folding than the wild type protein, which reduces or abolishes its normal function or activity in vivo, i.e. the protein has a reduced-function or loss-of-function.

In context of the present invention, "decreased activity" of a protein shall mean a decrease in activity of a WAP7.1 protein when compared to a corresponding wild type plant cell or a corresponding wild type plant. Decrease shall in one aspect comprise an entire knock-out or knock-down of gene expression, or the production of a loss-of-function or of a reduced-function WAP7.1 protein, e.g. a mutant WAP7.1 protein may have lost function or decreased function compared to the wild type, functional WAP7.1 protein. A decrease in activity can be a decrease in the expression of a gene encoding a WAP7.1 protein (also referred to as knock-down), or a knock-out of the expression of a gene encoding a WAP7.1 protein and/or a decrease in the quantity of a WAP7.1 protein in the cells, or a reduced-function or loss-of-function in the activity of a WAP7.1 protein in the cells.

In context with the present invention, the term "wild type plant cell" or "wild type plant" means that they comprise wild type wap7.1 alleles and not mutant wap7.1 alleles. Thus, the wild type plant or wild type plant cell is a plant or plant cell comprising fully functional WAP7.1 genes, encoding a fully functional WAP7.1 proteins (also referred to as wild type WAP7.1 protein), e.g. regarding watermelon plants or plant cells a diploid watermelon plant producing the protein of SEQ ID NO: 1 (or a protein comprising at least 94% sequence identity to SEQ ID NO: 1) and producing fruits only after pollination.

"Knock-out" or "entire knock-out" shall be understood that expression of the respective gene is not detectable anymore.

"Loss-of-function" or "reduced-function" or "decreased function" shall mean in context of the present invention that the protein, although possibly present in amounts equal or similar to a corresponding wild type protein, does not evoke its normal effect anymore, i.e. for mutant alleles encoding such a protein when present in homozygous form in a diploid plant, the plant produces seedless fruits in the absence of pollination and seeded fruits in the presence of pollination.

"Conserved domain" refer to conserved protein domains, such as the "Zn Binding domain" (or Zink Binding domain), the "Peptide Binding domain", the "Plus3 domain" and the "Proline Binding domain", which are likely involved in the proteins function in transcriptional regulation (silencing or activation) of other genes. In the watermelon WAP7.1 protein of SEQ ID NO: 1 a 'Zn Binding domain' is found from amino acid 114 to 159, or the equivalent amino acids in a protein comprising at least 94%, 95%, 96% or more sequence identity to SEQ ID NO: 1. In the watermelon WAP7.1 protein of SEQ ID NO: 1 a 'Peptide Binding domain' is found from amino acid 350 to 395, or the equivalent amino acids in a protein comprising at least 94%, 95%, 96% or more sequence identity to SEQ ID NO: 1. In the watermelon WAP7.1 protein of SEQ ID NO: 1 a 'Plus3 domain' is found from amino acid 464 to 572, or the equivalent amino acids in a protein comprising at least 94%, 95%, 96% or more sequence identity to SEQ ID NO: 1. In the watermelon WAP7.1 protein of SEQ ID NO: 1 a 'Proline Binding Domain' is found from amino acid 812 to 828, or the equivalent amino acids in a protein comprising at least 94%, 95%, 96% or more sequence identity to SEQ ID NO: 1. Conserved domains can e.g. be found in the Conserved Domain Database of the NCBI (world wide web at ncbi.nlm-.nih.gov/cdd).

"Targeted gene editing" is referred to techniques whereby endogenous target genes can be modified, e.g. one or more nucleotides can be inserted, replaced and/or deleted e.g. in the promoter or coding sequence. For example CRISPR based techniques, such as Crispr-Cas9 gene editing, Crispr-Cpf1 gene editing, or more recent techniques called 'base editing' or 'primer editing' can be used to modify endogenous target genes, such as the endogenous wild type Wap7.1 gene in watermelon (encoding the protein of SEQ ID NO: 1, or a wild type protein comprising at least 94% sequence identity to SEQ ID NO: 1). The mutants described herein can, for example, be reproduced by targeted gene editing of the wild type WAP7.1 gene.

"Oligonucleotides" or "oligos" or "oligonucleotide primers or probes" are short, single-stranded polymers of nucleic acid, e.g. at least 10, 11, 12, 13, 14, 15, 16, 17, 18, 19, 20, 21, 22, 23, 24 or more nucleotides in length. Oligos may be unmodified or modified with a variety of chemistries depending on their intended use, for example, the addition of 5' or 3' phosphate groups to enable ligation or block extension, respectively, labelling with radionuclides or fluorophores and/or quenchers for use as probes, the incorporation of thiol, amino, or other reactive moieties to enable the covalent coupling of functional molecules such as enzymes, and extension with other linkers and spacers of diverse functionality. DNA oligos are the most commonly used, but RNA oligos are also available. The length of an oligo is usually designated by adding the suffix -mer. For example, an oligonucleotide with 19 nucleotides (bases) is called a 19-mer. For most uses, oligonucleotides are designed to base-pair with a strand of DNA or RNA. The most common use for oligonucleotides is as primers for PCR (polymerase chain reaction). Primers are designed with at least part of their sequence complementary to the sequence targeted for amplification. Optimal primer length for a complementary sequence is e.g. 18 to 22 nucleotides. Optimal primer sequences for PCR are usually determined by primer design software.

"DNA microarrays" are arrays which have many microscopic spots of DNA, usually oligonucleotides, bound on a solid support. Assay targets can be DNA, cDNA, or cRNA. Depending on the system, the hybridization of targets to specific spots is detected by fluorescence, chemiluminescence, or colloidal silver or gold. Microarrays are used for multiple applications such as simultaneous measurement of the expression of large numbers of genes, enabling genome-wide gene expression analysis, as well as genotyping studies using e.g. single-nucleotide polymorphism (SNP) or InDel analysis.

"Complementary strands" refer to two strands of complementary sequence, and may be referred to as sense (or plus) and anti-sense (or minus) strands for double stranded DNA. The sense/plus strand is, generally, the transcribed sequence of DNA (or the mRNA that was generated in transcription), while the anti-sense/minus strand is the strand that is complementary to the sense sequence. For any of the sequences provided herein only one strand of the sequence is given, but the complementary strand of the given strand is also encompassed herein. The complementary nucleotides of DNA are A complementary to T, and G complementary to C. The complementary nucleotides of RNA are A complementary to U, and G complementary to C.

FIG. 1: A foto of a cross section of a watermelon fruit developed in the absence of pollination on a plant homozygous for a mutant wap7.1 allele encoding a protein wherein the nucleotide Guanine at position 7394 of SEQ ID NO: 6 is replaced by the nucleotide Adenine, resulting in the codon TGG (coding for W) to be changed into TGA (STOP codon). Amino acid W at position 1054 of SEQ ID NO: 1 is, thereby replaced by a premature STOP codon.

FIG. 2: A pairwise protein sequence alignment (using EMBOSS—Needle) of the watermelon wild type WAP7.1 protein of SEQ ID NO: 1 (labelled as 'WAP7.1WT') and the mutant, truncated WAP7.1 protein of SEQ ID NO: 2 (labelled as 'wap7.1'). The conserved domains of the protein are underlined.

FIG. 3: Multiple sequence alignment of the wild type WAP7.1 protein of SEQ ID NO: 1 of watermelon (labelled as 'WAP7.1') encoded by SEQ ID NO: 6 and the proteins disclosed on cucurbitgenomics.org as being encoded by ClCG07G008850.1 in the Charleston Grey genome (labelled as 'CG', SEQ ID NO: 8) and as being encoded by Cla97C07G135900.1 on the Watermelon 97103 V2 genome (labelled as '97103'; SEQ ID NO: 9). The W at amino acid 1054 of SEQ ID NO: 1 is highlighted in bold, as are the other mutants of Table 1. The genomic sequence of all three is 100% identical to SEQ ID NO: 6.

DETAILED DESCRIPTION

A first embodiment of the present invention concerns cultivated watermelon plants, *Citrullus lanatus*, comprising at least one copy of a mutant allele of a gene conferring parthenocarpy when the mutant allele is in homozygous form, especially facultative parthenocarpy. Thus, in one aspect cultivated watermelon plants are provided, comprising at least one copy of a mutant allele of a single recessive gene called WAP7.1.

The WAP7.1 gene is an endogenous gene of cultivated watermelon, which when mutated and in homozygous form results in parthenocarpy, especially facultative parthenocarpy.

A segregating population made by crossing the mutant parthenocarp watermelon plant identified by the inventors with an elite watermelon line enabled mapping of the WAP7.1 gene to a region on chromosome 7. Further analysis in two mapping populations led to the identification of a gene comprising a mutation which led to a premature STOP codon and a truncation of the encoded protein. The single nucleotide change (Guanine to Adenine) at nucleotide 7394 of the genomic sequence of SEQ ID NO: 7, corresponding to a single nucleotide change (Guanine to Adenine) of nucleotide 3162 of the cDNA sequence of SEQ ID NO: 4, resulted in the codon TGG (encoding amino acid W or Trp or Tryptophan) being mutated to TGA (translation STOP codon). The mutation was unique to the line and was not found in 93 whole genome resequenced lines. The gene was named WAP7.1 (for Watermelon Parthenocarpy gene on chromosome 7). To screen plants for the mutant allele an allele specific marker was designed, provided in SEQ ID NO: 5.

In the mutant parthenocarpic watermelon plant the codon for Tryptophan (W or Trp) at amino acid position 1054 of the wild type WAP7.1 protein (SEQ ID NO: 1) was replaced by a STOP codon in the mutant protein, which thereby prematurely ended at amino acid 1053 (SEQ ID NO: 2), as shown in FIG. 2. In the cDNA of the mutant allele (SEQ ID NO: 4) nucleotide 3162 is an Adenine (A), while it is a Guanine (G) in the wild type wap7.1 cDNA (SEQ ID NO:3). This single nucleotide change (or SNP, from G→A) results in the codon changing from codon TGG (encoding Trp or W) into TGA (a stop codon).

It was found that this truncation of the WAP7.1 protein lead to the protein being non-functional or having reduced function in vivo. As a result the plant homozygous for this mutant protein (and thus lacking the functional wild type protein) develops seedless fruits in the absence of pollination, and normal seeded fruits when pollination takes place. When looking at the Protein Structure Property Prediction of the wild type WAP7.1 protein in RaptorX (world wide web at raptorx.uchicago.edu/StructurePropertyPred/predict/), one can see that the amino acids downstream of W1054 contain a number of loops and alpha-helices, indicating that the C-terminal protein is involved in the overall protein folding and functioning, explaining why the absence of these structures would reduce or abolish the proteins functionality.

In one aspect a watermelon plant or plant part is provided comprising at least one copy of a mutant allele of a gene named WAP7.1, wherein said mutant allele either a) comprises one or more mutations in a regulatory element, resulting in no expression or reduced expression of the allele compared to the wild type allele, and/or b) encodes a mutant protein comprising one or more amino acids replaced, inserted or deleted compared to the wild type protein, wherein said mutant allele of a) or b) confers facultative parthenocarpy when the mutant allele is in homozygous form, and wherein the wild type watermelon allele encodes a protein of SEQ ID NO: 1 or a protein comprising at least 94%, 95%, 96% or more sequence identity to SEQ ID NO: 1.

The wild type functional WAP7.1 protein of watermelon is provided in SEQ ID NO: 1 (watermelon). There may however be some amino acid sequence variation within watermelons and functional WAP7.1 proteins may comprise e.g. at least 1, 2, 3, 4, 5, 6, 7, 8, 9, 10, 11, 12, 13, 14, 15 or more amino acids which are different than in SEQ ID NO: 1 provided herein or whereby the protein comprises comprising at least 94%, 95%, 96%, 97%, 98%, 99% or 99.3%, 99.4%, 99.5% or 99.6%, 99.7%, 99.8% or 99.9% sequence identity to the proteins of SEQ ID NO: 1 (when aligned pairwise using e.g. Emboss-Needle). For example the WAP7.1 proteins of SEQ ID NO: 8 or 9 may be functional, although it is not clear if they are real or due to an error in the databases.

Therefore, in one aspect functional variants of the watermelon protein of SEQ ID NO: 1 are proteins comprising at least 94%, 95%, 96%, 97%, 98%, 99% or 99.3%, 99.4%, 99.5% or 99.6%, 99.7%, 99.8% or 99.9% sequence identity to the protein of SEQ ID NO: 1, when aligned pairwise (using e.g. Needle with default parameters). In one aspect the amino acid sequence variation is found outside the four conserved domains, which are the Zn-binding domain, the Peptide Binding Domain, the Plus3 domain and the Proline binding motif. In one aspect the functional proteins, which comprise at least 94%, 95%, 96%, 97%, 98%, 99% or 99.3%, 99.4%, 99.5% or 99.6%, 99.7%, 99.8% or 99.9% sequence identity to the protein of SEQ ID NO: 1, therefore comprise 100% identical amino acids to SEQ ID NO: 1 for the four conserved domains mentioned and shown in FIG. 2 (underlined).

As the four conserved domains are highly conserved within the species, any mutation (deletion, insertion and/or replacement of at least 1, 2, 3, 4, 5 or more amino acids) in any of these four conserved domains is predicted to lead to the mutant WAP7.1 protein having a reduced function or no function in vivo, thereby leading to the facultative parthenocarpic phenotype when the mutant allele is in homozygous form in e.g. a diploid plant.

Thus, inserting, deleting and/or replacing one or more amino acids in the Zn-binding domain, the Peptide Binding domain, the Plus3 domain or the Proline Binding motif will negatively affect the protein function.

Therefore, in one aspect a watermelon plant or plant part is provided comprising at least one copy of a mutant allele of a gene named WAP7.1, wherein said mutant allele encodes a mutant protein comprising one or more amino acids inserted, deleted or replaced in the Zn-binding domain of the protein starting at amino acid 114 and ending at amino acid 159 of SEQ ID NO: 1 (watermelon) or the equivalent amino acids in a variant WAP7.1 protein comprising at least 94% sequence identity to SEQ ID NO: 1 and wherein said mutant allele confers facultative parthenocarpy when the mutant allele is in homozygous form.

Therefore, in another aspect a watermelon plant or plant part is provided comprising at least one copy of a mutant allele of a gene named WAP7.1, wherein said mutant allele encodes a mutant protein comprising one or more amino acids inserted, deleted or replaced in the Peptide Binding domain of the protein starting at amino acid 350 and ending at amino acid 395 of SEQ ID NO: 1 (watermelon) or the equivalent amino acids in a variant WAP7.1 protein comprising at least 94% sequence identity to SEQ ID NO: 1 and wherein said mutant allele confers facultative parthenocarpy when the mutant allele is in homozygous form.

In another aspect a watermelon plant or plant part is provided comprising at least one copy of a mutant allele of a gene named WAP7.1, wherein said mutant allele encodes a mutant protein comprising one or more amino acids inserted, deleted or replaced in the Plus3 domain of the protein starting at amino acid 464 and ending at amino acid 572 of SEQ ID NO: 1 (watermelon) or the equivalent amino acids in a variant WAP7.1 protein comprising at least 94% sequence identity to SEQ ID NO: 1 and wherein said mutant allele confers facultative parthenocarpy when the mutant allele is in homozygous form.

In yet another aspect a watermelon plant or plant part is provided comprising at least one copy of a mutant allele of a gene named WAP7.1, wherein said mutant allele encodes a mutant protein comprising one or more amino acids inserted, deleted or replaced in the Proline Binding Motif of the protein starting at amino acid 812 and ending at amino acid 828 of SEQ ID NO: 1 (watermelon) or the equivalent amino acids in a variant WAP7.1 protein comprising at least 94% sequence identity to SEQ ID NO: 1 and wherein said mutant allele confers facultative parthenocarpy when the mutant allele is in homozygous form.

The term 'starting at' and 'ending at' or 'from' and 'to' includes the first and last amino acid mentioned.

Thus, insertion, deletion and/or replacement of one or more amino acids in the Zn-binding domain, the Peptide Binding domain, the Plus3 domain or the Proline Binding motif, may be the insertion, deletion and/or replacement of at least 1, 2, 3, 4, 5, 6, 7, 8, 9, 10 or more amino acids.

In yet another aspect a watermelon plant or plant part is provided comprising at least one copy of a mutant allele of a gene named WAP7.1, wherein said mutant allele encodes a mutant protein comprising at least 10, 20, 30, 40, 50, 60, 70, 80, 90, 100, 110, 120, 130, 140, 150, 160, 170, 180, 190, 200 or more amino acids inserted, deleted and/or replaced in SEQ ID NO: 1 or in a variant WAP7.1 protein or a protein comprising at least 94% sequence identity to SEQ ID NO: 1, and wherein said mutant allele confers facultative parthenocarpy when the mutant allele is in homozygous form. The mutant WAP7.1 protein may thus e.g. be truncated at the N-terminal or C-terminal, lacking said at least 10 or more amino acids at the N-terminal or C-terminal, or any other at least 10 amino acids may be deleted, replaced or inserted compared to the wild type functional WAP7.1 protein.

In yet another aspect a watermelon plant or plant part is provided comprising at least one copy of a mutant allele of a gene named WAP7.1, wherein said mutant allele encodes a mutant protein comprising at least 1, 2, 3, 4, 5, 6, 7, 8 or 9 or more amino acids inserted, deleted and/or replaced in SEQ ID NO: 1 or in a variant WAP7.1 protein or a protein comprising at least 94% sequence identity to SEQ ID NO: 1, and wherein said mutant allele confers facultative parthenocarpy when the mutant allele is in homozygous form. The mutant WAP7.1 protein may thus comprise at least 1 amino acid deleted, replaced or inserted compared to the wild type functional WAP7.1 protein. For example, the amino acid deleted or replaced (e.g. by a stop codon or by a different amino acid) may be R346, S324, P830, A328, Q373 or W1054, as shown in Table 1.

Mutant alleles can be generated by various techniques, such as random mutagenesis or targeted gene editing, and the phenotype of the mutant allele can then be analysed in plants homozygous for the mutant allele.

Any mutant allele which results in an insertion, deletion and/or replacement of one or more amino acids of the wild type, functional protein may result in a mutant protein having reduced function or no function and may thus result in the phenotype of facultative parthenocarpy when the mutant allele is in homozygous form. Plants and plant parts comprising such mutant alleles are one embodiment herein.

The 'equivalent amino acid' can easily be determined by amino acid sequence alignment, see e.g. FIG. 3, where the equivalent amino acids are highlighted in bold.

A mutation in the codon may be a (at least one) nucleotide insertion, deletion or replacement in the codon, leading to e.g. a different reading frame or a different codon, e.g. encoding a different amino acid or a STOP codon. Also the entire codon may be deleted or replaced by a different codon (or optionally a stop codon), resulting in either a deletion of the encoded amino acid, or the replacement thereof.

In one aspect the mutant allele encodes an amino acid substitution or a stop codon of amino acid number W1054 of SEQ ID NO: 1 or the equivalent amino acid in a protein comprising at least 94%, 95%, 96%, 97%, 98% or 99% sequence identity to SEQ ID NO: 1.

In one aspect the mutant allele encodes an amino acid substitution or a stop codon of amino acid number R346 of SEQ ID NO: 1 or the equivalent amino acid in a protein comprising at least 94%, 95%, 96%, 97%, 98% or 99% sequence identity to SEQ ID NO: 1.

In one aspect the mutant allele encodes an amino acid substitution or a stop codon of amino acid number S324 of SEQ ID NO: 1 or the equivalent amino acid in a protein comprising at least 94%, 95%, 96%, 97%, 98% or 99% sequence identity to SEQ ID NO: 1.

In one aspect the mutant allele encodes an amino acid substitution or a stop codon of amino acid number P830 of SEQ ID NO: 1 or the equivalent amino acid in a protein comprising at least 94%, 95%, 96%, 97%, 98% or 99% sequence identity to SEQ ID NO: 1.

In one aspect the mutant allele encodes an amino acid substitution or a stop codon of amino acid number A328 of SEQ ID NO: 1 or the equivalent amino acid in a protein comprising at least 94%, 95%, 96%, 97%, 98% or 99% sequence identity to SEQ ID NO: 1.

In one aspect the mutant allele encodes an amino acid substitution or a stop codon of amino acid number Q373 of SEQ ID NO: 1 or the equivalent amino acid in a protein comprising at least 94%, 95%, 96%, 97%, 98% or 99% sequence identity to SEQ ID NO: 1.

In one aspect the mutant allele encodes a mutant WAP7.1 protein which comprises a truncation of at least 10, 20, 30, 40, 50, 60, 70, 80, 90, 100, 110, 120, 130, 140, 150, 160, 170, 180, 190, 200, 210, 213 amino acids of the C-terminal end of the protein of SEQ ID NO: 1 or of the C-terminal end of a protein comprising at least 94% sequence identity to SEQ ID NO: 1. In one aspect all amino acids starting at (and including) amino acid W1054 of SEQ ID NO: 1, or the equivalent amino acid in a protein comprising at least 94% sequence identity to SEQ ID NO: 1, are deleted or replaced by one or more different amino acids. In another aspect all amino acids starting at (and including) amino acid Q373 of SEQ ID NO: 1, or the equivalent amino acid in a protein comprising at least 94% sequence identity to SEQ ID NO: 1, are deleted or replaced by one or more different amino acids.

As mentioned the watermelon plant or seed or plant part may comprise a mutant wap7.1 allele, wherein the mutant allele is produced by random mutagenesis or targeted mutagenesis, such as CRISPR based methods. Random mutagenesis may for example be chemical induced (e.g. EMS treatment) or radiation induced mutagenesis or other methods, whereby mutations are randomly induced in the genome and then plants or plant parts comprising mutations in the endogenous wap7.1 gene can be screened for and identified. Targeted mutagenesis are methods whereby mutations are specifically introduced into a target gene, such as the wap7.1 gene, using e.g. Crispr-Cas9, or Crispr-Cpf1 or other known methods. It is noted that using such methods, the mutant alleles described in e.g. Table 1 can be generated without undue burden or other mutant alleles can be made.

When referring herein to a watermelon plant this encompasses in one aspect a seed from which the plant can be grown, i.e. the embryo in the seed may comprise at least one copy of mutant wap7.1 allele as described.

In one aspect the plant comprising the mutant allele is not produced exclusively by an essentially biological process, meaning that the mutant allele has at one point been generated by human intervention. If such a human generated mutant allele is transferred from one plant to another by crossing and selection, then the patent covers plants comprising the mutant allele, even if the plant itself has been generated solely by crossing and selection. Preferably the plant is not transgenic, and e.g. any construct used to modify the endogenous gene, in case of targeted gene editing, has been removed from the genome. Also the plant is preferably not a transgenic plant in that the mutant wap7.1 allele has not been introduced from the outside and integrated anywhere in the plant genome using plant transformation techniques, but rather the mutant allele is an endogenous, wild type WAP7.1 allele which has been mutated (using targeted or random mutagenesis) at the locus in the genome where the wild type allele is located.

In one aspect the watermelon plant is diploid and comprises at least one copy of a mutant wap7.1 allele as described above, i.e. the plant is heterozygous. As the phenotype is only seen when the mutant allele is in homozygous form, these plants are not facultative parthenocarp, but produce normal seeded fruits upon pollination and no fruits in the absence of pollination of the flowers. Selfing of such heterozygous plants will generate a plant which is homozygous and which comprises two copies of the mutant allele. In one aspect the watermelon plant is diploid and comprises two copies of a mutant wap7.1 allele as described above, i.e. the plant is homozygous. The plant is therefore also facultative parthenocarp, producing seedless fruits in the absence of pollination and seeded fruits if pollination takes place.

The plants and plant parts comprising at least one copy of a mutant wap7.1 allele is preferably a cultivated plant, not a wild plant. So preferably cultivated watermelon (*Citrullus lanatus*). The plant may be an inbred line, a F1 hybrid or a breeding line.

In one aspect the plant is a watermelon plant and the watermelon plant is diploid, triploid or tetraploid, comprising at least one copy of a mutant wap7.1 allele. The diploid plant or plant part comprises in one aspect two copies, the triploid plant or plant part comprises one, two or three copies and the tetraploid plant or plant part comprises two or four copies of the mutant wap7.1 allele.

Also seeds from which a plant or plant part as described above can be grown are encompassed herein.

Likewise a fruit produced by a plant described above is encompassed herein, optionally wherein the fruit is seedless and is produced in the absence of pollination.

The plant or plant part according may further comprises a gene conferring male sterility or a gene conferring stenospermocarpy or another gene conferring parthenocarpy.

The plant part may be a cell, a flower, a leaf, a stem, a cutting, an ovule, pollen, a root, a rootstock, a scion, a fruit, a protoplast, an embryo, an anther.

Further a vegetatively propagated plant propagated from a plant part and comprising at least one copy of a mutant wap7.1 allele in its genome is provided.

In one aspect also a method of producing seedless watermelon fruits is provided, said method comprising growing a diploid watermelon plant comprising two copies of a mutant wap7.1 allele as described, whereby pollination of the flowers is prevented during the growing. Preventing pollination can be done by various methods, e.g. removal of male flowers or male reproductive organs (stamen, pollen), growing in insect free environments and/or male sterility of the plant.

In a further aspect a method of producing seedless watermelon fruits is provided, said method comprising growing a triploid watermelon plant comprising one, two or three copies of mutant wap7.1 allele as described, whereby no pollenizer plant is present during the growing.

A method for screening or detecting or genotyping plants, seeds, plant parts or DNA therefrom for the presence of a mutant allele of a of a gene named WAP7.1, or for selecting a plant, seed or plant part comprising a mutant allele of a of a gene named WAP7.1, or for generating a plant, seed or plant part comprising a mutant allele of a gene named WAP7.1, is provided, wherein said mutant allele either a) comprises one or more mutations in a regulatory element, resulting in no expression or reduced expression of the allele compared to the wild type allele, and/or b) encodes a mutant protein comprising one or more amino acids replaced, inserted and/or deleted compared to the wild type protein, wherein the wild type watermelon allele encodes a protein of SEQ ID NO: 1 or a protein comprising at least 94% sequence identity to SEQ ID NO: 1.

In one aspect the mutant wap7.1 allele comprises a mutation in the genomic DNA, resulting in the expression of a mutant WAP7.1 protein comprising one or more amino acids inserted, deleted or replaced as described above, e.g. W1054 of SEQ ID NO: 1 (or the equivalent amino acid in a sequence comprising at least 94% identity to SEQ ID NO: 1) or e.g. as shown in Table 1.

However, also different mutant alleles of the WAP7.1 gene, causing facultative parthenocarpy when in homozygous form, are embodiments of the invention. Such different mutant wap7.1 alleles can be generated by the skilled person without undue burden. The skilled person can, for example, generate other mutants in the WAP7.1 gene and determine whether they equally result in facultative parthenocarpy when in homozygous form in a diploid watermelon plant.

Having identified the nucleotide sequence of the gene, the skilled person can generate watermelon plants comprising mutants in the WAP7.1 gene by various methods, e.g. mutagenesis, TILLING or CRISPR-Cas or other methods known in the art. Especially with targeted gene modification technologies such as Crispr-Cas, TALENS and others, targeted mutations can be made in e.g. the promoter or coding sequence of the gene by the person skilled in the art. The skilled person can then confirm the phenotype of a plant homozygous for the mutant wap7.1 allele, i.e. being facultative parthenocarpic. Therefore, the skilled person is not limited to the specific WAP7.1 mutants generated by the inventors (which the skilled person can also generate), but the skilled person can equally generate other mutations in the wap7.1 allele of watermelon and thereby generate other mutants which lead to facultative parthenocarpy when in homozygous form. Various mutations can be generated and tested for the resulting phenotype, for example the regulatory elements can be mutated to reduce expression (knock-down) or eliminate expression (knock-out) of the allele and thus reduce or eliminate the amount of wild type WAP7.1 protein present in the cell or plant. Alternatively, mutations which lead to reduced function or loss-of-function of the WAP7.1 protein can be generated, i.e. mutations (such as missense mutations or frame shift mutations) which lead to one or more amino acids being substituted, inserted and/or deleted, or whereby the protein is truncated through the introduction of a premature stop-codon in the coding sequence (non-sense mutations). As the WAP7.1 protein comprises four conserved domains it is in one aspect encompassed that one or more amino acids are replaced, deleted and/or inserted in any one of these domains, as such mutations will likely reduced the protein function or result in a loss of function. Whether the mutation results in the expected phenotype (facultative parthenocarpy) can then be tested by generating plants homozygous for the mutation through selfing and growing the plant line with and without pollination of the flowers to see if fruits develop in a facultative parthenocarpic way.

Alternatively, the skilled person can carry out a method for production of a facultative parthenocarpic cultivated watermelon plant comprising the steps of:

a) introducing mutations in a (population of) watermelon plant(s) or seed(s), especially a cultivated plant, or providing a (population of) mutated plant(s) or seed or progeny thereof;

b) selecting a plant producing seedless fruits without pollination of the female flowers and producing a seeded fruit after pollination of the female flowers;

c) optionally determining if the plant selected under b) comprises a mutant allele of a WAP7.1 gene; and d) optionally growing the plants obtained under c).

Steps b) and c) can also be switched, so that step b) is selecting a plant comprising a mutant allele of a WAP7.1 gene and step c) is determining if the plant (or a progeny thereof produced by selfing) producing seedless fruits without pollination of the female flowers and producing a seeded fruit after pollination of the female flowers.

Step a) can be carried out by e.g. mutagenizing seeds of one or more lines or varieties of watermelon, for example by treatment with mutagenizing agents such as chemical mutagens, e.g. EMS (ethyl methane sulphonate), or irradiation with UV radiation, X-rays or gamma rays or the like. The population may for example be a TILLING population. Preferably the mutagenized plant population is selfed at least once (e.g. to produce an M2 generation, or M3, M4, etc.) prior to carrying out step b). In step b) relating to phenotyping, plants are preferably grown in an insect proof environment to avoid the presence of insect pollinators. Regular visual inspection of female flowers, fruit setting of those flowers without pollination and visual inspection of the mature fruits (e.g. presence of viable seeds or seedless) can be carried out to identify mutants which producing seedless fruits without pollination of the female flowers. Such plants, or selfing progeny thereof, can be tested for the presence of the mutant WAP7.1 gene by pollinating the female flowers to see if the fruits are seeded after pollination, genotyping the plants for mutations in the WAP7.1 gene and encoded protein, or expression of the WAP7.1 gene, sequencing and other methods known to the skilled person. There are, thus, various methods, or combinations of methods, for verifying if a phenotypically selected plant comprises a mutant allele of a WAP7.1 gene. If step b) is the selection of plants comprising a mutant allele of the WAP7.1 gene, the skilled person can also use various methods for detecting the DNA, mRNA or protein of the WAP7.1 gene in order to identify a plant comprising a mutant wap7.1 allele. The genomic DNA of the wild type watermelon wap7.1 gene, encoding a functional WAP7.1 protein (SEQ ID NO: 1) is the DNA of SEQ ID NO: 6 and the cDNA (mRNA) encoding the protein of SEQ ID NO: 1 is given in SEQ ID NO: 3. The promoter is upstream of this sequence and can e.g. be retrieved by sequencing or from the watermelon genome database. As genomic sequences encoding a certain protein may vary slightly (e.g. due to degeneracy of the genetic code or due to variation in intron sequences), the genomic alleles encoding a wild type WAP7.1 protein may comprise at least 90%, 92%, 93%, 94%, 95%, 96%, 97%, 98%, 99% sequence identity to SEQ ID NO: 6.

In one aspect the mutant allele of the WAP7.1 gene is a mutant allele resulting in reduced expression or no expression of the WAP7.1 gene or is a mutant allele resulting in one or more amino acids of the encoded WAP7.1 protein being replaced, inserted or deleted, compared to the wild type WAP7.1 protein.

In one aspect the mutant allele of the WAP7.1 gene is obtainable by inducing mutations, either targeted or random, into the gene (promoter or other regulatory elements, splice sites, coding region, etc.) and selecting plants, e.g. from the progeny, comprising a mutant wap7.1 allele. In one aspect an allele comprising a mutation in a codon, especially in a codon of the Zn-binging domain, or of the Peptide Binding domain, or of the Plus3 domain or of the Proline Binding motif, is selected, e.g. a mutation which causes an amino acid replacement, a frame shift or a stop-codon. In one aspect the mutant allele causes a truncation of the encoded watermelon WAP7.1 protein.

In one aspect the SNP marker Adenine (A) at nucleotide 51 of SEQ ID NO: 5 (marker mWM23348403) is detected in the genome of a watermelon plant or plant part, or DNA therefrom. This SNP marker detects the allele comprising the W1054STOP mutation in watermelon. In another aspect the SNP marker as shown in Table 1 is detected in the genome of a watermelon plant or plant part, or DNA therefrom, to detect the mutant allele shown in Table 1, causing an amino acid change with respect to the wild type protein of SEQ ID NO: 1 or the equivalent amino acid change in a wild type protein comprising at least 94%, 95%, 96%, 97% or more sequence identity to SEQ ID NO: 1.

For other mutant wap7.1 alleles, similar SNP markers (or other markers) and SNP genotyping (or other genotyping) assays can easily be designed. Thus, allele specific markers and detection methods are encompassed herein, especially for any mutant allele which results in an amino acid insertion, deletion or replacement in one of the conserved domains of a WAP7.1 protein of watermelon, but also other mutant alleles.

Especially in one aspect the genotype of marker mWM23348403 can be determined and used to select progeny plants comprising a Adenine at nucleotide 51 of SEQ ID NO: 5 and thus comprising the mutant wap7.1 allele in which the encoded WAP7.1 protein is truncated and lacks all amino acids downstream (C-terminal) of amino acid 1053 of SEQ ID NO: 1 (or the equivalent amino acid of a sequence comprising at least 94% identity to SEQ ID NO: 1). Similar allele specific markers for other mutant alleles (e.g. shown in Table 1) can be easily designed by the skilled person and used in genotyping assays or for selection in breeding programs.

The diploid plant heterozygous for wap7.1 (i.e. wap7.1/WAP7.1) will be heterozygous for the SNP marker, e.g. will have the genotype 'AG' for nucleotide 51 of SEQ ID NO: 5

(i.e. the plant comprises one chromosome having a Adenine, A, at nucleotide 51 of SEQ ID NO: 5 or at nucleotide 51 of a sequence comprising at least 92%, 93%, 94%, 95%, 96%, 97%, 98% or more sequence identity to SEQ ID NO:5 and a second chromosome having a Guanine, G, at nucleotide 51 of SEQ ID NO: 5 or at nucleotide 51 of a sequence comprising at least 92%, 93%, 94%, 95%, 96%, 97%, 98% or more sequence identity to SEQ ID NO:5), while a plant homozygous for wap7.1 (i.e. wap7.1/wap7.1) will have the genotype 'AA' for nucleotide 51 of SEQ ID NO: 5 (i.e. the plant comprises two chromosomes which both have a Adenine, A, at nucleotide 51 of SEQ ID NO: 5 or at nucleotide 51 of a sequence comprising at least 92%, 93%, 94%, 95%, 96%, 97%, 98% or more sequence identity to SEQ ID NO:5).

The marker mWM23348403 was designed based on the induced mutation of nucleotide 7394 (Guanine) in the genomic DNA of the wild type WAP7.1 gene of SEQ ID NO: 6 to Adenine (G7394→A), whereby the codon TGG (encoding Trp or W) is changed into the codon TGA encoding a STOP codon, resulting in a translation stop and a truncated WAP7.1 protein. Thus, nucleotide 7394 of the genomic WAP7.1 sequence of SEQ ID NO: 6 corresponds to nucleotide 51 of marker mWM23348403 of SEQ ID NO: 5.

Mutant-allele-specific markers and marker assays can equally easily be developed for any mutant wap7.1 allele (e.g. those shown in Table 1), as the underlying genomic change, e.g. in a codon, can be used to design a marker assay to detect the genomic change, e.g. underlying the amino acid changes disclosed herein or other genomic changes in the mutant wap7.1 allele compared to the wild type WAP7.1 allele.

Using such allele-specific markers, which detect specific mutant wap7.1 alleles, genotyping can be carried out to detect the presence and copy number of the allele in plants and plant material (or DNA derived therefrom). So in diploids, the marker genotype for the above mutant wap7.1 allele (underlying the W1054STOP change of the protein in watermelon) is 'AA' when the mutant allele is in homozygous form. In triploids or tetraploids the marker genotype can be used to determine copy number of the mutant allele. The genotype may thus for example be AAA if three copies are present in a triploid, or AAAA if for copies are present in a tetraploid, or AAG if two copies are present in a triploid, etc.

Plants and Plant Parts

In one embodiment a cultivated watermelon plant is provided, or a part thereof (such as a cell, a tissue, organ, fruit, etc.), comprising at least one copy of a mutant allele of a gene named WAP7.1, said mutant allele conferring facultative parthenocarpy when the mutant allele is in homozygous form.

In one aspect the mutant allele is a mutant allele of the watermelon gene which encodes the WAP7.1 protein of SEQ ID NO: 1 or a protein comprising at least 94%, 95%, 96%, 97% or 98% sequence identity to SEQ ID NO: 1 (wild type functional protein), whereby the mutant allele has a reduced expression or no expression, or whereby the mutant allele encodes a mutant WAP7.1 protein comprising one or more amino acids replaced, inserted and/or deleted compared to the wild type protein.

In one embodiment the one or more amino acid replacements, insertions or deletions comprise or consist of the replacement, insertion or deletion of one or more amino acids in one or more of the four conserved domains. The mutant protein has a reduced-function or loss-of-function compared to the wild type protein (and thus compared to a wild type plant comprising the wild type WAP7.1 gene), preferably the plant cell or plant comprising the mutant allele in homozygous form is facultative parthenocarpic.

When referring herein to a specific nucleotide or amino acid position, e.g. at amino acid 1054 of SEQ ID NO: 1, "or at amino acid 1054 of a sequence comprising at least 94%, 95%, 96%, 97%, 98% or 99% sequence identity to the SEQ ID NO" (or 'at the equivalent position in a sequence comprising at least 94% . . . '), this means that the nucleotide or amino acid is present in a variant sequence at a nucleotide or amino acid corresponding to the same nucleotide or amino acid (e.g. corresponding to amino acid 1054 of SEQ ID NO: 1) in the variant sequence, i.e. in a sequence comprising at least 94%, 95%, 96%, 97%, 98% or 99% sequence identity to the mentioned SEQ ID NO. It may for example be that the variant sequence is one or a few nucleotides or amino acids shorter, but when one pairwise aligns the variant sequence with the mentioned SEQ ID NO, one can see which nucleotide or amino acid of the variant sequence corresponds to the same nucleotide or amino acid. In the variant sequence this may for example be amino acid 1045 in SEQ ID NO: 8 or amino acid 1082 in SEQ ID NO; 9, which corresponds to amino acid 1054 of SEQ ID NO: 1 (see FIG. 3).

The mutant allele is a mutation in an endogenous gene of cultivated watermelon. The existence of a gene conferring facultative parthenocarpy enables the skilled person to generate other de novo mutants in the gene, e.g. in any cultivated line or variety.

The skilled person can, without undue burden, generate plants according to the invention, e.g. by carrying out a method for generation and/or identification of WAP7.1 mutants in a mutant population or by targeted gene editing of the WAP7.1 gene.

As mentioned above, as the WAP7.1 gene has been identified to be the gene encoding a protein of SEQ ID NO: 1 (wild type watermelon protein) in normal, non-parthenocarpic watermelon plants, the same or other mutants than the ones generated by the inventors can be generated de novo.

As natural variation may exist in the wild type, functional WAP7.1 proteins, the wild type WAP7.1 protein need not be 100% identical to the protein of SEQ ID NO: 1 but may have less sequence identity to SEQ ID NO: 1, e.g. at least 94%, 95% 96%, 97%, 98%, 99% or 99.5% or 99.6%, 99.7%, 99.8% or 99.9% when aligned pairwise over the entire length to SEQ ID NO: 1. In one aspect the conserved Zn-binding domain, and/or the conserved Peptide Binding Domain, and/or the conserved Plus3 domain, and/or the conserved Proline Binding domain is however 100% identical to that of SEQ ID NO: 1, so that the variation of at least 94% identity lies outside of the one or more or all of the conserved domains. In another aspect the variation of at least 94% sequence identity in the functional wild type proteins of SEQ ID NO: 1 lies in between the 3Plus domain and the Proline binding motif and/or after the Proline binding motif (in the C-terminal part of the protein).

As mentioned, a mutant allele of a WAP7.1 protein-encoding gene causes a plant to produce seedless fruits in the absence of pollination and seeded fruits in the presence of pollination, when the plant is homozygous for the mutant allele, especially a diploid plant homozygous for the mutant allele and optionally a triploid plant comprising at least one, two or three copies of the mutant allele or a tetraploid plant comprising at least two or four copies of the mutant allele. Concerning the embodiments of the invention, the mutation in the mutant allele of a WAP7.1 protein-encoding gene can be any mutation, including deletions, truncations, insertions, point mutations, nonsense mutations, missense or non-synonymous mutations, splice-site mutations, frame shift mutations and/or mutations in regulatory sequences. In one aspect the mutation in the mutant allele of a WAP7.1 protein-encoding gene is a point mutation. The mutation can occur in a DNA sequence comprising the coding sequence of a WAP7.1 protein-encoding gene or in an RNA sequence encoding a WAP7.1 protein or it can occur in the amino acid of a WAP7.1 protein. Concerning a DNA sequence of a WAP7.1 protein-encoding gene the mutation can occur in the coding sequence or it can occur in non-coding sequences like 5'- and 3'-untranslated regions, promoters, enhancers etc. of a WAP7.1 protein-encoding gene. In respect to RNA encoding a WAP7.1 protein the mutation can occur in the pre-mRNA or the mRNA. In one aspect the mutant allele results in the protein having a loss-of-function or decrease of function due to one or more amino acids being replaced, inserted and/or deleted, for example resulting in one or more amino acids being replaced, inserted and/or deleted at the C-terminal end of the protein or in one or more of the conserved domains of the protein. For example, truncation of the protein to cause deletion of at least 10, 15, 20, 25, 30, 40, 50, 100, 150, 200 or more amino acids of the C-terminal end of the wild type protein will result in a mutant protein which causes facultative parthenocarpy, as was shown by the W1054STOP mutant protein.

Similarly, mutations whereby any of the conserved domains are deleted all or in part or are replaced by one or more different amino acids, will result in a loss of function or decrease of function of the protein.

For example a stop codon mutation e.g. in the N-terminal part preceding any of the conserved domains or in one of the conserved domains results in a truncated protein having a reduced function or loss of function.

Likewise amino acid insertions, deletions or replacements in the N-terminal part preceding any of the conserved domains or in one of the conserved domains can result in a protein having a reduced function or loss of function.

Any mutant allele can be analysed for the phenotype when the allele is in homozygous form in e.g. diploid plants, to see if indeed the plant becomes facultative parthenocarp.

One embodiment of the invention, therefore, concerns plant cells or plants according to the invention comprising a mutant allele of a WAP7.1 protein-encoding gene characterized in that the mutant allele comprises or effects one or more of the mutations selected from the group consisting of a) a deletion, truncation, insertion, point mutation, nonsense mutation, missense or non-synonymous mutation, splice-site mutation, frame shift mutation in the genomic sequence;

b) a mutation in one or more regulatory sequences;

c) a deletion, truncation, insertion, point mutation, nonsense mutation, missense or non-synonymous mutation, splice-site mutation, frame shift mutation in the coding sequence;

d) a deletion, truncation, insertion, point mutation, nonsense mutation, missense or non-synonymous mutation, splice-site mutation, frame shift mutation in the pre-mRNA or mRNA; and/or e) a deletion, truncation, insertion or replacement of one or more amino acids in the WAP7.1 protein.

In one aspect the mutant allele results in reduced expression or no expression of the WAP7.1 gene or the mutant allele encodes a protein having a decreased function or a loss-of-function.

Reduced expression or no expression means that there is a mutation in a regulatory region of the WAP7.1 gene, such as the promoter, whereby reduced mRNA transcript or no mRNA transcript of the WAP7.1 allele is being made, compared to plants and plant parts comprising a wild type WAP7.1 allele. The decrease in the expression can, for example, be determined by measuring the quantity of mRNA transcripts encoding WAP7.1 protein, e.g. using Northern blot analysis or RT-PCR. Here, a reduction preferably means a reduction in the amount of RNA transcripts by at least 50%, in particular by at least 70%, optionally by at least 85% or by at least 95%, or even by 100% (no expression) compared to the plant or plant part comprising a wild type WAP7.1 gene. Expression can be analysed e.g. in young leaf tissue or ovary tissue.

In one aspect the protein comprising one or more amino acids replaced, inserted or deleted compared to the wild type protein. Thus, for watermelon, one or more amino acids are inserted, deleted or replaced compared to the wild type WAP7.1 protein of SEQ ID NO: 1 or a wild type WAP7.1 protein comprising at least 94%, 95%, 96%, 97% or 98% sequence identity to SEQ ID NO: 1; whereby the mutant protein has reduced function or loss of function compared to the wild type protein and thus results in facultative parthenocarpy when the mutant allele is present in homozygous form in a diploid plant.

In one aspect the wild type WAP7.1 protein comprises the conserved Zn-binding domain. Thus in one aspect the mutant allele is a mutant allele of the gene WAP7.1, which gene encodes a wild type protein of SEQ ID NO: 1 (watermelon) or a wild type protein comprising at least 94%, 95%, 96%, 97% or 98% sequence identity to SEQ ID NO: 1, and whereby the wild type protein comprises the conserved Zn-binding domain of amino acids 114 to 159 of SEQ ID NO: 1.

In one aspect the wild type WAP7.1 protein comprises the conserved Peptide Binding domain. Thus in one aspect the mutant allele is a mutant allele of the gene WAP7.1, which gene encodes a wild type protein of SEQ ID NO: 1 (watermelon) or a wild type protein comprising at least 94%, 95%, 96%, 97% or 98% sequence identity to SEQ ID NO: 1, and whereby the wild type protein comprises the conserved Peptide Binding domain of amino acids 350 to 395 of SEQ ID NO: 1.

In one aspect the wild type WAP7.1 protein comprises the conserved Plus3 domain. Thus in one aspect the mutant allele is a mutant allele of the gene WAP7.1, which gene encodes a wild type protein of SEQ ID NO: 1 (watermelon) or a wild type protein comprising at least 94%, 95%, 96%, 97% or 98% sequence identity to SEQ ID NO: 1, and whereby the wild type protein comprises the conserved Plus3 domain of amino acids 464 to 572 of SEQ ID NO: 1.

In one aspect the wild type WAP7.1 protein comprises the conserved Proline Binding motif. Thus in one aspect the mutant allele is a mutant allele of the gene WAP7.1, which gene encodes a wild type protein of SEQ ID NO: 1 (watermelon) or a wild type protein comprising at least 94%, 95%, 96%, 97% or 98% sequence identity to SEQ ID NO: 1, and whereby the wild type protein comprises the conserved Proline Binding motif of amino acids 812 to 828 of SEQ ID NO: 1.

In one aspect the wild type WAP7.1 protein comprises the conserved Zn binding domain and the Peptide binding domain and the Plus3 domain and the Proline Binding Motif, i.e. any variation of the functional wild type protein is outside these conserved domains.

The mutant alleles of the above wild type alleles are in one aspect mutant alleles having reduced expression or no expression (through e.g. mutations in the promoter or enhancer elements) or producing a mutant protein which comprises one or more amino acids inserted, deleted or replaced compared to the wild type protein, whereby the mutant protein has a reduced function or no function in vivo, as can be determined when the mutant allele is in homozygous form in a plant and by analysing whether the plant produces fruits in the absence of pollination (parthenocarpy), e.g. when grown in an insect free environment and the (female) flowers produce fruits despite not being pollinated. Also, plants can be tested as to whether they produce normal, seeded fruits when the (female) flowers are pollinated. If the mutant allele causes facultative parthenocarpy in vivo, while the control plant comprising only the wild type WAP7.1 alleles is not facultative parthenocarp, then the mutant protein has a reduced function or no function compared to the wild type protein. The same phenotypic analysis can be done for a mutant allele having reduced gene expression or no gene expression. Thus, any mutant allele can be made homozygous in the plant and the phenotype can be compared to the control plant comprising the original, non-mutated allele.

The Zn-binding domain, the Peptide Binding domain, the Plus3 domain and the Proline Binding motif were found to be conserved protein domains, which most likely will be 100% identical in other wild type, functional WAP7.1 variants also, as they will be required for proper functioning of the protein in the plant. Therefore, mutating one or more of these conserved domains by inserting, deleting or replacing one or more of its amino acids will reduce or abolish the WAP7.1 protein function in vivo.

In one aspect, therefore, a plant provided herein comprises a mutant WAP7.1 allele which encodes a WAP7.1 protein comprising one or more amino acids inserted, deleted or replaced in the Zn-binding domain, the Peptide Binding domain, the Plus3 domain and/or the Proline Binding motif.

The wild type, functional WAP7.1 protein which is mutated to comprise one or more amino acids inserted, replaced or deleted is selected from ClWAP7.1 of SEQ ID NO: 1 or a protein comprising at least 94% identity to SEQ ID NO: 1, whereby the wild type protein comprises the Zn-binding domain, the Peptide Binding domain, the Plus3 domain and/or the Proline Binding motif of SEQ ID NO: 1.

A mutant protein comprising a frame shift leading to a change of one or more amino acids in any one of the conserved domains or a mutant protein comprising a truncation leading to the deletion of one or more amino acids of any one of the conserved domains is hereby encompassed as being a mutant protein comprising reduced function or no function in vivo.

In one aspect therefore a mutant ClWAP7.1 allele is provided encoding a mutant protein wherein the W1054 of SEQ ID NO: 1 (or a sequence comprising at least 94% identity to SEQ ID NO: 1), is replaced by another amino acid or is deleted, e.g. the codon being replaced by a STOP codon.

In one aspect therefore a mutant ClWAP7.1 allele is provided encoding a mutant protein wherein the R346 of SEQ ID NO: 1 (or a sequence comprising at least 94% identity to SEQ ID NO: 1), is replaced by another amino acid or is deleted, e.g. the codon being replaced by a STOP codon.

In one aspect therefore a mutant ClWAP7.1 allele is provided encoding a mutant protein wherein the S324 of SEQ ID NO: 1 (or a sequence comprising at least 94% identity to SEQ ID NO: 1), is replaced by another amino acid or is deleted, e.g. the codon being replaced by a STOP codon.

In one aspect therefore a mutant ClWAP7.1 allele is provided encoding a mutant protein wherein the P830 of SEQ ID NO: 1 (or a sequence comprising at least 94% identity to SEQ ID NO: 1), is replaced by another amino acid or is deleted, e.g. the codon being replaced by a STOP codon.

In one aspect therefore a mutant ClWAP7.1 allele is provided encoding a mutant protein wherein the A328 of SEQ ID NO: 1 (or a sequence comprising at least 94% identity to SEQ ID NO: 1), is replaced by another amino acid or is deleted, e.g. the codon being replaced by a STOP codon.

In one aspect therefore a mutant ClWAP7.1 allele is provided encoding a mutant protein wherein the Q373 of SEQ ID NO: 1 (or a sequence comprising at least 94% identity to SEQ ID NO: 1), is replaced by another amino acid or is deleted, e.g. the codon being replaced by a STOP codon.

When amino acids from one amino acid to another amino acid are mentioned herein this includes the start/first and end/last amino acid mentioned.

When referring to an amino acid being 'deleted', this includes a mutation whereby the codon is changed into a stop codon, or the codon is deleted, or a mutation whereby there is a frameshift, resulting in the amino acid not be encoded. Equally, when referring to an amino acid being 'replaced', this includes a mutation whereby the codon encodes a different amino acid, or a codon is inserted, or a mutation whereby there is a frameshift resulting in a different amino acid being encoded.

The plants and plant parts comprising at least one copy of a mutant wap7.1 allele may be plants of the family Cucurbitaceae, especially cultivated species such as watermelon (*Citrullus lanatus*). Also plants and plant parts of the family Cucurbitaceae, especially watermelon, comprising two copies of a mutant wap7.1 allele are encompassed herein, whereby diploid plants comprising two copies of the mutant wap7.1 allele results in plants exhibiting the phenotype of facultative parthenocarpy.

In one aspect the mutant wap7.1 allele is heterozygous in a diploid plant cell or plant, e.g. in a diploid watermelon plant. In another aspect the mutant wap7.1 allele is homozygous in a diploid plant cell or plant.

The plant cells and plants are preferably cultivated plants, such as elite breeding lines or varieties, and not wild plants. Watermelon may be any type of watermelon.

Watermelon plants, and parts thereof, which comprises at least one copy of the mutant wap7.1 allele, may be diploid, tetraploid or triploid. In another aspect it may be another polyploid, e.g. a pentaploid, hexaploid, heptaploid, octaploid, etc. A tetraploid plant comprising four copies of wap7.1 can for example be used to make an octaploid, by doubling the chromosomes. Crossing such an octoploid with a diploid homozygous for wap7.1 will result in a pentaploid comprising five copies of wap7.1. In one aspect the polyploidy watermelon plant comprises at least one copy of the mutant wap7.1 allele, but it may also comprise more copies, e.g. in a preferred aspect a triploid plant comprises two or three copies of a mutant wap7.1 allele or a tetraploid comprises two or four copies of a mutant wap7.1 allele.

A diploid plant may thus have the genotype wap7.1/WAP7.1 (heterozygous for the mutant allele) or wap7.1/wap7.1 (homozygous for the mutant allele). In one aspect the diploid plant comprising the wap7.1 allele in homozygous form is a double haploid plant (DH), e.g. a double haploid watermelon, plant or plant cell or plant part. DH plants can be made by chromosome doubling (e.g. through colchicine treatment) of haploid cells.

A triploid watermelon plant may have the genotype wap7.1/WAP7.1/WAP7.1 or wap7.1/wap7.1/WAP7.1 or wap7.1/wap7.1/wap7.1. The triploid plant with genotype wap7.1/WAP7.1/WAP7.1 can be made by crossing a wild type female tetraploid (WAP7.1/WAP7.1 WAP7.1/WAP7.1) with a diploid male homozygous for the mutant allele (wap7.1/wap7.1). The triploid plant with genotype wap7.1/wap7.1/WAP7.1 can be made by crossing a female tetraploid (wap7.1/wap7.1/wap7.1/wap7.1) with a diploid male homozygous for the wild type allele (WAP7.1/WAP7.1).

A tetraploid watermelon plant may have the genotype wap7.1/WAP7.1/WAP7.1/WAP7.1 or wap7.1/wap7.1/WAP7.1/WAP7.1 or wap7.1/wap7.1/wap7.1/WAP7.1 or wap7.1/wap7.1/wap7.1/wap7.1. The genotypes wap7.1/wap7.1/WAP7.1/WAP7.1 can be made by doubling the chromosomes of a diploid wap7.1/WAP7.1. The genotypes wap7.1/wap7.1/wap7.1/wap7.1 can be made by doubling the chromosomes of a diploid wap7.1/wap7.1. The other two genotypes, wap7.1/WAP7.1/WAP7.1/WAP7.1 and wap7.1/wap7.1/wap7.1/WAP7.1 can for example be made by crossing two tetraploids of genotype wap7.1/wap7.1/WAP7.1/WAP7.1 and identifying the genotypes in the progeny.

In one aspect the watermelon plant is homozygous for wap7.1, in another aspect it is heterozygous for wap7.1. In one aspect it is an inbred line or a variety. In a further aspect it is an F1 hybrid.

Seeds from which any of the watermelon plants described can be grown are also encompassed herein, as are parts of such a plant, such as seedless fruits produced in the absence of pollination, flowers, cells, roots, rootstocks, scions, leaves, stems, vegetative propagations, cuttings, seed propagations (e.g. selfings) and also in vitro cell- or tissue cultures, as well as pollen, ovaries, etc. are encompassed herein.

Diploid Watermelon Plants Comprising a Mutant Wap7.1 Allele

In one aspect the watermelon plant is a diploid line (e.g. an inbred line) or variety, comprising at least one mutant copy of wap7.1, preferably two mutant copies (i.e. is homozygous for wap7.1). When preventing pollination of the female flowers, the diploid plant homozygous for wap7.1 will produce fruits which are seedless. When pollination does occur, the fruits will be seeded.

To prevent pollination one can, for example, grow the plant in an insect free environment. However, one can also produce a diploid plant which is male sterile. Thus, in one aspect of the invention a diploid plant is provided which is homozygous for wap7.1, and which additionally is male sterile. Male sterility is the failure of plants to produce functional anthers, pollen, or male gametes. Several male sterility genes have been identified in watermelon, including the ms-1 gene. The ms-1 nuclear gene controls male sterility and, in plants with an ms-1 gene in homozygous form (ms-1 is recessive), the normal development of anthers is hindered while female flower development is normal. The gene eliminates pollen production. Markers for the ms-1 gene and plants comprising the gene are described in EP2959771 and the database PINTO mentions that variety Bonta or Bonta F1 of *Seminis* is a plant according to this patent. The ms-1 gene has also been described in Zhang et al. 1996 (HortScience 31(1): 123-126). The ms-1 gene is on chromosome 6 of watermelon and can therefore easily be combined with wap7.1 on chromosome 7.

Therefore, in one aspect the diploid plant and plant part according to the invention is male sterile and/or comprises a male sterility gene. If the male sterility gene is a recessive gene, the plant and plant part preferably comprises the gene in homozygous form. In one aspect the watermelon plant comprises the ms-1 gene, preferably in homozygous form. Thus, in one aspect the diploid watermelon plant comprises on chromosome 7 the mutant wap7.1 gene in homozygous form (wap7.1 wap7.1) and further comprises a male sterility gene, e.g. ms-1, in homozygous form, e.g. if the male sterility gene is recessive (e.g. ms-1/ms-1) or optionally in heterozygous form if the male sterility is dominant. One preferred plant is a diploid plant homozygous for wap7.1 and homozygous for ms-1.

A further way of ensuring that plants according to the invention, especially diploid watermelon plants, produce seedless fruits at all times (not only in the absence of pollination) is to combine the wap7.1 gene in homozygous form with a gene conferring stenospermocarpy, so that if pollination does occur the fruits will be seedless despite pollination. In one aspect the stenospermocarpy gene is the recessive gene called emb. The wild type and mutant Emb1 gene has been described in co-pending application EP16171462.1. The Emb1 gene encodes a cyclin SDS like protein. When the mutant allele emb1 is in homozygous form, stenospermocarpy results. "Stenospermocarpy" means that induction of fruit set and development requires pollination but without the fruits producing mature or viable seeds. Mature or viable seeds are not developed in stenospermocarpic plants due to arrested seed development or degradation of ovules and/or embryos and/or endosperm or abortion of the ovules and/or embryos and/or endosperm before maturity is reached. Thus, when diploid plants homozygous for a mutant emb1 allele (emb1/emb1) are self-pollinated or pollinated by pollen from another plant, they produced seedless, diploid fruits.

Thus, in one aspect the diploid watermelon plant comprises on chromosome 7 the wap7.1 gene in homozygous form (wap7.1/wap7.1) and further comprises a stenospermocarpy gene, e.g. emb1, in homozygous form, e.g. if the stenospermocarpy gene is recessive (e.g. emb1/emb1) or optionally in heterozygous form if the stenospermocarpy gene is dominant. One preferred plant is a diploid plant homozygous for wap7.1 and homozygous for emb1.

One mutant allele of emb1 can be obtained from the watermelon seeds being heterozygous or homozygous for the mutant allele of the cyclin SDS like protein encoding gene (also referred to as Emb1 gene), deposited by Nunhems B. V. under NCIMB 42532. Of these seeds 25% contain the mutant allele (see mRNA of SEQ ID NO: 27) encoding a mutant protein of SEQ ID NO: 28. The wild type allele of the Emb1 gene can be obtained from the watermelon seeds being heterozygous or homozygous for the wild type cyclin SDS like protein encoding gene, deposited by Nunhems B. V. under NCIMB 42532. Of these seeds 25% contain the wild type allele of SEQ ID NO: 25 in homozygous form, encoding the wild type protein of SEQ ID NO: 26. Other mutant alleles of the Emb1 gene can be generated de novo, e.g. by mutagenesis or by other methods known to the skilled person. The genomic Emb1 nucleotide sequence shown under SEQ ID NO: 25 encodes a wild type cyclin SDS like protein of *Citrullus lanatus* having the amino acid sequence as shown under SEQ ID NO: 26. The mRNA sequence shown under SEQ ID NO: 27, and the mutant protein shown under SEQ ID NO: 28, is of the mutant emb1 allele found in seeds deposited under NCIMB42532.

A mutant allele of emb1 causes a plant to be male fertile but producing seedless fruits, when the plant is homozygous for the mutant allele. The mutation in the Emb1 gene can be any mutation, including deletions, truncations, insertions, point mutations, nonsense mutations, missense or non-syn-onymous mutations, splice-site mutations, frame shift muta-tions and/or mutations in regulatory sequences. Preferably the mutation is a point mutation and/or splice-site mutation. The mutation can occur in a DNA sequence comprising the coding sequence of a cyclin SDS like protein encoding gene (Emb1 gene) or in a RNA sequence encoding a cyclin SDS like protein or it can occur in the amino acid of a cyclin SDS like protein (or Emb1 protein). Concerning a DNA sequence of a cyclin SDS like protein encoding gene the mutation can occur in the coding sequence (cds, composed of the exons) or it can occur in non-coding sequences like 5'- and 3'-un-translated regions, introns, promoters, enhancers etc. of a cyclin SDS like protein encoding gene. In respect to RNA encoding a cyclin SDS like protein the mutation can occur in the pre-mRNA or the mRNA.

Diploid *Citrullus lanatus* seeds of plants segregating for a mutant allele of a cyclin SDS like protein encoding gene have been deposited by Nunhems B. V. under the Budapest Treaty under accession No. NCIMB 42532 at NCIMB Ltd., Ferguson Building, Craibstone Estate Bucksburn Aberdeen AB21 9YA, Scotland, UK on 27 Jan. 2016. For the seed deposit the allele of the cyclin SDS like protein encoding gene was designated emb1.

The deposited seeds were obtained from a self-pollinated back-cross of a plant homozygous for the emb1 mutant allele with plants homozygous for the emb1 wild type allele. Therefore 25% of the deposited seeds are homozygous for the emb1 mutant allele and produce seedless fruits, 50% are heterozygous for the mutant allele and 25% are homozygous for the wild type allele, encoding the wild type cyclin SDS like protein.

In one aspect the invention, therefore, relates to a diploid watermelon plant or plant part comprising at least one copy of the mutant wap7.1 allele, preferably two copies, and at least one copy of a mutant emb1 allele, preferably two copies of a mutant emb1 allele. In one aspect the mutant emb1 allele is the allele found in seeds deposited under NCIMB 42532.

Seeds from which such a diploid plant can be grown are also encompassed herein, as are parts of such a plant, such as diploid seedless fruits, flowers, leaves, stems, vegetative propagations, cells, cuttings, seed propagations (e.g. self-ings) and also in vitro cell- or tissue cultures, as well as pollen, ovaries, rootstocks, scions, etc. are encompassed herein. Thus, in one embodiment the diploid plant, or seeds from which the plant can be grown, or tissue or parts of the plant (pollen, anthers, ovules) comprises a mutant wap7.1 allele as described above or a different mutant wap7.1 allele.

In one aspect the diploid plant comprises two copies of the mutant wap7.1 allele which encodes the truncated protein of SEQ ID NO: 2 due to STOP codon at amino acid 1054 of SEQ ID NO: 1, or which encodes a truncated protein comprising a STOP codon at the equivalent amino acid codon in a sequence comprising at least 94%, 95%, 96%, 97%, 98% or 99% sequence identity to SEQ ID NO: 1.

In one aspect the diploid plant comprises two copies of the mutant wap7.1 allele which encodes the truncated protein of SEQ ID NO: 10 due to STOP codon at amino acid 373 of SEQ ID NO: 1, or which encodes a truncated protein comprising a STOP codon at the equivalent amino acid codon in a sequence comprising at least 94%, 95%, 96%, 97%, 98% or 99% sequence identity to SEQ ID NO: 1.

In one aspect the diploid plant comprises two copies of the mutant wap7.1 allele which encodes the mutant protein of SEQ ID NO: 11 comprising a K at amino acid 346, or which encodes the mutant protein comprising a K at the equivalent position in a sequence comprising at least 94%, 95%, 96%, 97%, 98% or 99% sequence identity to SEQ ID NO: 11.

In one aspect the diploid plant comprises two copies of the mutant wap7.1 allele which encodes the mutant protein of SEQ ID NO: 12 comprising a N at amino acid 324, or which encodes the mutant protein comprising a N at the equivalent position in a sequence comprising at least 94%, 95%, 96%, 97%, 98% or 99% sequence identity to SEQ ID NO: 12.

In one aspect the diploid plant comprises two copies of the mutant wap7.1 allele which encodes the mutant protein of SEQ ID NO: 13 comprising a S at amino acid 830, or which encodes the mutant protein comprising a S at the equivalent position in a sequence comprising at least 94%, 95%, 96%, 97%, 98% or 99% sequence identity to SEQ ID NO: 13.

In one aspect the diploid plant comprises two copies of the mutant wap7.1 allele which encodes the mutant protein of SEQ ID NO: 14 comprising a T at amino acid 328, or which encodes the mutant protein comprising a T at the equivalent position in a sequence comprising at least 94%, 95%, 96%, 97%, 98% or 99% sequence identity to SEQ ID NO: 14.

In one aspect the diploid plant comprises two copies of the mutant wap7.1 allele which encodes a mutant protein of Table 1.

In one aspect the diploid plant comprises two copies of the mutant wap7.1 allele of SEQ ID NO: 7.

Tetraploid Watermelon Plants Comprising a Mutant Wap7.1 Allele

Seedless triploid watermelon production involves using pollen from diploid male parent plants to fertilize flowers of tetraploid maternal parent plants. Pollination of the tet-raploid flowers with diploid pollen leads to F1 seeds which are triploid (Kihara, 1951, Proceedings of American Society for Horticultural Science 58: 217-230; Eigsti 1971, Hort Science 6: 1-2). The triploid hybrid plants, grown from these F1 seeds, are self-infertile as they produce sterile pollen due to chromosome imbalance. The triploid hybrids, therefore, normally need to be pollinated by a diploid pollenizer to produce watermelon fruit.

However, according to the present invention a triploid plant comprising one, two or three copies of a mutant wap7.1 gene produce fruits without pollination and there is no need anymore for a pollenizer plant being present. Therefore, a method for growing such triploid watermelon plants e.g. in a field, in the absence of pollenizer plants and/or in the absence of (fertile) pollen is encompassed herein, in order to produce seedless fruits.

In one aspect of the invention therefore both tetraploid plants, comprising preferably four copies of a recessive wap7.1 allele, for use as a female parent, and diploid plants comprising preferably two copies of a recessive wap7.1 allele, for use as a male parent, are provided, as well as triploid F1 hybrids (comprising preferably three copies of a mutant wap7.1 allele) produced by crossing the diploid male parent with the tetraploid female parent.

To make such a tetraploid plant, any of the diploid plants described above, which are preferably homozygous for wap7.1, may be used as starting material to generate tet-raploid plants. Chromosome doubling techniques known to the skilled person may be used to generate a tetraploid plant from such diploid plants. For example Noh et al. (2012) Hort. Environ. Biotechnol. 53(6):521-529, evaluated differ-ent methods of generating tetraploid watermelons. In all methods an antimitotic agent is used, such as colchicine, dinitoalanine, or oryzalin, in order to induce chromosome doubling. Optionally tissue culture may be used to generate tetraploid plants from plant parts. To verify that plants are tetraploid chromosome number can be confirmed. Ploidy can be easily determined by chromosome counting or flow cytometry or other known methods (Sari et al. 1999, Scientia Horticulturae 82: 265-277, incorporated herein by reference).

Thus, in one aspect of the invention a tetraploid cultivated watermelon plant of the species *Citrullus lanatus* is provided, wherein said plant comprises two or preferably four copies of a mutant wap7.1 allele (as described above), one on each of the four chromosomes 7.

All embodiments described for the mutant wap7.1 allele above apply equally to the tetraploid. So for example the tetraploid plant may comprise four copies of a wap7.1 allele described, or four copies of a different mutant wap7.1 allele as described further above.

Thus, in one aspect the invention encompasses a tetraploid watermelon plant or plant part comprising one, two, three or four copies of a mutant allele of a gene named WAP7.1 encoding a protein of SEQ ID NO: 1, or a protein comprising at least 94%, 95%, 96%, 97% or 98% sequence identity to SEQ ID NO: 1. The aspects regarding the mutant wap7.1 allele described above for diploid watermelon plants comprising one or two copies of a mutant wap7.1 allele apply to the tetraploid plants and plant parts. So, for example, in one aspect the mutant allele results in reduced expression or no expression of the WAP7.1 gene or the mutant allele encodes a mutant WAP7.1 protein having a decreased function or a loss-of-function.

In one aspect the tetraploid plant comprises two or preferably four copies of the mutant wap7.1 allele which encodes the mutant protein of SEQ ID NO: 2.

In one aspect the tetraploid plant comprises two or preferably four copies of the mutant wap7.1 allele which encodes the truncated protein of SEQ ID NO: 2 due to STOP codon at amino acid 1054 of SEQ ID NO: 1, or which encodes a truncated protein comprising a STOP codon at the equivalent amino acid codon in a sequence comprising at least 94%, 95%, 96%, 97%, 98% or 99% sequence identity to SEQ ID NO: 1.

In one aspect the tetraploid plant comprises two or preferably four copies of the mutant wap7.1 allele which encodes the truncated protein of SEQ ID NO: 10 due to STOP codon at amino acid 373 of SEQ ID NO: 1, or which encodes a truncated protein comprising a STOP codon at the equivalent amino acid codon in a sequence comprising at least 94%, 95%, 96%, 97%, 98% or 99% sequence identity to SEQ ID NO: 1.

In one aspect the tetraploid plant comprises two or preferably four copies of the mutant wap7.1 allele which encodes the mutant protein of SEQ ID NO: 11 comprising a K at amino acid 346, or which encodes the mutant protein comprising a K at the equivalent position in a sequence comprising at least 94%, 95%, 96%, 97%, 98% or 99% sequence identity to SEQ ID NO: 11.

In one aspect the tetraploid plant comprises two or preferably four copies of the mutant wap7.1 allele which encodes the mutant protein of SEQ ID NO: 12 comprising a N at amino acid 324, or which encodes the mutant protein comprising a N at the equivalent position in a sequence comprising at least 94%, 95%, 96%, 97%, 98% or 99% sequence identity to SEQ ID NO: 12.

In one aspect the tetraploid plant comprises two or preferably four copies of the mutant wap7.1 allele which encodes the mutant protein of SEQ ID NO: 13 comprising a S at amino acid 830, or which encodes the mutant protein comprising a S at the equivalent position in a sequence comprising at least 94%, 95%, 96%, 97%, 98% or 99% sequence identity to SEQ ID NO: 13.

In one aspect the tetraploid plant comprises two or preferably four copies of the mutant wap7.1 allele which encodes the mutant protein of SEQ ID NO: 14 comprising a T at amino acid 328, or which encodes the mutant protein comprising a T at the equivalent position in a sequence comprising at least 94%, 95%, 96%, 97%, 98% or 99% sequence identity to SEQ ID NO: 14.

In another aspect the tetraploid plant comprises two or four copies of a mutant wap7.1 allele which encodes a mutant protein of Table 1.

In one aspect the tetraploid plant comprises two or preferably four copies of the mutant wap7.1 allele of SEQ ID NO: 7.

Genotyping of tetraploid plants or plant parts (cells, leaves, DNA, etc.) can be done in the same way as for diploids, using for example a KASP-assay to distinguish SNP genotypes, e.g. plants or parts comprising AAAA for the marker mWM23348403 at nucleotide 51 of SEQ ID NO: 5 (detecting four mutant wap7.1 alleles encoding the protein of SEQ ID NO: 2, comprising the W1054STOP mutation) can be distinguished from plants or parts comprising GAAA (detecting three mutant alleles encoding the protein of SEQ ID NO: 2), GGAA (detecting two mutant alleles encoding the protein of SEQ ID NO: 2), GGGA (detecting one mutant allele encoding the protein of SEQ ID NO 2) or GGGG (detecting four wild type alleles encoding the protein of SEQ ID NO: 1) for the mWM23348403 at nucleotide 51 of SEQ ID NO: 5 in their genome. The same applies for other allele-specific markers, such as e.g. SNP markers of Table 1.

In one aspect of the invention a tetraploid watermelon comprising at least one or two or three copies of the mutant wap7.1 allele (as described above), but preferably comprising four copies of the mutant wap7.1 allele (as described above) is provided. Preferably the watermelon plant is a tetraploid inbred female line, suitable as a parent for F1 hybrid seed production.

The generation of the tetraploid female inbred line can be carried out by using a diploid plant, comprising one or preferably two copies of the wap7.1 allele in order to double the chromosomes and generate a tetraploid plant. E.g. a diploid inbred line homozygous for wap7.1 can be used to generate the tetraploid plant.

A tetraploid plant comprising four copies of a mutant wap7.1 allele will express the phenotype, i.e. be facultative parthenocarpic.

Seeds from which such a tetraploid plant can be grown are also encompassed herein, as are parts of such a plant, such as tetraploid seedless fruits produced in the absence of pollination, flowers, leaves, stems, cuttings, vegetative propagations, cells, seed propagations (e.g. selfings) and also in vitro cell- or tissue cultures, as well as pollen, ovaries, rootstocks, scions, etc. are encompassed herein. Thus, in one embodiment the tetraploid plant, or seeds from which the plant can be grown, or tissue or parts of the plant (pollen, anthers, ovules) comprises a mutant wap7.1 allele as described above.

A tetraploid can comprise different mutant wap7.1 alleles, e.g. two mutant wap7.1 alleles encoding a truncated WAP7.1 protein and two mutant wap7.1 allele encoding a WAP7.1 protein having an amino acid substitution. Such plants can for example be made by first making a diploid comprising different mutant wap7.1 alleles and then doubling the chromosomes of such diploid. In one aspect the tetraploid does, however, comprise four copies of the same mutant wap7.1 allele, i.e. the tetraploid is made from a diploid which is homozygous for the wap7.1 allele.

Triploid Watermelon Plants Comprising a Mutant Wap7.1 Allele

In a further aspect triploid watermelon seeds, plants and plant parts comprising one, two or three copies of a mutant wap7.1 allele are provided, i.e. wap7.1/WAP7.1 WAP7.1 or wap7.1 wap7.1 WAP7.1 or wap7.1 wap7.1 wap7.1, respectively. Such triploids can be made as described above, and as shown in the Table 2 below:

TABLE 2

| | Female tetraploid parent | Male diploid parent | Genotype of F1 triploid seed produced by pollinating female tetraploid with pollen of male diploid |
|---|---|---|---|
| A | Wap7.1/wap7.1/wap7.1/wap7.1 | Wap7.1/wap7.1 | Wap7.1/wap7.1/wap7.1 |
| B | Wap7.1/wap7.1/wap7.1/wap7.1 | WAP7.1/WAP7.1 | Wap7.1/wap7.1/WAP7.1 |
| C | WAP7.1/WAP7.1/WAP7.1/WAP7.1 | Wap7.1/wap7.1 | WAP7.1/WAP7.1/wap7.1 |

In one aspect a tetraploid plant comprising four copies of a mutant wap7.1 allele is used as female parent and is pollinated with pollen of diploid male parent comprising two copies of a mutant wap7.1 allele and the seeds from the cross are harvested. These seeds are triploid and they comprise three copies of a mutant wap7.1 allele of the invention (Table 2, row A). Plants grown from these seeds produce seedless watermelon fruits (triploid fruits) without the need for pollination to induce fruit set. The triploid hybrid plants, grown from these F1 triploid seeds, are self-infertile as they produce sterile pollen due to chromosome imbalance. These seeds can thus be grown in production fields without the need for pollenizer plants. This is the first time that seedless triploid watermelon fruits can be produced in the absence of pollen and pollenizer plants.

In one aspect the triploid under A above comprises three identical mutant wap7.1 alleles, i.e. the female and male parents comprise the same mutant allele. However, in another aspect the female parent and the male parent may comprise different mutant wap7.1 alleles. For example the female parent may comprise four mutant wap7.1 allele encoding a truncated WAP7.1 protein and the male parent may comprise two mutant wap7.1 allele encoding a WAP7.1 protein having an amino acid substitution.

In one aspect the mutant wap7.1 allele conferring facultative parthenocarpy described herein is combined with another mutant allele conferring parthenocarpy, especially conferring facultative parthenocarpy. Such another mutant allele is for example the wop1 allele described in WO2018/060444, which is located on chromosome 4 (it is also referred to as wap4.1). In one aspect a mutant wap7.1 allele is combined with a mutant wop1 allele in diploid, triploid or tetraploid watermelon plants. As wop1 is on a different chromosome, one can make different combinations between wop1 and wap7.1, e.g. three mutant copies of each of wop1 and of wap7.1 in a triploid watermelon, or one or two mutant copy of wop1 and three mutant copies of wap7.1 in a triploid watermelon, or the other way around, etc.

The triploid, seedless fruits are preferably marketable. Preferably they have an average brix of at least 6.0, 7.0, 8.0 or preferably at least 9.0, preferably at least 10.0, more preferably at least 11.0. Fruits may be of any size, shape, color and rind pattern. Preferably fruit flesh color at maturity is uniform. In one aspect fruit flesh is red or dark red.

The average fruit weight of a triploid hybrid comprising wap7.1 in three copies may be equal to or above 2, 3, 4, 5, 6, 7, 8, 9, 10, 11, 12, 13 or 14 kg. In another embodiment average fruit weight of a triploid hybrid comprising wap7.1 in three copies may be equal to or less than 5 kg, e.g. 4, 3, 2, 1.5 or 1 kg or even less.

Seedless fruits may be of any shape (e.g. elongate, oval, blocky, spherical or round), fruit surface (furrow, smooth), flesh color (red, dark red, scarlet red, coral red, orange, salmon, pink, pinkish red, yellow, canary yellow or white), rind color (e.g. light green; dark green; green-striped with narrow, medium or wide stripes; grey types; with or without spotting; Golden yellow), rind thickness, rind toughness, rind pattern (e.g. striped, non-striped, netted), flesh structure/flesh firmness, lycopene and/or vitamin content, different sugar to acid ratios, fruit flavour, etc.

Thus, the mutant wap7.1 allele may be used to breed a range of seedless varieties, producing fruits of different shapes and sizes, etc. by traditional breeding. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar:acid ratio, good flavor, high vitamin and lycopene content, firm flesh texture, non-fibrous flesh texture, freedom from defects such as hollow heart, rind necrosis, blossom-end rot or cross stitch and good rind characteristics and cracking-resistance).

Seeds from which such triploid F1 hybrid plants can be grown are one aspect of the invention. Thus in one aspect a method for growing triploid watermelon plants/producing seedless watermelon fruits comprising the steps: seeding or planting triploid watermelon plants comprising one, two or three mutant wap7.1 alleles in their genome, optionally preventing pollination of the flowers (e.g. by male sterility, absence of pollenizers and/or absence of pollen) and harvesting the seedless watermelon fruits which develop in the absence of pollination through parthenocarpy. In principle, preventing pollination is not needed, as triploid fruits anyway produce seedless fruits. The difference is that triploids comprising the mutant wap7.1 allele(s) do not need pollen anymore to induce fruit development, so the cultivation area can be occupied entirely by triploid plants and interplanting of pollenizer plants is not needed anymore.

Also for diploid watermelon plants comprising two copies of a mutant wap7.1 allele a method of producing seedless fruits is provided. Thus in one aspect a method for growing diploid watermelon plants/producing seedless watermelon fruits comprising the steps: seeding or planting diploid watermelon plants comprising two copies of a mutant wap7.1 allele in their genome, preventing pollination of the flowers (e.g. by male sterility, absence of pollenizers and/or absence of pollen) and harvesting the seedless watermelon fruits which develop in the absence of pollination through parthenocarpy. For diploid cultivation it is necessary to prevent pollination of the female flowers, as the fruits will otherwise contain seeds. Pollination can be prevented by various means or combinations thereof, e.g. growing the plants in protected, pollen free environments, ensuring that the plants are male sterile and/or do not produce pollen, generating a time difference in pollen production and opening of female flowers, removing male flowers, etc.

Regarding triploid seeds and triploid plants comprising only one or two copies of a mutant wap7.1 allele of the invention (as shown in the Table 2 above, row B and C), the phenotype has not yet been tested, but these may also be suitable to produce seedless fruits without pollen and they may also be grown in a field without pollenizer plants. In any case, such triploid plants and seeds from which such plants can be grown are an aspect of the invention, as are parts thereof and triploid fruits produced by such plants. Preferably such triploid fruits are marketable. Preferably they have an average brix of at least 6.0, 7.0, 8.0 or preferably at least 9.0, preferably at least 10.0, more preferably at least 11.0. Fruits may be of any size, shape, color and rind pattern. Preferably fruit flesh color at maturity is uniform. In one aspect fruit flesh is red or dark red.

In one aspect the triploid plant of the invention is a vegetative propagation.

Also provided is a method for producing triploid hybrid watermelon seeds, wherein triploid plants grown from such seeds produce fruits in the absence of pollination, said method comprising:

(a) providing a facultative parthenocarpic diploid watermelon plant and a facultative parthenocarpic tetraploid plant (see e.g. Table 2 row A), (b) allowing pollination of pistillate flowers of the tetraploid plant with pollen of the diploid plant, and (c) harvesting seeds produced in the fruits of the tetraploid plant, and optionally (d) drying the harvested seeds.

Optionally the dried and harvested F1 seeds are then packaged. They may also be treated prior to packaging. Thus, packages or containers comprising or consisting of seeds obtained by the above method are an embodiment herein.

Also provided is a method for producing triploid hybrid watermelon seeds, said method comprising:

(a) providing a diploid watermelon plant lacking a mutant wap7.1 allele and a tetraploid plant comprising four copies of a mutant wap7.1 allele (see e.g. Table 2 row B), or providing a diploid watermelon plant homozygous for the mutant wap7.1 allele and a tetraploid plant lacking a mutant wap7.1 allele (e.g. Table 2 row C), (b) allowing pollination of pistillate flowers of the tetraploid plant with pollen of the diploid plant, and (c) harvesting seeds produced in the fruits of the tetraploid plant, and optionally (d) drying the harvested seeds.

Optionally the dried and harvested F1 seeds are then packaged. They may also be treated prior to packaging. Thus, packages or containers comprising or consisting of seeds obtained by the above method are an embodiment herein.

Seeds from which any the above triploid plants can be grown are also encompassed herein, as are parts of such a plant, such as triploid fruits, flowers, leaves, stems, cuttings, vegetative propagations, cells, seed propagations (e.g. selfings) and also in vitro cell- or tissue cultures, as well as pollen, ovaries, rootstocks, scions, etc. are encompassed herein. Thus, in one embodiment the triploid plant, or seeds from which the plant can be grown, or tissue or parts of the plant (pollen, anthers, ovules) comprises a mutant wap7.1 allele as described above.

A method for growing the triploid plants comprising at least one copy of a mutant wap7.1 allele is also provided. The triploid plants are changed from stenospermocarpic to parthenocarpic, i.e. no pollenizer plant is needed anymore to induce fruit development from the flowers, and these plants can therefore be grown in the absence of pollenizer plants, producing seedless fruits. Thus, an entire field or greenhouse can be grown with only triploid plants, increasing the yield of seedless, triploid fruits. The seedless fruits, comprising at least one copy (or two or three copies) of the mutant wap7.1 allele in their genome are also encompassed herein, as are food or feed products comprising fruits or fruit parts.

The method thus comprises: seeding or growing triploid watermelons plants comprising at least one copy of a mutant wap7.1 allele in a cultivation area, such as afield or greenhouse or tunnel, without the presence of pollenizer plants (e.g. without interplanting pollenizer plants), and allowing fruits to develop without pollination of the flowers (parthenocarpic), and optionally harvesting the seedless triploid fruits.

Vegetative Propagations and Cell or Tissue Cultures

The above diploid plants, tetraploid plants or triploid plants (or other polyploids) can also be reproduced vegetatively (clonally) and such vegetatively propagated plants, or 'vegetative propagations' are an embodiment of the invention. They can easily be distinguished from other watermelon plants by the presence of a mutant wap7.1 allele and/or phenotypically. The presence of one or more mutant wap7.1 alleles can be determined as described elsewhere herein.

Vegetative propagations can be made by different methods. For example one or more scions of a plant of the invention may be grafted onto a different rootstock, e.g. a biotic or abiotic stress tolerant rootstock.

Other methods include in vitro cell or tissue culture methods and regeneration of vegetative propagations from such cultures. Such cell or tissue cultures comprise or consist of various cells or tissues of a plant of the invention. In one aspect such a cell or tissue culture comprises or consists of vegetative cells or vegetative tissues of a plant of the invention.

In another aspect a cell or tissue culture comprises or consists of reproductive cells or tissues, such as anthers or ovules of a plant of the invention. Such cultures can be treated with chromosome doubling agents to make e.g. double haploid plants, or they can alternatively be used to make haploid plants (e.g. to make diploids from a tetraploid or to make haploids from a diploid).

An in vitro cell or tissue culture may, thus, comprise or consist of cells or protoplasts or plant tissue from a plant part selected from the group consisting of: fruit, embryo, meristem, cotyledon, pollen, ovule, leaf, anther, root, root tip, pistil, flower, seed, stem. Also parts of any of these are included, such as e.g. only the seed coat (maternal tissue).

Thus, in one aspect of the invention a cell culture or a tissue culture of cells of a plant comprising one, two, three or four copies of a mutant wap7.1 allele, all as described above, is provided. As mentioned, a cell culture or a tissue culture comprises cells or protoplasts or plant tissue from a plant part of a plant comprising a mutant wap7.1 allele may comprise or consist of cells or tissues selected from the group consisting of: embryo, meristem, cotyledon, pollen, leaf, anther, root, root tip, pistil, flower, seed, stem; or parts of any of these.

Also provided is a watermelon plant regenerated from such a cell culture or tissue culture, wherein the regenerated plant (or progeny thereof, e.g. obtained after selfing the regenerated plant) comprises the mutant wap7.1 allele. Therefore, in one aspect the watermelon plant comprising a mutant wap7.1 allele in one or more copies is a vegetatively propagated watermelon plant.

In a different aspect the cells and tissues of the invention (and optionally also the cell or tissue culture), comprising wap7.1 in one or more copies, are non-propagating cells or tissues.

Methods

A method for seedless triploid watermelon fruit production is provided, said method comprising:
1. providing a triploid hybrid (F1) watermelon plant or seed comprising at least one, preferably two or preferably three copies of a mutant wap7.1 allele,
2. planting or seeding said triploid hybrid plants in a field, preferably without planting or seeding diploid pollenizer plants in the same field, and optionally
3. harvesting the seedless watermelon fruits produced on the triploid plants, whereby the fruits are preferably produced without pollination of the female flowers.

In one aspect the triploid hybrid plant of step 1 is preferably not grafted onto a different rootstock. In another aspect it may be grafted onto a different rootstock.

As mentioned, there is no need anymore to provide diploid pollenizer plants to induce fruit set on of the female flowers of the triploid plants. This means that an entire field can be sown or transplanted with essentially only seeds or transplants of the F1 triploid seeds or plants. Yield of seedless watermelon fruits per hectare is therefore greatly enhanced. Also seeding and planting is made much easier as only one genotype is seeded or planted.

Thus, the method can also be described as a method of producing seedless watermelon fruits, said method comprising growing a triploid plant comprising at least one, preferably two, more preferably three copies of mutant wap7.1 allele and harvesting the fruits produced by said plants. The fruits develop preferably without pollination of the female flowers, i.e. in the absence of viable or fertile pollen. No insects, such as bees, are required anymore for fruit set, i.e. placing bee hives into or near the fields is not necessary.

The harvested triploid, seedless fruits may be packaged for fresh markets or for processing. Fruits comprising one, two or three wap7.1 alleles obtainable by the above method are encompassed herein. Optionally detection of the mutant wap7.1 allele e.g. by detection of the mutant wap7.1 allele using DNA, RNA or protein detection as described elsewhere, e.g. by PCR, genotyping or marker analysis of markers linked to (or closely linked to) the wap7.1 allele or being allele-specific (e.g. detecting the mutation which distinguishes the mutant allele from the wild type allele), can distinguish such fruits. Thus, in one embodiment, harvested triploid fruits (i.e. wap7.1/WAP7.1/WAP7.1 or wap7.1/wap7.1/WAP7.1 or wap7.1 wap7.1/wap7.1) are provided, such as packaged whole fruits or fruit parts and/or processed fruits or fruit parts.

Also provided is a method for production of a facultative parthenocarpic cultivated watermelon plant comprising the steps of
a) introducing mutations in a population of watermelon plants or providing a mutant population of watermelon plants;
b) selecting a plant producing seedless fruits without pollination of the female flowers and producing a seeded fruit after pollination of the female flowers and/or selecting a plant comprising a mutant allele of the WAP7.1 gene;
c) optionally verifying if the plant selected under b) comprises a mutant allele of a WAP7.1 gene; and
d) optionally growing the plants obtained under c).

A watermelon plant produced by the above method is encompassed.

The population of watermelon plants under a) is preferably a single genotype of a cultivated watermelon breeding line or variety, which is treated/has been treated with (or subjected to) a mutagenic agent, or progeny of such a population e.g. obtained after selfing individuals of the population to produce M2, M3 or further generation plants. This may for example be a TILLING population.

In step b) plants are screened for the phenotype, i.e. for being facultative parthenocarpic and/or the plants (or plant parts or DNA therefrom) are screened for the presence of a mutant allele of the WAP7.1 gene, i.e. an allele which either has reduced expression or no expression of the wild type WAP7.1 protein or an allele encoding a mutant WAP7.1 protein. Regarding the screening for the phenotype, it is understood that without pollination of the female flowers, seedless fruits should develop; with pollination of the female flowers seeded fruits should develop. This phenotypic screening can be done in several steps. For example first plants can be grown in an insect free environment and male flowers can be removed. Female flowers can be observed visually for flowering and fruit development (in absence of pollen). The developed fruit can be cut in half at maturity to check if these are seedless. Selected plants can e.g. be vegetatively reproduced to confirm the parthenocarpy phenotype and/or to e.g. hand-pollinate flowers to see if fruits are seeded upon pollination (facultative parthenocarpy). Regarding the screening of the plants for the presence of a mutant allele of the WAP7.1 gene, this can be done by various methods which detect wap7.1 DNA, RNA or protein, for example by e.g. designing PCR primers which amplify part of the coding region or all of the coding region to amplify the genomic DNA in order to determine if a plant comprises a mutation in the genomic DNA, or other methods.

Step c) can involve various methods to determine whether a mutant wap7.1 allele is present. For example marker analysis or sequence analysis of the chromosome region comprising the WAP7.1 locus can be carried out, or PCR or RT-PCR can be used to amplify the wap7.1 allele (or a part thereof) or the mRNA (cDNA). Also genetic analysis to determine the recessive inheritance may be carried out.

Also the use of a facultative parthenocarpic watermelon plant for producing seedless watermelon fruits is provided, preferably without pollination of the female flowers of the plant. Further the use of a mutant wap7.1 allele for generating facultative parthenocarpic watermelon plants and/or seedless watermelon fruits in the absence of pollination of the female flowers is provided. Likewise the use of a mutant wap7.1 allele of a WAP7.1 gene according to the invention for producing facultative parthenocarpic watermelon plants is encompassed herein.

In one aspect the plants, plant parts and plant cells according to the invention are not exclusively obtained by means of an essentially biological process as defined by Rule 28 (2) EPC (European Patent Convention).

In one aspect the plants are non-GMO (not genetically modified).

In one aspect the mutant alleles are generated by mutagenesis (e.g. chemical or radiation mutagenesis) or by targeted mutagenesis, especially using the CRISPR system (e.g. Crispr/Cas9 or Crispr/Cpf1 or other nucleases). In one aspect the cultivated plant comprising the mutant wap7.1 allele is not a transgenic plant, e.g. non transgenic progeny are selected which do not comprise e.g. the CRISPR construct.

In one aspect the mutant allele of the WAP7.1 gene comprises a human induced mutation, i.e. a mutation introduced by mutagenesis techniques, such as chemical mutagenesis or radiation mutagenesis, or targeted mutagenesis techniques, such as Crispr based techniques.

A method for targeted mutagenesis of the endogenous WAP7.1 gene in watermelon is provided herein, using any targeted gene modification method, such as CRISPR based methods (e.g. Crispr/Cas9 or Crispr/Cpf1), TALENS, Zinc Fingers or other methods.

In one aspect an isolated mutant WAP7.1 protein and an isolated wild type WAP7.1 protein is provided or an isolated nucleic acid molecule encoding a mutant WAP7.1 protein or a wild type WAP7.1 protein.

Also an antibody able to bind a mutant or wild type WAP7.1 protein is encompassed herein.

Detection Methods

In one aspect a screening method for identifying and/or selecting seeds, plants or plant parts or DNA from such seeds, plants or plant parts comprising in their genome a mutant allele of a WAP7.1 protein-encoding gene is provided.

The method comprises screening at the DNA, RNA (or cDNA) or protein level using known methods, in order to detect the presence of the mutant allele. There are many methods to detect the presence of a mutant allele of a gene.

Thus, a method for screening and/or selecting plants, seeds or plant material or plant parts, or DNA or RNA or protein derived therefrom, for the presence of a mutant wap7.1 allele is provided comprising one or more of the following steps:

a) determining if the gene expression of the endogenous WAP7.1 gene is reduced or abolished;

b) determining if the amount of wild type WAP7.1 protein is reduced or abolished;

c) determining if a mutant mRNA, cDNA or genomic DNA encoding a mutant WAP7.1 protein is present;

d) determining if a mutant WAP7.1 protein is present;

e) determining if plants or progeny thereof are facultative parthenocarpic.

Routine methods can be used, such as RT-PCR, PCR, antibody based assays, sequencing, genotyping assays (e.g. allele-specific genotyping), phenotyping, etc.

The plants or plant material or plant parts may be watermelon plants or plant materials or plant parts, such as leaves, leaf parts, cells, fruits, fruit parts, ovaries, stem, hypocotyl, seed, parts of seeds, seed coat, embryo, etc.

For example if there is a single nucleotide difference (single nucleotide polymorphism, SNP) between the wild type and the mutant allele (as e.g. shown in Table 1), a SNP genotyping assay can be used to detect whether a plant or plant part or cell comprises the wild type nucleotide or the mutant nucleotide in its genome. For example the SNP can easily be detected using a KASP-assay (see world wide web at kpbioscience.co.uk) or other SNP genotyping assays. For developing a KASP-assay, for example 50, 60 or 70 base pairs upstream and 50, 60 or 70 base pairs downstream of the SNP can be selected and two allele-specific forward primers and one allele specific reverse primer can be designed. See e.g. Allen et al. 2011, Plant Biotechnology J. 9, 1086-1099, especially p 097-1098 for KASP-assay method.

Equally other genotyping assays can be used. For example, a TAQMAN® SNP genotyping assay, a High Resolution Melting (HRM) assay, SNP-genotyping arrays (e.g. Fluidigm, Illumina, etc.) or DNA sequencing may equally be used.

In one aspect for example the SNP marker mWM23348403 at nucleotide 51 of SEQ ID NO: 5, or at nucleotide 51 of a sequence comprising at least 92%, 93%, 94%, 95%, 96%, 97%, 98%, 99% or more sequence identity to SEQ ID NO: 5, can be used to detect the presence or absence of a mutant wap7.1 allele encoding a mutant protein comprising a W1054STOP mutation in watermelon. Based on the difference between the genomic sequence of the wild type allele and the mutant allele, the skilled person can easily develop markers which can be used to detect specific alleles (e.g. those of Table 1 or others).

Also provided herein is a method for identifying a watermelon plant (or plant part) comprising a mutant wap7.1 allele, the method comprising detecting in the plant (or plant part) the presence of a mutant wap7.1 allele, wherein the presence is detected by at least one marker within the wap7.1 allele or by detecting the protein encoded by the wap7.1 allele. The method for detecting the mutant wap7.1 allele is selected from the group consisting of PCR amplification, nucleic acid sequencing, nucleic acid hybridization and an antibody-based assay (e.g. immunoassay) for detecting the wap7.1 protein encoded by the allele.

Also provided herein is a method for identifying a watermelon plant (or plant part) comprising a mutant wap7.1 allele comprising a mutation in a regulatory element, the method comprising detecting in the plant (or plant part) the reduced gene expression or absence of gene expression of the mutant wap7.1 allele, wherein the presence is detected by mRNA levels (cDNA) of the wild type WAP7.1 allele or by detecting the protein levels of the wild type WAP7.1 protein. The method for detecting the mutant wap7.1 allele is selected from the group consisting of PCR amplification (e.g. RT-PCR), nucleic acid sequencing, western blotting and an antibody based assay (e.g. immunoassay) for detecting the WAP7.1 protein encoded by the allele.

Also provided is a method for determining, or detecting or assaying, whether a cell or of a watermelon plant or plant part comprises a mutant allele of a gene named WAP7.1 encoding a protein of SEQ ID NO: 1, or a protein comprising at least 94%, 95%, 96%, 97% or 98% sequence identity to SEQ ID NO: 1, is provided herein. In one aspect the method comprises determining the expression of the allele, and/or determining the coding sequence of the allele and/or determining part of the coding sequence of the allele (e.g. a SNP genotype of the allele), and/or determining the amino acid sequence of the protein produced and/or the amount of protein produced.

Various method can be used to determine whether a plant or part thereof comprises a mutant wap7.1 allele of the invention. As mentioned, the mRNA (or cDNA) level of the wild type allele may be determined, or the wild type protein level may be determined, to see if there is a reduced expression or no expression of the wild type allele. Also, the coding sequence or part thereof may be analysed, for example if one already knows which mutant allele may be present, an assay can be developed to detect the mutation, e.g. a SNP genotyping assay can e.g. distinguish between the presence of the mutant allele and the wild type allele, e.g. genotyping for marker mWM23348403.

A method for selection of a plant or seed comprising the steps of:

a) identifying a plant or seed which has a mutation in an allele of a gene encoding a WAP7.1 protein, wherein the wild type allele of the gene encodes a WAP7.1 protein comprising at least 94%, 95%, 96%, 97% or 98% or 99% sequence identity to SEQ ID NO:1, and optionally b) determining whether the plant, or a progeny plant produced by self-fertilization, is facultative parthenocarpic and optionally c) selecting a plant or seed comprising at least on copy of the mutant allele of step a).

A method for production of a plant, preferably a watermelon plant, comprising the steps of:

a) introducing mutations in a population of plants or seeds, b) selecting a plant producing seedless fruit in the absence of pollination and seeded fruits after pollination and/or selecting a plant or seed comprising a mutant wap7.1 allele in its genome, c) optionally verifying if the plant selected under b) has a mutation in an allele encoding a WAP7.1 protein, and optionally d) growing or cultivating the plant or seed obtained under c), wherein the wild type allele of the gene encodes a WAP7.1 protein comprising at least 94% sequence identity to any one of the proteins selected from the group of: SEQ ID NO: 1.

A method for production of a plant comprising the steps of:

a) introduction of a foreign nucleic acid molecule into a plant, wherein the foreign nucleic acid molecule is chosen from the group consisting of i) DNA molecules, which code at least one antisense RNA, which effects a reduction in the expression of an endogenous gene encoding a WAP7.1 protein;

ii) DNA molecules, which by means of a co-suppression effect lead to the reduction in the expression of an endogenous gene encoding a WAP7.1 protein;

iii) DNA molecules, which code at least one ribozyme, which splits specific transcripts of an endogenous gene encoding a WAP7.1 protein;

iv) DNA molecules, which simultaneously code at least one antisense RNA and at least one sense RNA, wherein the said antisense RNA and the said sense RNA form a double-stranded RNA molecule, which effects a reduction in the expression of an endogenous gene encoding a WAP7.1 protein (RNAi technology);

v) nucleic acid molecules introduced by means of in vivo mutagenesis, which lead to a mutation or an insertion of a heterologous sequence in an endogenous gene encoding a WAP7.1 protein, wherein the mutation or insertion effects a reduction in the expression of a gene encoding a WAP7.1 protein or results in the synthesis of a loss-of-function or reduced function WAP7.1 protein;

vi) nucleic acid molecules, which code an antibody, wherein the antibody results in a reduction in the activity of an endogenous gene encoding a WAP7.1 protein due to the bonding of the antibody to an endogenous WAP7.1 protein;

vii) DNA molecules, which contain transposons, wherein the integration of these transposons leads to a mutation or an insertion in an endogenous gene encoding a WAP7.1 protein, which effects a reduction in the expression of an endogenous gene encoding a WAP7.1 protein, or results in the synthesis of an inactive protein;

viii) T-DNA molecules, which, due to insertion in an endogenous gene encoding a WAP7.1 protein, effect a reduction in the expression of an endogenous gene encoding a WAP7.1 protein, or result in the synthesis of a loss-of-function or reduced function WAP7.1 protein;

ix) nucleic acid molecules encoding rare-cleaving endonucleases or custom-tailored rare-cleaving endonucleases preferably a meganuclease, a TALENs or a CRISPR/Cas system b) selecting a plant wherein the plant, or a progeny of the plant produced by self-fertilization, produces seedless fruit in the absence of pollination and seeded fruits after pollination, optionally c) verifying if the plant selected under b) has a decreased activity of a WAP7.1 protein compared to wild type plants into whose genome e.g. no foreign nucleic acid molecules had been integrated, optionally d) growing/cultivating the plants obtained under c).

A plant obtained by any of the methods above is encompassed herein.

In one aspect a genetically modified plant and plant part is provided, whereby the plant has reduced expression or no expression of the endogenous WAP7.1 gene, e.g. through silencing of the endogenous WAP7.1 gene. Such a plant may be any plant, in one aspect it is a watermelon. However, it can also be a cucumber, melon, pepper, maize, soybean, wheat, canola, tomato, cotton, etc.

In another aspect a plant and plant part is provided, comprising a mutation in the endogenous WAP7.1 gene, e.g. an induced mutation generated e.g. by targeted mutagenesis, whereby either the gene expression is reduced or abolished or the expressed gene encodes a reduced function or loss of function WAP7.1 protein compared to the wild type protein. Such a plant may be any plant, in one aspect it is a watermelon. However, it can also be a cucumber, melon, maize, soybean, wheat, canola, tomato, cotton, pepper, etc. As the WAP7.1 gene in other species may have less sequence identity to the watermelon WAP7.1 gene, it is encompassed herein that in this aspect of the invention the WAP7.1 gene is a gene encoding a protein comprising at least 60%, 65%, 70%, 75%, 80%, 85%, 90%, 94%, 95% sequence identity to SEQ ID NO: 1. Optionally the WAP7.1 gene is a gene encoding a protein comprising at least 60%, 65%, 70%, 75%, 80%, 85%, 90%, 94%, 95% sequence identity to SEQ ID NO: 1, whereby the protein comprises the conserved Zn-binding domain, Peptide Binding domain, Plus3 domain and/or Proline Binding motif of SEQ ID NO: 1, or a Zn-binding domain, Peptide Binding domain, Plus3 domain and/or Proline Binding motif comprising at least 70%, 75%, 80%, 85%, 90%, 91%, 92%, 93%, 94%, 95% sequence identity to the Zn-binding domain, Peptide Binding domain, Plus3 domain and/or Proline Binding motif of SEQ ID NO: 1. The skilled person can identify orthologs of the WAP7.1 gene in such other species, e.g. in melon and cucumber, pepper or tomato, and thereby make facultative parthenocarpic melon, cucumber, pepper or tomato plants. All embodiments described herein for watermelon apply equally for other crop species, with the difference that the WAP7.1 gene may thus encode a protein with less than 94% sequence identity to the wild type WAP7.1 watermelon protein of SEQ ID NO: 1.

Also provided herein is a method for screening watermelon plants, seeds, plant parts, or DNA therefrom, for the presence of a mutant allele of a gene named WAP7.1, or for selecting a watermelon plant, seed or plant part comprising a mutant allele of a gene named WAP7.1, comprising the steps:

a) analysing whether the genomic DNA comprises a wild type WAP7.1 allele which encodes a protein of SEQ ID NO: 1 (or a wild type protein comprising at least 94% identity to SEQ ID NO: 1) and/or a mutant WAP7.1 allele which encodes a mutant protein comprising one or more amino acids replaced, inserted or deleted compared to the wild type WAP7.1 protein, and optionally b) selecting a plant, seed or plant part comprising two copies of the wild type allele, two copies of the mutant allele or one copy of the wild type allele and one copy of the mutant allele.

In one aspect the method step a) comprises a method selected from:

i) amplification of at least part of the WAP7.1 allele using one or more oligonucleotide primers which hybridize to the DNA of the WAP7.1 allele, ii) hybridization of one or more oligonucleotide probes to at least part of the DNA of the WAP7.1 allele, iii) sequencing the DNA, mRNA or cDNA of the WAP7.1 allele.

So, for example a DNA sample can be obtained from a plant, seed or plant part, and a PCR reaction can be carried out to amplify part of the wild type WAP7.1 allele and/or part of the mutant WAP7.1 allele.

Competitive PCR methods, for example, can be used (such as a KASP assay) to generate amplification products of the alleles present at the WAP7.1 locus in the genomic DNA. Similarly, oligonucleotide probes can generate hybridization products of the alleles present at the WAP7.1 locus in the genomic DNA. Primers or probes may be designed to be specific to a particular WAP7.1 allele, e.g. to differentiate between the wild type allele and a mutant allele. For example, SNP marker mWM23348403 comprises a SNP at nucleotide 51, which differentiates between the wild type allele encoding a protein comprising amino acid W1054 and the mutant allele encoding a protein comprising a premature STOP codon at the codon for amino acid W1054. Primers or probes can be designed to detect this SNP and the same can be done for any other polymorphism (e.g. SNP or INDEL) found between wild type and mutant WAP7.1 alleles, such as those of Table 1.

In one aspect, a genotyping assay is provided for genotyping watermelon plants, seeds, plant parts, cells or tissues, comprising the steps:

a) providing genomic DNA of one or more watermelon plants or a population of plants, and b) carrying out a genotyping assay which detects the presence of the wild type allele encoding the protein of SEQ ID NO: 1 or a wild type allele encoding a protein comprising at least 94% sequence identity to SEQ ID NO: 1 and/or the presence of a mutant allele (or two different mutant alleles), wherein the mutant allele encodes a mutant protein which comprises one or more amino acids inserted, deleted or replaced compared to the wild type protein of SEQ ID NO: 1 or compared to a wild type protein comprising at least 94% sequence identity to SEQ ID NO: 1, and optionally c) selecting a plant, seed, plant part, cell or tissue comprising either two copies of the wild type allele, or one copy of the wild type allele and one copy of a mutant allele, or two copies of a mutant allele.

In step b) the mutation in the mutant allele preferably causes one or more amino acids to be inserted, deleted or replaced with respect to the wild type protein, e.g. the mutant allele encodes one of the mutant WAP7.1 proteins described herein e.g. in Table 1.

So, for example the genotype for the allele comprising the G/A SNP (codon AGG→AAG; see Table 1, row 1), which differentiates between amino acid R at position 346 in SEQ ID NO: 1 or amino acid R at the equivalent position in a wild type protein comprising at least 94%, 95%, 96%, 97%, 98% or 99% sequence identity to SEQ ID NO: 1 and amino acid K at position 346 in SEQ ID NO: 1 or amino acid K at the equivalent position in a wild type protein comprising at least 94%, 95%, 96%, 97%, 98% or 99% sequence identity to SEQ ID NO: 1, can be analyzed in the above assay. Thus, in one aspect the assay can e.g. detect the allele encoding the protein of SEQ ID NO: 1 (wild type WAP7.1) and/or the allele encoding the protein of SEQ ID NO: 11 (mutant WAP7.1 protein having a R346K replacement).

Also, for example the genotype for the allele comprising the G/A SNP (codon AGC→AAC; see Table 1, row 2), which differentiates between amino acid S at position 324 in SEQ ID NO: 1 or amino acid S at the equivalent position in a wild type protein comprising at least 94%, 95%, 96%, 97%, 98% or 99% sequence identity to SEQ ID NO: 1 and amino acid N at position 324 in SEQ ID NO: 1 or amino acid N at the equivalent position in a wild type protein comprising at least 94%, 95%, 96%, 97%, 98% or 99% sequence identity to SEQ ID NO: 1, can be analyzed in the above assay. Thus, in one aspect the assay can e.g. detect the allele encoding the protein of SEQ ID NO: 1 (wild type WAP7.1) and/or the allele encoding the protein of SEQ ID NO: 12 (mutant WAP7.1 protein having a S324N replacement).

Likewise the genotype for the allele comprising the C/T SNP (codon CCT→TCT; see Table 1, row 3), which differentiates between amino acid P at position 830 in SEQ ID NO: 1 or amino acid P at the equivalent position in a wild type protein comprising at least 94%, 95%, 96%, 97%, 98% or 99% sequence identity to SEQ ID NO: 1 and amino acid S at position 830 in SEQ ID NO: 1 or amino acid S at the equivalent position in a wild type protein comprising at least 94%, 95%, 96%, 97%, 98% or 99% sequence identity to SEQ ID NO: 1, can be analyzed in the above assay. Thus, in one aspect the assay can e.g. detect the allele encoding the protein of SEQ ID NO: 1 (wild type WAP7.1) and/or the allele encoding the protein of SEQ ID NO: 13 (mutant WAP7.1 protein having a P830S replacement).

Also the genotype for the allele comprising the G/A SNP (codon GCA→ACA; see Table 1, row 4), which differentiates between amino acid A at position 328 in SEQ ID NO: 1 or amino acid A at the equivalent position in a wild type protein comprising at least 94%, 95%, 96%, 97%, 98% or 99% sequence identity to SEQ ID NO: 1 and amino acid T at position 328 in SEQ ID NO: 1 or amino acid T at the equivalent position in a wild type protein comprising at least 94%, 95%, 96%, 97%, 98% or 99% sequence identity to SEQ ID NO: 1, can be analyzed in the above assay. Thus, in one aspect the assay can e.g. detect the allele encoding the protein of SEQ ID NO: 1 (wild type WAP7.1) and/or the allele encoding the protein of SEQ ID NO: 14 (mutant WAP7.1 protein having a A328T replacement).

Also the genotype for the allele comprising the G/A SNP (codon TGG→TGA; see Table 1, row 5), which differentiates between amino acid W at position 1054 in SEQ ID NO: 1 or amino acid W at the equivalent position in a wild type protein comprising at least 94%, 95%, 96%, 97%, 98% or 99% sequence identity to SEQ ID NO: 1 and an allele comprising a STOP codon for amino acid W at position 1054 in SEQ ID NO: 1 or for amino acid W at the equivalent position in a wild type protein comprising at least 94%, 95%, 96%, 97%, 98% or 99% sequence identity to SEQ ID NO: 1, can be analyzed in the above assay. Thus, in one aspect the assay can e.g. detect the allele encoding the protein of SEQ ID NO: 1 (wild type WAP7.1) and/or the allele encoding the protein of SEQ ID NO: 2 (mutant WAP7.1 protein having a W1054* replacement).

Further also the genotype for the allele comprising the C/T SNP (codon CAA→TAA; see Table 1, row 6), which differentiates between amino acid Q at position 373 in SEQ ID NO: 1 or amino acid Q at the equivalent position in a wild type protein comprising at least 94%, 95%, 96%, 97%, 98% or 99% sequence identity to SEQ ID NO: 1 and an allele comprising a STOP codon for amino acid Q at position 373 in SEQ ID NO: 1 or for amino acid Q at the equivalent position in a wild type protein comprising at least 94%, 95%, 96%, 97%, 98% or 99% sequence identity to SEQ ID NO: 1, can be analyzed in the above assay. Thus, in one aspect the assay can e.g. detect the allele encoding the protein of SEQ ID NO: 1 (wild type WAP7.1) and/or the allele encoding the protein of SEQ ID NO: 10 (mutant WAP7.1 protein having a Q373* replacement).

Obviously, also the presence of one or two mutant alleles can be detected in in the above assay, e.g. one or two copies of a specific mutant allele or of two different mutant alleles. So, for example, the presence of the allele encoding the protein of SEQ ID NO: 11 and/or the mutant allele encoding the protein of SEQ ID NO: 12 may be detected in such an assay. In the method above the assay can detect the genotype of any WAP7.1 allele, be it a wild type allele and/or one or more mutant alleles.

The wild type alleles are for example the genomic DNA at the WAP7.1 locus on chromosome 7. For example SEQ ID NO: 6 provides herein the genomic DNA encoding a wild type WAP7.1 protein, but likewise genomic sequences comprising at least 90%, 91%, 92%, 93% 94%, 95%, 96%, 97%, 98% or 99% sequence identity to SEQ ID NO: 6 may be genomic DNA sequences encoding wild type WAP7.1 proteins.

In one aspect, therefore, one or more of the following alleles are detected in step b of the method above:

a wild type WAP7.1 allele encoding a protein SEQ ID NO: 1 or a wild type protein comprising at least 94%, 95%, 96%, 97%, 98% or 99% sequence identity to SEQ ID NO: 1;

a mutant WAP7.1 allele encoding a WAP7.1 mutant protein comprising one or more amino acids inserted, replaced or deleted with respect to the wild type WAP7.1 allele encoding a protein SEQ ID NO: 1 or a wild type protein comprising at least 94%, 95%, 96%, 97%, 98% or 99% sequence identity to SEQ ID NO: 1 (see also elsewhere herein);

a mutant WAP7.1 allele encoding a mutant WAP7.1 protein comprising a R346K replacement in SEQ ID NO: 1 or at the equivalent amino acid position in a wild type protein comprising at least 94%, 95%, 96%, 97%, 98% or 99% sequence identity to SEQ ID NO: 1;

a mutant WAP7.1 allele encoding a mutant WAP7.1 protein comprising a S324N replacement in SEQ ID NO: 1 or at the equivalent amino acid position in a wild type protein comprising at least 94%, 95%, 96%, 97%, 98% or 99% sequence identity to SEQ ID NO: 1;

a mutant WAP7.1 allele encoding a mutant WAP7.1 protein comprising a P830S replacement in SEQ ID NO: 1 or at the equivalent amino acid position in a wild type protein comprising at least 94%, 95%, 96%, 97%, 98% or 99% sequence identity to SEQ ID NO: 1;

a mutant WAP7.1 allele encoding a mutant WAP7.1 protein comprising a A328T replacement in SEQ ID NO: 1 or at the equivalent amino acid position in a wild type protein comprising at least 94%, 95%, 96%, 97%, 98% or 99% sequence identity to SEQ ID NO: 1;

a mutant WAP7.1 allele encoding a mutant WAP7.1 protein comprising a W1054* replacement in SEQ ID NO: 1 or at the equivalent amino acid position in a wild type protein comprising at least 94%, 95%, 96%, 97%, 98% or 99% sequence identity to SEQ ID NO: 1;

a mutant WAP7.1 allele encoding a mutant WAP7.1 protein comprising a Q373* replacement in SEQ ID NO: 1 or at the equivalent amino acid position in a wild type protein comprising at least 94%, 95%, 96%, 97%, 98% or 99% sequence identity to SEQ ID NO: 1.

Step a) may comprise isolation of genomic DNA from the plant, seeds, plant part, cell or tissue to be analyzed in the genotyping assay. Often crude DNA extractions methods can be used, as known in the art.

Step b) preferably comprises a bi-allelic genotyping assay, which makes use of allele-specific oligonucleotide primers and/or allele-specific probes, i.e. primers or probes which discriminate between e.g. the wild type allele and the mutant allele or between two mutant alleles.

The plants of step a) may be mutagenized using e.g. chemical or radiation mutagens or gene editing techniques. Thus prior to step a) there may be a step of treating the plants, seeds or plant parts with a mutagenic agent or induce targeted mutations in the WAP7.1 allele.

Various genotyping assays can be used, as long as they can detect INDELs and SNPs and can differentiate between e.g. the wild type allele being present in the genomic DNA (at the WAP7.1 locus on chromosome 7) and/or one or more mutant alleles of the WAP7.1 gene being present in the genomic DNA.

Genotyping assays are generally based on allele-specific primers used in PCR or thermal cycling reactions (polymerase chain reaction) to amplify either the wild type or mutant allele and detect the amplification product or on allele-specific oligonucleotide probes, which hybridize to either the wild type allele or the mutant allele, or both. For example genotyping with BHQPLUS® probes uses two allele specific probes and two primers that flank the region of the polymorphism, and during thermal cycling the polymerase encounters the allele-specific probes bound to the DNA and releases a fluorescent signal. Allele discrimination involves competitive binding of the two allele-specific BHQPLUS® probes (see also biosearchtech.com).

Examples of genotyping assays are the KASP-assay (by LGC, see www at LGCgenomics.com and also WWW at biosearchtech.com/products/pcr-kits-and-reagents/genotyping-assays/kasp-genotyping-chemistry), based on competitive allele-specific PCR and end-point fluorescent detection, the TAQMAN®-assay (Applied Biosystems), which is also PCR based, HRM assays (High Resolution Melting Assay), wherein allele-specific probes are detected using real time PCR, or the rhAmp assay, based on Rnase H2-dependent PCR, BHQPLUS® genotyping, BHQplex CoPrimer genotyping and many others.

The KASP-assay is also described in He C, Holme J, Anthony J. 'SNP genotyping: the KASP assay. Methods Mol Biol. 2014; 1145:75-86' and EP1726664B1 or U.S. Pat. No. 7,615,620 B2, incorporated by reference. The KASP genotyping assay utilizes a unique form of competitive allele-specific PCR combined with a novel, homogeneous, fluorescence-based reporting system for the identification and measurement of genetic variation occurring at the nucleotide level to detect single nucleotide polymorphisms (SNPs) or inserts and deletions (InDels). The KASP technology is suitable for use on a variety of equipment platforms and provides flexibility in terms of the number of SNPs and the number of samples able to be analyzed. The KASP chemistry functions equally well in 96-, 384-, and 1,536-well microtiter plate formats and has been utilized over many years in large and small laboratories by users across the fields of human, animal, and plant genetics.

The TAQMAN® genotyping assays is also described in Woodward J. 'Bi-allelic SNP genotyping using the TAQMAN® assay.' Methods Mol Biol. 2014; 1145:67-74, U.S. Pat. Nos. 5,210,015 and 5,487,972, incorporated herein by reference. With TAQMAN® technology allele-specific probes are utilized for quick and reliable genotyping of known polymorphic sites. TAQMAN® assays are robust in genotyping multiple variant types, including single nucleotide polymorphisms, insertions/deletions, and presence/absence variants. To query a single bi-allelic polymorphism, two TaqMan probes labeled with distinct fluorophores are designed such that they hybridize to different alleles during PCR-based amplification of a surrounding target region. During the primer extension phase of PCR, the 5'-3' exonuclease activity of Taq polymerase cleaves and releases the fluorophores from bound probes. At the end of PCR, the emission intensity of each fluorophore is measured and allele determination at the queried site can be made.

Various genotyping assays can, therefore, be used, which can differentiate between the presence of the e.g. one or more wild type alleles of the WAP7.1 gene, encoding the protein of SEQ ID NO: 1 or a protein comprising at least 94% identity to SEQ ID NO: 1, and/or one or more mutant alleles of the WAP7.1 gene. Various mutant alleles of the WAP7.1 gene can be detected. So, not only the mutant allele encoding the protein of SEQ ID NO: 2, 10, 11, 12, 13, or 14, but the assay can be designed to detect any other mutant allele of the WAP7.1 gene, including those described in Table 1 and others.

As mentioned preferably a bi-allelic genotyping assay is used, e.g. a KASP-assay, a TAQMAN® assay, a BHQPLUS® assay, PACE genotyping (see world wide web at idtdna.com/pages/products/qpcr-and-pcr/genotyping/pace-snp-genotyping-assays) or any other bi-allelic genotyping assay.

In one aspect the genotyping assay in step b) of the methods above is a KASP-assay. Thus in step b) a competitive PCR is carried out using two forward primers and one common reverse primer. The two forward primers comprise at least 10, 11, 12, 13, 14, 15, 16, 17, 18, 19 or 20 nucleotides complementary to the genomic sequence (or the complement strand thereof). In addition the two forward primers comprise 1, 2, 3 or more nucleotides (preferably at the 3'end of the primers) which provide specificity to the SNP or INDEL which differentiates e.g. the wild type sequence from e.g. the mutant sequence of the allele or which differentiates the sequences of two mutant alleles. The two forward primers thereby have different binding specificity (or preference) to e.g. either the wild type allele and/or e.g. to the mutant allele. For example the Fam-primer may comprise e.g. 17 nucleotides of the wild type sequence and 1 nucleotide specific for the nucleotide of the mutant allele, and the VIC-primer may comprise 18 nucleotides of the wild type allele and 1 nucleotide specific to the nucleotide of the wild type allele. A KASP-assay can easily be designed to differentiate between e.g. the wild type allele and/or any mutant allele of the WAP7.1 (which differs from the wild type allele in one or more nucleotides being inserted, deleted or replaced) gene or which differentiates between different mutant alleles of the gene, so e.g. the assay can be designed for any SNP or INDEL that differentiates any two WAP7.1 alleles.

It is noted that genotyping assays, such as the KASP assay, can also be carried out to detect the mutant and/or wild type WAP7.1 allele in triploid or tetraploid watermelon plants and plant parts in the same way as described for diploid watermelon plants and plant parts.

In one aspect the mutant allele of the WAP7.1 gene encodes a protein comprising one or more amino acids inserted, replaced or deleted with respect of the wild type protein of SEQ ID NO: 1, as already described elsewhere herein.

Therefore, in one embodiment a method is provided for detecting, and optionally selecting, a watermelon plant, seed or plant part comprising at least one copy of a wild type allele and/or of a mutant allele of a gene named WAP7.1, comprising:

a) providing genomic DNA of a watermelon plant or of a plurality of plants (e.g. a breeding population, F2, backcross, etc.), b) carrying out an assay (e.g. a bi-allelic genotyping assay) that discriminates or can discriminate between the presence of alleles in the genomic DNA of a), based on nucleic acid amplification (e.g. comprising the use of allele specific oligonucleotide primers) and/or nucleic acid hybridization (e.g. comprising the use of allele-specific oligonucleotide probes), to detect the presence of a wild type allele of the gene and/or one or more mutant alleles of the gene, wherein the wild type allele encodes a protein of SEQ ID NO: 1 (or a wild type WAP7.1 protein comprising at least 94%, 95%, 96%, 97%, 98%, 99%, 99.5% or 99.8% or 99.9% identity to SEQ ID NO: 1), and the mutant allele encodes a protein comprising one or more amino acids inserted, deleted or replaced with respect to the wild type protein of SEQ ID NO: 1 (or with respect to a wild type WAP7.1 protein comprising at least 94%, 95%, 96%, 97%, 98%, 99%, 99.5% or 99.8% or 99.9% identity to SEQ ID NO: 1), and optionally c) selecting a plant, seed or plant part comprising one or two copies of the mutant allele.

Under step b) the genotyping assay discriminates between e.g. the wild type and/or the one or more mutant alleles based on nucleic acid (especially DNA) amplification reactions making use of e.g. oligonucleotide primers, such as PCR (Polymerase Chain Reaction) and PCR primers, preferably allele-specific primers, and/or nucleic acid hybridization making use of as oligonucleotide probes, preferably allele-specific probes.

The primers or probes are preferably modified to comprise a label, e.g. a fluorescent label, or to comprise a tail sequence or other modification.

In one aspect, in any of the above methods the assay uses one or more WAP7.1 allele specific primers or one or more WAP7.1 allele specific probes.

As mentioned, based on the genomic sequence of SEQ ID NO: 6 or other (e.g. degenerate) genomic sequences which encode the protein of SEQ ID NO: 1 or the genomic sequence of a mutant allele which encodes e.g. a protein comprising one or more amino acids inserted, deleted or replaced in comparison to SEQ ID NO: 1, PCR primers and nucleic acid probes can be designed using known methods or software programs for oligonucleotide design. Primers and probes may for example be at least 10, 11, 12, 13, 14, 15, 16, 17, 18, 19, 20, 21, 22, 23, 24 or more nucleotides (bases) in length and anneal to (or hybridize to) the template DNA sequence, i.e. they preferably have at least 94%, 95%, 96%, 97%, 98%, 99% or 100% sequence identity to the target sequence. The primer or probe specificity to e.g. a wild type allele or a mutant allele (or to two or more mutant alleles) is due to at least 1, 2, 3 or more nucleotides of the primer or probe being specific for either allele. The primers or probes are thus designed around the polymorphism (e.g. the SNP or InDel) between the two (or more) alleles of the target gene, so that they discriminate between these. In one aspect the assay is a bi-allelic genotyping assay selected from e.g. a KASP-assay, a TAQMAN®-assay, a BHQPLUS® probe assay or any other bi-allelic genotyping assay.

In one aspect, the mutant allele comprises at least one codon inserted or duplicated in the coding region of the allele, or at least one codon changed into another codon (e.g. through a single nucleotide change), or at least one codon deleted or changed into a STOP codon.

In any of the methods above, in one aspect the mutant allele encodes a protein as described in Table 1. Thus, in one aspect the methods can be used to discriminate between plants, seeds or plant parts comprising two copies of the wild type WAP7.1 allele encoding the protein of SEQ ID NO: 1, two copies of the mutant WAP7.1 allele encoding the mutant protein of Table 1, or one copy of each allele (heterozygous). In another aspect the methods can be used to discriminate between plants, seeds or plant parts comprising one or two copies of any one or more mutant WAP7.1 allele encoding the mutant proteins of Table 1. Optionally plants, plant parts or seeds comprising any of these genotypes may be selected for e.g. further breeding or for use in watermelon production.

Although any DNA genotyping assay may be used in the above methods, be it PCR based (using PCR primers) and/or hybridization based (using probes), in one aspect a KASP-assay is used to discriminate between the wild type and the mutant allele. The assay can be used in a high throughput way, e.g. in 96 well plates or more well plates (e.g. 384 well plates).

In one aspect the assay discriminates between the G/A SNP at nucleotide 51 of SEQ ID NO: 5. So the primers or probes detect the allele comprising the G or the A at nucleotide 51 of SEQ ID NO: 5.

Depending on the SNP or INDEL between the wild type and/or mutant WAP7.1 alleles, various allele-specific primers and probes can be designed for use in the assays. See also Table 1 SNP information.

In one aspect two forward primers (e.g. one for the wild type allele and one for the mutant allele) and one common reverse primer (e.g. for both the wild type and the mutant allele) are used in the KASP-assay. In one aspect the two forward primers and the reverse primer comprise at least 10, 11, 12, 13, 14, 15, 16, 17, 18, 19 or more nucleotides of genomic WAP7.1 sequence or of the complement sequence thereof. The forward primers further comprise at least 1, 2, or 3 nucleotides (preferably at the 3'end of the primer) which confer specificity (or preference) to either amplification of e.g. the wild type allele or amplification of the mutant allele; or which confer specificity to different mutant alleles. Each forward primer forms a primer pair with the common reverse primer to amplify the DNA sequence of the target allele in between the primer pair, during thermal cycling. Standard components for thermal cycling are used and standard components for KASP-assays.

In another embodiment a method is provided for producing a hybridization product or an amplification product of e.g. a wild type allele and/or of a (or one or two or more) mutant alleles of a gene named WAP7.1, comprising:

a) providing genomic DNA of a watermelon plant or of a plurality of plants (e.g. a breeding population, F2, backcross, etc.), b) carrying out an assay (e.g. a bi-allelic genotyping assay) that discriminates or can discriminate between the presence of alleles in the genomic DNA of a), which assay generates a nucleic acid amplification product (e.g. through the use of allele specific oligonucleotide primers to generate the product) and/or which assay generates a nucleic acid hybridization product (e.g. through the use of allele-specific oligonucleotide probes to generate the hybridization product), whereby the amplification product or hybridization product indicates the presence of a wild type allele of the gene and/or a mutant allele of the gene in the DNA, wherein the wild type allele encodes the protein of SEQ ID NO: 1 or a wild type protein comprising at least 94% sequence identity to SEQ ID NO: 1) and the mutant allele encodes a protein comprising one or more amino acids inserted, duplicated, deleted or replaced with respect to the wild type protein of SEQ ID NO: 1 or the wild type protein comprising at least 94% sequence identity to SEQ ID NO: 1), and optionally c) selecting a plant, seed or plant part comprising one or two copies of the mutant allele. Also a method of amplifying all or part of a mutant and/or wild type WAP7.1 allele from a genomic DNA sample derived from a watermelon plant, plant part or seed is provided, comprising contacting genomic DNA with a primer pair which amplifies all or part of a mutant WAP7.1 allele and/or of a wild type WAP7.1 allele in the sample, and detecting the amplification products.

Also a method of hybridizing a probe to a mutant and/or wild type WAP7.1 allele in a genomic DNA sample derived from a watermelon plant, plant part or seed is provided, comprising contacting genomic DNA with a oligonucleotide probe which hybridizes to a mutant WAP7.1 allele and/or a wild type WAP7.1 allele in the sample, and detecting the hybridization products.

All embodiments described above and elsewhere herein also apply to these embodiments. The amplification product may thus be a PCR amplification product, e.g. competitive PCR amplification product generated in e.g. a KASP assay or other assay, to detect the mutant allele (or one or two or more mutant alleles) and/or a wild type allele in the DNA sample. The hybridization product may thus be a hybridization product of an oligonucleotide probe which hybridizes to the nucleic acid in the DNA sample, to detect e.g. the mutant and/or wild type allele in the DNA sample. The primer pairs or probes preferably are allele specific, and the products are thus distinguishable as being e.g. either two copies of the wild type allele, two copies of the mutant allele or one copy of each being present in the genomic DNA of the watermelon plant, plant part or seed.

The primers or probes are preferably modified, e.g. labelled by a tail sequence or fluorescent label or otherwise modified with respect to the wild type sequence which they amplify or hybridize.

As the described methods require detection of a mutant and/or wild type allele in the genomic DNA of the plant, plant part or seed, the genomic DNA needs to be accessible for detection, e.g. it may be extracted from the plant cells using DNA extraction methods or at least eluted from the damaged cells into a solution (e.g. a buffer solution).

The above assays can be used for marker assisted selection (MAS) of plants in e.g. a breeding program to select plants comprising a certain genotype, e.g. homozygous for the wild type allele of the WAP7.1 gene, homozygous or heterozygous for a mutant allele of the WAP7.1 allele.

Therefore, also a method of breeding watermelon plants is provided herein, said method comprising genotyping one or more plants for the allele composition at the WAP7.1 locus in the genome and optionally selecting one or more plants having a specific genotype at the WAP7.1 locus. In one aspect also genotyping-by-sequencing may be done for the WAP7.1 gene.

As mentioned, optionally the plants or seeds which comprise two copies of a mutant WAP7.1 allele can be grown and phenotyped for facultative parthenocarpy. The mutant allele is in one aspect a mutant allele which, in homozygous form, confers facultative parthenocarpy.

In a different aspect a watermelon plant, seed or plant part is provided comprising at least one copy of a mutant allele of a gene named ClWAP7.1 in watermelon, wherein said mutant allele either a) comprises one or more mutations in a regulatory element, resulting in no expression or reduced expression of the allele compared to the wild type allele, and/or b) encodes a mutant protein comprising one or more amino acids replaced, inserted, or deleted compared to the wild type protein, wherein said mutant allele of a) or b) confers facultative parthenocarpy when the mutant allele is in homozygous form (compared to the plant comprising the wild type allele in homozygous form), and wherein the wild type watermelon ClWAP7.1 allele encodes a protein of SEQ ID NO: 1 or a protein comprising at least 94%, 95%, 96%, 97%, 98%, 99% or more sequence identity to SEQ ID NO: 1.

Breeding Methods

Further a method of crossing a plant comprising at least one mutant WAP7.1 allele as described herein with a plant, e.g. lacking a mutant WAP7.1 allele, is provided and selecting progeny comprising at least one copy of the mutant WAP7.1 allele is provided.

Thus, in one aspect a method for generating a watermelon plant is provided comprising the steps of:

a) Providing a watermelon plant comprising at least one copy of a mutant WAP7.1 allele, as described;

b) Crossing said watermelon plant with another watermelon plant to produce F1 seeds;

c) Optionally selfing the watermelon plants grown from F1 seeds one or more times to produce F2, F3 or further generation selfing progeny;

d) Crossing said F1 or further generation selfing progeny to the plant of step b), to produce a backcross progeny;

e) Selecting backcross progeny which comprise the mutant WAP7.1 allele of step a).

Optionally the plant of step e) comprises two copies of the mutant WAP7.1 allele and is facultative parthenocarpic.

Optionally selection or detection of the presence of the mutant WAP7.1 allele in any of the steps can be done using molecular methods, such as SNP or INDEL genotyping, sequencing and the like.

Preferably the allele in step a) is a mutant allele which confers facultative parthenocarpy when in homozygous form. In one aspect the plant in step a) is a watermelon plant comprising a mutant allele of Table 1, either in heterozygous or homozygous form.

Also provided is a method for production of a watermelon plant comprising the steps of:

a) introducing mutations in a population of watermelon plants or providing a population of mutagenized watermelon plants, e.g. a TILLING population of the M2, M3 or further generation, b) identifying a plant which has a mutation in an allele encoding a WAP7.1 protein wherein the wild type allele of the gene encodes a WAP7.1 protein comprising at least 94% sequence identity to the protein of SEQ ID NO 1.

The method may further comprise one or both steps of selecting a plant comprising at least two copies of the mutant allele of step b), determining if the plant produces fruits in the absence of pollination.

Further any sequences and molecules of the sequences are encompassed, as are sequences comprising at least 90%, 91%, 92%, 93%, 94%, 95%, 96%, 97%, 98%, 99%, 99.5%, 99.8% or 99.9% sequence identity to the provided sequences. Also, any fragments and/or modified sequences (e.g. primers or probes comprising at least 10, 15, 16, 17, 18, 19, 20 or more nucleotides of the sequence or the complement sequence) and their use inbreeding (e.g. MAS) or in detecting or selecting plants or plant parts is provided.

When a mutant protein is described, it is clear that the genomic sequence and mRNA or cDNA sequence encoding the mutation leading to the mutation in the protein is encompassed herein and can be used to detect an allele in the genome comprising the mutation leading to the amino acid change, and to e.g. carry out a genotyping assay directed at the mutant allele.

Sequence Description

SEQ ID NO 1: wild type WAP7.1 protein of watermelon

SEQ ID NO: 2: mutant WAP7.1 protein of watermelon, comprising a W1054STOP replacement SEQ ID NO: 3: cDNA encoding the wild type WAP7.1 protein SEQ ID NO 4: cDNA encoding the mutant WAP7.1 protein, comprising an A instead of a G at nucleotide 3162, i.e. comprising codon TGA (STOP) instead of codon TGG (W)

SEQ ID NO 5: SNP marker mWM23348403 at nucleotide 51 (G/A) for detecting either the mutant wap7.1 allele or wild type Wap7.1 allele. In the wild type allele the codon TGG encodes W, W1054 of SEQ ID NO: 1. In the mutant allele the G is changed to A (G→A), and the resulting mutated codon TGA is a STOP codon. Thus the SNP marker comprises an A at nucleotide 51 of SEQ ID NO: 5 or at the equivalent nucleotide of a sequence comprising at least 92%, 93%, 94%, 95%, 96%, 97%, 98%, 99% or more sequence identity to SEQ ID NO: 5, can be used to detect the mutant wap7.1 allele, while the SNP marker comprising a G at nucleotide 51 of SEQ ID NO: 5, or at the equivalent nucleotide of a sequence comprising at least 92%, 93%, 94%, 95%, 96%, 97%, 98%, 99% or more sequence identity to SEQ ID NO: 5, can be used to detect the wild type wap7.1 allele SEQ ID NO 6: genomic DNA sequence encoding the wild type WAP7.1 protein SEQ ID NO 7: genomic DNA sequence comprising an A instead of a G at nucleotide 7394, i.e. comprising codon TGA (STOP) instead of codon TGG (W) and encoding the mutant WAP7.1 protein SEQ ID NO 8: amino acid sequence disclosed to be encoded by the gene ClCG07G008850.1

SEQ ID NO 9: amino acid sequence disclosed to be encoded by the gene Cla97C07G135900.1

SEQ ID NO: 10: mutant WAP7.1 protein of watermelon, comprising a Q373STOP replacement SEQ ID NO: 11: mutant WAP7.1 protein of watermelon, comprising a R346K replacement SEQ ID NO: 12: mutant WAP7.1 protein of watermelon, comprising a S324N replacement SEQ ID NO: 13: mutant WAP7.1 protein of watermelon, comprising a P830S replacement SEQ ID NO: 14: mutant WAP7.1 protein of watermelon, comprising a A328T replacement

EXAMPLES

A watermelon mutant population (developed via EMS treatment of an elite line called TY) was screened with a forward screening approach in Chile and one mutant was found which produced fruits without pollination, in an insect proof greenhouse.

A single plant able to produce parthenocarpic fruits was selected and used to make several F2 mapping populations in different genetic backgrounds. The QTL was mapped to a 5.6 Mb/24.6 cM region on chromosome 7. There were 16 mutations within this interval, which all were predicted to be intergenic except one that introduced a premature stop codon in a gene encoding a zinc finger protein in a gene referred to as ClCG07G008850.1.

In the cucurbitgenomics.org database of the Charleston Grey genome the gene was designated ClCG07G008850.1 and was located from nucleotide 23357225 to 23365257 of chromosome 7 (CG_Chr7).

In the cucurbitgenomics.org database of the variety 97103 V2 genome the gene was designated Cla97C07G135900.1 and was located from nucleotide 21927587 to 21935619 of chromosome 7 (Cla97Chr7).

However, despite both genomic sequences being 100% identical, the encoded proteins were described to be different. Using RNA sequence analysis, the correct encoded protein appears to be the protein of SEQ ID NO: 1. In FIG. 3, the differences between the proteins is shown.

The mutant wap7.1 allele was found to be completely unique to this line when it was compared to 93 whole genome re-sequenced lines.

Markers saturating this interval were designed and run on the F2 population. The marker with the highest association with the trait, mWM23348403, was designed to the zinc finger gene. To confirm this mutation, an additional 400 F2 were genotyped with mWM23348403 and flanking markers. The highest associated marker was mWM23348403, which further confirmed the mutation this marker was designed to, was underlying the trait.

The wap7.1 gene is a single recessive gene and the facultative parthenocarpic phenotype co-segregated with the mutant wap7.1 allele in plants homozygous for the mutation (wap7.1/wap7.1).

Based on the knowledge of the WAP7.1 gene, a (EMS induced) mutant watermelon population (also referred to as TILLING population) was screened and plants comprising the mutant alleles shown in Table 1 were identified.

Targeted Mutagenesis

Target-specific genome editing using engineered nucleases has become widespread in various fields. In watermelon Crispr has been successfully used to modify target genes, see e.g. Wang, Y., Wang, J., Guo, S. et al. CRISPR/Cas9-mediated mutagenesis of C1BG1 decreased seed size and promoted seed germination in watermelon. Hortic Res 8, 70

(2021). world wide web at doi.org/10.1038/x41438-021-00506-1, which methods and vectors can also be used to generate mutations in the WAP7.1 gene.

Single-base substitutions or deletions of one or more nucleotides can be performed by homologous recombination (HR).

A binary CRISPR/Cas9 vector can be used, for example as described in Wang et al. (supra). Specific single guide RNAs (sgRNAs) targeted to WAP7.1 can be selected according to the assessment with CRISPR-P (world wide web at cbi.hzau.edu.cn/crispr/). The target sequence is cloned into the vector is then used to transform a watermelon cultivar.

Watermelon explants can be transformed according to a modified method of Yu et al. (2011 Plant Cell Rep 30: 359-371). In brief, surface-sterilized watermelon seeds were sown on basic Murashige and Skoog solid medium supplemented with 3% Suc for 3 d. Then cotyledons without embryo were cut into 2×2 mm pieces. *Agrobacterium tumefaciens* strain EHA105 that harbors the vector can be used for transformation. The cotyledon explants are cocultivated in the dark for 4 d and then transferred onto selective induction medium containing 1.5 mg/L 6 BA, 2 mg/L Basta. The regenerated adventitious buds are excised and transferred onto selective elongation medium, containing 0.1 mg/L 6 BA, 0.01 mg/L NAA, 2 mg/L Basta.

The plasmid vector harbours cassettes expressing CAS9 and two guideRNAs (gRNAs) and a donor fragment as template for homology-directed repair (HDR). Expression of the Cas9 gene and gRNA are driven by a strong promoter, such as a ubiquitin promoter. The gRNAs are be designed at opposite strands of the of the two targeting sites.

The donor fragment contains the desired mutation in the middle of a fragment that corresponds to the sequence of the target WAP7.1 gene (except for the mutation). Optionally, additional synonymous mutations, that do not change amino acid residues in the donor fragment, would prevent Cas9 from cutting the donor fragment again, once HDR is successfully achieved. The fragment is flanked with two gRNA target sequences including the PAM motifs, respectively, so that the donor DNA can be released by Cas9/gRNAs from the plasmid vector; see e.g. Sun et al. (2016) Molecular Plant 9, 628-631 DOI: 10.1016/j.molp.2016.01.001.

To increase HDR, additional free DNA donor fragment can be co-introduced in the explant. After transformation, regenerated shoots selected based on e.g. plasmid vector encoded antibiotics resistance, are grown and analysed for the presence of mutations. This could be done by primers to amplify a target gene sequence from DNA by PCR. Primer are designed so that they cannot amplify a fragment from the plasmid. The amplified product can be sequenced to validate the presence of the mutation.

Plants can be regenerated from transformed plant material comprising the desired mutation using standard methods.

For example as described by Wang et al. (supra), genomic DNA can be extracted from young leaves of T0-T4 transgenic plants, which was then used for creating templates to amplify the specific fragments in the target gene using primers flanking two targeted sites. PCR can be conducted under the following conditions: 94° C./5 min; 94° C./30 s, 56° C./30 s, and 72° C./1 min (35 cycles); and 72° C./10 min as the final extension. PCR products can directly be sequenced used standard methods.

The transgenic plants can also be verified as Cas9-free with primers specific for Cas9. PCR can be conducted under the following conditions: 94° C./5 min; 94° C./30 s, 60° C./30 s, and 72° C./1 min (29 cycles); and 72° C./10 min as the final extension.

The invention claimed is:

1. A watermelon plant or plant part comprising at least one copy of a mutant allele of a gene named Watermelon Parthenocarpy gene on chromosome 7 (WAP7.1), wherein said mutant allele encodes a mutant protein comprising at least 213 amino acids deleted at the C-terminal end of the protein compared to the wild type protein, wherein said mutant allele confers facultative parthenocarpy when the mutant allele is in homozygous form, and wherein the wild type WAP7.1 allele encodes a wild type protein of SEQ ID NO: 1 or a wild type protein comprising at least 94% sequence identity to SEQ ID NO: 1.

2. The watermelon plant or plant part according to claim 1, wherein said mutant allele comprises a mutation in the codon encoding amino acid number W1054 of SEQ ID NO: 1, or the equivalent amino acid in a wild type protein comprising at least 94% identity to SEQ ID NO: 1.

3. The watermelon plant or plant part according to claim 1, wherein said mutant allele has the genomic sequence of SEQ ID NO: 7.

4. The watermelon plant or plant part according to claim 1, wherein the mutant allele is produced by random mutagenesis or targeted mutagenesis.

5. The watermelon plant or plant part according to claim 1, wherein said plant or plant part is diploid and is homozygous for the mutant allele.

6. The watermelon plant or plant part according to claim 1, wherein the plant or plant part is triploid or tetraploid and comprises at least one copy of the mutant allele.

7. The watermelon plant or plant part according to claim 6, wherein the triploid plant or plant part comprises one, two or three copies and the tetraploid plant or plant part comprises two or four copies of the mutant allele.

8. A seed from which a watermelon plant or plant part according to claim 1 can be grown.

9. A fruit produced by a watermelon plant according to claim 1, wherein the fruit is seedless and is produced in the absence of pollination.

10. The watermelon plant part according to claim 1, wherein the plant part is a cell, a flower, a leaf, a stem, a cutting, an ovule, pollen, a root, a rootstock, a scion, a fruit, a protoplast, an embryo, or an anther.

11. A vegetatively propagated plant propagated from a plant part according to claim 10.

12. A method of producing seedless watermelon fruits, said method comprising growing a diploid watermelon plant comprising two copies of a mutant allele according to claim 1, whereby pollination of the flowers is prevented during the growing and harvesting the seedless fruits produced from unpollinated flowers.

13. A method of producing seedless watermelon fruits, said method comprising growing a triploid watermelon plant comprising one, two or three copies of the mutant allele according to claim 1, whereby no pollenizer plant is present during the growing and harvesting the seedless fruits produced from unpollinated flowers.

14. A method for producing a watermelon plant, said method comprising crossing a watermelon plant according to claim 1 with another watermelon plant and selecting a progeny watermelon plant comprising at least one copy of the mutant WAP7.1 allele.

\* \* \* \* \*

SEQUENCE LISTING

<160> NUMBER OF SEQ ID NOS: 14

<210> SEQ ID NO 1
<211> LENGTH: 1266
<212> TYPE: PRT
<213> ORGANISM: artificial
<220> FEATURE:
<223> OTHER INFORMATION: wild type WAP7.1 protein of watermelon

<400> SEQUENCE: 1

```
Met Asp Lys Pro Leu Asp Pro Pro Leu Asp Phe Tyr Lys Pro Arg Leu
1               5                   10                  15

Gln Pro Asp Asp Pro Thr Pro Pro Pro Asp Ala Ser Val Leu Gly
            20                  25                  30

Asn Ser His His Pro Pro His Leu Met Asp Ser His Ile Asp Asp Ser
        35                  40                  45

Lys Leu Val Gly Val Pro Val Ala Gly Pro Leu Leu Pro Ala Asp Ser
    50                  55                  60

Ser Pro Ala Ala Lys Leu Asn Ala Lys Phe Lys Asp Lys Val Leu Val
65                  70                  75                  80

Val Asp Lys Thr Leu Gly Ile Arg Arg Arg Gly Arg Pro Pro Arg Gly
            85                  90                  95

Gln Val Lys Pro Pro Pro Leu Pro Pro Arg Gln Lys Lys Asp Glu Glu
            100                 105                 110

Asp Val Cys Phe Ile Cys Phe Asp Gly Gly Ser Leu Val Leu Cys Asp
            115                 120                 125

Arg Arg Gly Cys Pro Lys Ala Tyr His Pro Ser Cys Ile Lys Arg Asp
        130                 135                 140

Glu Ser Phe Phe Arg Ser Lys Ala Lys Trp Asn Cys Gly Trp His Ile
145                 150                 155                 160

Cys Thr Asn Cys Gln Lys Ala Ser Tyr Tyr Met Cys Tyr Thr Cys Pro
                165                 170                 175

Phe Ser Leu Cys Lys Gly Cys Ile Lys Gly Ala Asp Tyr Gln Cys Val
            180                 185                 190

Arg Gly Thr Lys Gly Phe Cys Gly Thr Cys Met Lys Ile Ile Met Leu
        195                 200                 205

Phe Glu Lys Ser Ala Pro Asp Gly Glu Ser Val Gln Val Asp Phe Asp
    210                 215                 220

Asp Lys Ser Ser Trp Glu Tyr Leu Phe Lys Val Tyr Trp Ile Tyr Leu
225                 230                 235                 240

Lys Glu Lys Leu Ser Leu Thr Val Asp Glu Leu Val Arg Ala Lys Asn
                245                 250                 255

Ser Trp Lys Gly Ser Ile Ile Met Asp His Lys Val Ala Ser Ser Glu
            260                 265                 270

Ile Leu Asp Gly Ser Ile Asp Lys Ser Gln Gly Ala His Asn Ser Phe
        275                 280                 285

Arg Asn Pro Lys Ser Gln Arg Lys Arg Pro Asn Arg Gln Gln Ser Ser
    290                 295                 300

Leu Asn Lys Phe Gly Ser Leu Val Asp Arg Pro Ser Ser Asn Glu Gln
305                 310                 315                 320

Phe Ser Val Ser Thr Lys Trp Ala Thr Thr Glu Leu Met Asp Phe Val
                325                 330                 335

Ala His Val Arg Asn Gly Asp Thr Thr Arg Leu Ser Pro Leu Asp Val
            340                 345                 350

Gln Ala Leu Leu Leu Glu Tyr Val Lys Lys Asn Asn Leu Arg Asp Pro
```

-continued

```
            355                 360                 365

Gln Gln Gln Ser Gln Ile Asn Cys Asp Leu Arg Leu Thr Asn Leu Phe
    370                 375                 380

Gly Lys Ser Arg Ile Gly His Phe Glu Met Leu Asn Leu Leu Gln Ser
385                 390                 395                 400

His Val His Ile Lys Gly Thr Thr Ala Asp Asn Ala Thr Ser Ser Gly
                405                 410                 415

Ala Gly Val Val Ile Asn Pro Val Glu Ser Lys Glu Lys Tyr Asp Cys
                420                 425                 430

Glu Val Val Asp Asp Cys Glu Arg Lys Arg Lys Thr Arg Lys Lys Ala
                435                 440                 445

Asp Glu Ser Arg Gln Gln Leu His Ala Ile Val Asp Glu Tyr Ala Ala
            450                 455                 460

Ile Asp Ile Gln Asn Ile Asn Leu Ile Tyr Leu Arg Arg Asp Leu Ile
465                 470                 475                 480

Val Ser Leu Ile Asp Asp Glu Lys Phe Asn Asp Met Val Ile Gly Ser
                485                 490                 495

Ile Val Arg Ile Gln Ile Pro Asn Asn Asp Glu Lys His Asp Phe His
                500                 505                 510

Arg Leu Val Gln Val Val Gly Ile Ser Lys Ile Ser Thr Pro Tyr Thr
            515                 520                 525

Val Gly Glu Lys Thr Ile Asp Val Met Leu Asp Ile Leu Asn Leu Asp
            530                 535                 540

Lys Arg Glu Ser Val Ser Val Gln Gly Ile Ser Asn Gln Glu Phe Thr
545                 550                 555                 560

Glu Glu Glu Cys Arg Arg Leu Arg Arg Ser Ile Lys Cys Gly Leu Val
                565                 570                 575

Lys Arg Phe Arg Val Ser Glu Ile Leu Asp Lys Gly Arg Glu Leu Gln
                580                 585                 590

Ala Leu Lys Ile Lys Asp Leu Leu Gln Lys Glu Ile Ser Gln Leu Thr
                595                 600                 605

His Leu His Asp Gln Ala Ser Glu Lys Gly Asn Val Asp Glu Leu Arg
            610                 615                 620

Tyr Phe Ala Glu Arg Leu His Arg Leu Lys Ser Pro Glu Glu Cys Gln
625                 630                 635                 640

Arg Arg Leu Leu Glu Ile Leu Glu Val Arg Ser Asp Pro Thr Met Asp
                645                 650                 655

Pro Ser Tyr Glu Ser Glu Glu Asp Lys Asp Glu Ser Asn Lys Lys Arg
                660                 665                 670

Gln Gly Ser Leu Lys Arg Ser Arg Asn Tyr Asp Phe Asp Glu Lys Glu
            675                 680                 685

Val Glu Leu Thr Ser Pro Arg Arg Gly Thr Asn Ser Asn Val Ser Gly
            690                 695                 700

Ser Asp Val Gln Gln Asn Ser Thr Ser Thr Ser Glu Gln Ser Arg Asn
705                 710                 715                 720

Ile Ser Leu Leu Ala His Glu Asn Lys Glu Gly Asp Cys Leu Ala Ser
                725                 730                 735

Asp Arg Thr Gly Glu Thr Ser Trp Ala Gly Arg Gly Leu Val Pro Asn
                740                 745                 750

Asn Trp Asn Val Pro Ser Gln Ala Lys Thr Ala Thr Pro Leu Ser Ser
                755                 760                 765

Asp Gly Asn Tyr Gln Val Val Leu Pro Glu Ala Ser Ile Pro Pro Leu
            770                 775                 780
```

-continued

```
Ser Ile Gly Leu Gly Thr Ser Ser Asn Asp Ala Glu Val Glu Arg Ile
785                 790                 795                 800

Trp Gln Tyr Gln Asp Pro Thr Gly Lys Val Gln Gly Pro Phe Ser Met
            805                 810                 815

Thr Gln Leu Arg Asn Trp Asn Asn Ser Gly His Phe Thr Pro Asp Leu
            820                 825                 830

Arg Val Trp Arg Ile Thr Glu Ser Gln Asn Asp Ala Val Leu Leu Thr
            835                 840                 845

Asn Ala Leu Asn Gly Cys Tyr Thr Lys Ala Ser Ser Ile Trp His Asn
850                 855                 860

Ser His Ile Leu Ser Leu Gly Arg Gly Asn Gly Leu Ser Leu Gly Gly
865                 870                 875                 880

Ser Asp Asn His His Asn Gly Gln Ser Asn Gly Gly Thr Asp Ser Gly
            885                 890                 895

Thr Asn Leu Ile Arg Phe Gly Val Asp Pro Ile Arg Asn Ser Asn Ser
            900                 905                 910

Glu Gln Lys Asp His Ile Ala Val Cys Asp Ala Glu Asn Glu Pro Met
            915                 920                 925

Met Ser Thr Gly Ser Ser Ser Pro Ser Lys Asp Leu Cys Ala Pro Ala
            930                 935                 940

Asp Thr Val Asn Ser Ile Gln Ser Pro Ala Arg Asn Leu Glu Val Ala
945                 950                 955                 960

His Glu Ser Leu Lys Asn Asn Asn Ser Trp Ser Tyr Pro Ser Leu Met
            965                 970                 975

Asn Leu Leu Ser Ser Ala Thr Leu Ser Leu Gln Pro Pro Val Thr Glu
            980                 985                 990

Val His Gln Ala Lys Glu Asn His  Ser Pro Asn Asn Glu  Asp Gln Asn
            995                 1000                1005

Ser Gln  Thr Ile Thr Leu Gly  Gly Ile His Ser Gln  Thr Gly Arg
    1010                1015                1020

Lys Lys  Arg Ser Ser Ser Glu  Asp Cys Ser Ser Gln  Ser Ser Gly
    1025                1030                1035

Gln Asn  Trp Ile Ala Pro Pro  Ala Thr Asp Thr Ser  Ser Arg Glu
    1040                1045                1050

Trp Asn  Ser Asn Cys Ser Gly  Leu Ser Leu Met Asp  Ser Phe Lys
    1055                1060                1065

Pro Ser  Glu Lys Ile Gly Glu  Ile Leu Pro Asp Ile  Pro His Ser
    1070                1075                1080

Thr Leu  Lys Pro Val Thr Ala  Asp Ala Glu Ile Lys  Gln Ser Ala
    1085                1090                1095

Ser Ser  Ser Val Leu Val Gln  Asn Ser Gly Leu Ser  Trp Ser Ser
    1100                1105                1110

Ala Ser  Ser Leu Pro Gly Gly  Arg Gln Leu Pro Ser  His Val Ala
    1115                1120                1125

Ala Gly  Ala Trp Gly Gly Gly  Tyr Leu Ala Ala Pro  Gly Arg Ala
    1130                1135                1140

Ile Glu  Asp Leu Asn Ser Ser  Phe Ile Thr Ala Ser  Gly Met Lys
    1145                1150                1155

Ser Ser  Asp Ile Ile Asp Asp  His Glu Thr Thr Gly  Ala Thr Ile
    1160                1165                1170

Asn Trp  Ile Asp Asp Glu Pro  Asn Asp Phe Asn Ser  Leu Val Asp
    1175                1180                1185
```

-continued

```
Glu Ser  Val Ser Asp Leu Leu  Ala Glu Val Glu Ala  Met Glu Cys
    1190             1195             1200

Leu Ser  Gly Leu Ala Ser Thr  Ala Ser Met Met Asn  Cys Asn Glu
    1205             1210             1215

Gly Leu  Thr Arg Asp Ser Arg  Ser Asp Cys Phe Phe  Ser Val Asp
    1220             1225             1230

Gly Phe  Asn Pro Ala Ala Glu  Met Gly Lys Val Asp  Ala Leu Ser
    1235             1240             1245

Ser Thr  Ala Asn Leu Gln Phe  Pro Phe Asn Ile Lys  Val Lys Asp
    1250             1255             1260

Glu Gln  Pro
    1265

<210> SEQ ID NO 2
<211> LENGTH: 1053
<212> TYPE: PRT
<213> ORGANISM: artificial
<220> FEATURE:
<223> OTHER INFORMATION: mutant WAP7.1 protein

<400> SEQUENCE: 2

Met Asp Lys Pro Leu Asp Pro Pro Leu Asp Phe Tyr Lys Pro Arg Leu
1               5               10              15

Gln Pro Asp Asp Pro Thr Pro Pro Pro Asp Ala Ser Val Leu Gly
        20              25              30

Asn Ser His His Pro Pro His Leu Met Asp Ser His Ile Asp Asp Ser
        35              40              45

Lys Leu Val Gly Val Pro Val Ala Gly Pro Leu Leu Pro Ala Asp Ser
    50              55              60

Ser Pro Ala Ala Lys Leu Asn Ala Lys Phe Lys Asp Lys Val Leu Val
65              70              75              80

Val Asp Lys Thr Leu Gly Ile Arg Arg Arg Gly Arg Pro Pro Arg Gly
            85              90              95

Gln Val Lys Pro Pro Pro Leu Pro Pro Arg Gln Lys Lys Asp Glu Glu
            100             105             110

Asp Val Cys Phe Ile Cys Phe Asp Gly Gly Ser Leu Val Leu Cys Asp
            115             120             125

Arg Arg Gly Cys Pro Lys Ala Tyr His Pro Ser Cys Ile Lys Arg Asp
        130             135             140

Glu Ser Phe Phe Arg Ser Lys Ala Lys Trp Asn Cys Gly Trp His Ile
145             150             155             160

Cys Thr Asn Cys Gln Lys Ala Ser Tyr Tyr Met Cys Tyr Thr Cys Pro
                165             170             175

Phe Ser Leu Cys Lys Gly Cys Ile Lys Gly Ala Asp Tyr Gln Cys Val
            180             185             190

Arg Gly Thr Lys Gly Phe Cys Gly Thr Cys Met Lys Ile Ile Met Leu
            195             200             205

Phe Glu Lys Ser Ala Pro Asp Gly Glu Ser Val Gln Val Asp Phe Asp
            210             215             220

Asp Lys Ser Ser Trp Glu Tyr Leu Phe Lys Val Tyr Trp Ile Tyr Leu
225             230             235             240

Lys Glu Lys Leu Ser Leu Thr Val Asp Glu Leu Val Arg Ala Lys Asn
            245             250             255

Ser Trp Lys Gly Ser Ile Ile Met Asp His Lys Val Ala Ser Ser Glu
            260             265             270
```

-continued

```
Ile Leu Asp Gly Ser Ile Asp Lys Ser Gln Gly Ala His Asn Ser Phe
        275             280             285

Arg Asn Pro Lys Ser Gln Arg Lys Arg Pro Asn Arg Gln Gln Ser Ser
    290             295             300

Leu Asn Lys Phe Gly Ser Leu Val Asp Arg Pro Ser Ser Asn Glu Gln
305             310             315             320

Phe Ser Val Ser Thr Lys Trp Ala Thr Thr Glu Leu Met Asp Phe Val
            325             330             335

Ala His Val Arg Asn Gly Asp Thr Thr Arg Leu Ser Pro Leu Asp Val
            340             345             350

Gln Ala Leu Leu Leu Glu Tyr Val Lys Lys Asn Asn Leu Arg Asp Pro
    355             360             365

Gln Gln Gln Ser Gln Ile Asn Cys Asp Leu Arg Leu Thr Asn Leu Phe
    370             375             380

Gly Lys Ser Arg Ile Gly His Phe Glu Met Leu Asn Leu Leu Gln Ser
385             390             395             400

His Val His Ile Lys Gly Thr Thr Ala Asp Asn Ala Thr Ser Ser Gly
            405             410             415

Ala Gly Val Val Ile Asn Pro Val Glu Ser Lys Glu Lys Tyr Asp Cys
            420             425             430

Glu Val Val Asp Asp Cys Glu Arg Lys Arg Lys Thr Arg Lys Lys Ala
            435             440             445

Asp Glu Ser Arg Gln Gln Leu His Ala Ile Val Asp Glu Tyr Ala Ala
    450             455             460

Ile Asp Ile Gln Asn Ile Asn Leu Ile Tyr Leu Arg Arg Asp Leu Ile
465             470             475             480

Val Ser Leu Ile Asp Asp Glu Lys Phe Asn Asp Met Val Ile Gly Ser
            485             490             495

Ile Val Arg Ile Gln Ile Pro Asn Asn Asp Glu Lys His Asp Phe His
            500             505             510

Arg Leu Val Gln Val Val Gly Ile Ser Lys Ile Ser Thr Pro Tyr Thr
            515             520             525

Val Gly Glu Lys Thr Ile Asp Val Met Leu Asp Ile Leu Asn Leu Asp
    530             535             540

Lys Arg Glu Ser Val Ser Val Gln Gly Ile Ser Asn Gln Glu Phe Thr
545             550             555             560

Glu Glu Glu Cys Arg Arg Leu Arg Arg Ser Ile Lys Cys Gly Leu Val
            565             570             575

Lys Arg Phe Arg Val Ser Glu Ile Leu Asp Lys Gly Arg Glu Leu Gln
            580             585             590

Ala Leu Lys Ile Lys Asp Leu Leu Gln Lys Glu Ile Ser Gln Leu Thr
            595             600             605

His Leu His Asp Gln Ala Ser Glu Lys Gly Asn Val Asp Glu Leu Arg
    610             615             620

Tyr Phe Ala Glu Arg Leu His Arg Leu Lys Ser Pro Glu Glu Cys Gln
625             630             635             640

Arg Arg Leu Leu Glu Ile Leu Glu Val Arg Ser Asp Pro Thr Met Asp
            645             650             655

Pro Ser Tyr Glu Ser Glu Glu Asp Lys Asp Glu Ser Asn Lys Lys Arg
            660             665             670

Gln Gly Ser Leu Lys Arg Ser Arg Asn Tyr Asp Phe Asp Glu Lys Glu
            675             680             685

Val Glu Leu Thr Ser Pro Arg Arg Gly Thr Asn Ser Asn Val Ser Gly
```

-continued

```
        690              695              700
Ser Asp Val Gln Gln Asn Ser Thr Ser Thr Ser Glu Gln Ser Arg Asn
705              710              715              720

Ile Ser Leu Leu Ala His Glu Asn Lys Glu Gly Asp Cys Leu Ala Ser
              725              730              735

Asp Arg Thr Gly Glu Thr Ser Trp Ala Gly Arg Gly Leu Val Pro Asn
              740              745              750

Asn Trp Asn Val Pro Ser Gln Ala Lys Thr Ala Thr Pro Leu Ser Ser
              755              760              765

Asp Gly Asn Tyr Gln Val Val Leu Pro Glu Ala Ser Ile Pro Pro Leu
              770              775              780

Ser Ile Gly Leu Gly Thr Ser Ser Asn Asp Ala Glu Val Glu Arg Ile
785              790              795              800

Trp Gln Tyr Gln Asp Pro Thr Gly Lys Val Gln Gly Pro Phe Ser Met
              805              810              815

Thr Gln Leu Arg Asn Trp Asn Asn Ser Gly His Phe Thr Pro Asp Leu
              820              825              830

Arg Val Trp Arg Ile Thr Glu Ser Gln Asn Asp Ala Val Leu Leu Thr
              835              840              845

Asn Ala Leu Asn Gly Cys Tyr Thr Lys Ala Ser Ser Ile Trp His Asn
              850              855              860

Ser His Ile Leu Ser Leu Gly Arg Gly Asn Gly Leu Ser Leu Gly Gly
865              870              875              880

Ser Asp Asn His His Asn Gly Gln Ser Asn Gly Gly Thr Asp Ser Gly
              885              890              895

Thr Asn Leu Ile Arg Phe Gly Val Asp Pro Ile Arg Asn Ser Asn Ser
              900              905              910

Glu Gln Lys Asp His Ile Ala Val Cys Asp Ala Glu Asn Glu Pro Met
              915              920              925

Met Ser Thr Gly Ser Ser Ser Pro Ser Lys Asp Leu Cys Ala Pro Ala
930              935              940

Asp Thr Val Asn Ser Ile Gln Ser Pro Ala Arg Asn Leu Glu Val Ala
945              950              955              960

His Glu Ser Leu Lys Asn Asn Asn Ser Trp Ser Tyr Pro Ser Leu Met
              965              970              975

Asn Leu Leu Ser Ser Ala Thr Leu Ser Leu Gln Pro Pro Val Thr Glu
              980              985              990

Val His Gln Ala Lys Glu Asn His  Ser Pro Asn Asn Glu  Asp Gln Asn
              995              1000              1005

Ser Gln  Thr Ile Thr Leu Gly  Gly Ile His Ser Gln  Thr Gly Arg
      1010              1015              1020

Lys Lys  Arg Ser Ser Ser Glu  Asp Cys Ser Ser Gln  Ser Ser Gly
      1025              1030              1035

Gln Asn  Trp Ile Ala Pro Pro  Ala Thr Asp Thr Ser  Ser Arg Glu
      1040              1045              1050
```

<210> SEQ ID NO 3
<211> LENGTH: 3801
<212> TYPE: DNA
<213> ORGANISM: artificial
<220> FEATURE:
<223> OTHER INFORMATION: cDNA encoding wild type WAP7.1 protein of SEQ
      ID NO: 1

<400> SEQUENCE: 3

-continued

```
atggacaaac ccctcgatcc gcctttggat ttctacaaac cccgtcttca acccgatgac     60
cctactccgc cgcctccaga cgcctccgtt ttggggaatt ctcatcaccc tccccacctc    120
atggactccc atatcgacga ttccaagctg gttggagttc cagtcgctgg acccctcctt    180
cctgccgatt cttcacccgc cgctaagctg aatgctaaat tcaaggacaa ggttcttgtt    240
gtcgacaaaa ctctcgggat tcgccgacga ggtcgtcctc ctcgtggtca agtcaagccc    300
cccccgttac cgccgagaca aaagaaggat gaggaggatg tgtgttttat atgctttgat    360
ggtggcagcc ttgttctctg tgatcgccga gggtgtccaa aggcttatca tccatcatgc    420
attaagcgag atgagtcatt ctttcgatcc aaggctaaat ggaattgtgg atggcacata    480
tgcacaaatt gccagaaggc ttcatattat atgtgctata catgcccgtt ttctctgtgc    540
aagggatgca ttaaaggtgc tgattaccag tgtgttaggg gaaccaaagg gttctgtgga    600
acttgtatga aaataataat gctgttcgag aaaagcgcac ctgacggaga atcggtccaa    660
gtcgattttg atgataaaag tagctgggag tatcttttta aagtgtattg gatttacttg    720
aaagaaaaac tctctttaac tgtggatgaa ctcgttcgtg ctaagaattc atggaaagga    780
agcattatca tggaccataa ggtggcttcc agtgagattc tcgatggcag tattgataaa    840
agccaaggag ctcataattc atttagaaac ccaaaatcac aaaggaaaag gcctaacagg    900
caacaaagct ctctgaataa attcggctcc ttagtggaca ggccaagtag taatgagcaa    960
ttttctgtta gcacaaaatg ggcaactaca gagctcatgg actttgttgc ccatgtgaga   1020
aatggtgaca cgacaaggct ttcaccattg gatgtacaag ctttactgct ggagtatgtg   1080
aagaaaaata atcttcgtga tcctcaacag caatcccaaa ttaattgtga tttgaggctt   1140
accaatctat ttgggaaatc acggataggt cactttgaga tgctaaatct tcttcaatct   1200
catgtgcaca taaaaggaac tacagctgat aatgcaacca gctcaggtgc tggtgtagtg   1260
atcaatccag ttgaaagcaa agagaagtat gattgtgaag tagtggatga ttgtgaaaga   1320
aagcgtaaaa cacgcaagaa agctgatgag agcaggcagc aattgcatgc aattgtggat   1380
gaatatgccg caattgacat tcaaaacatt aacttgattt acttgcggcg tgatctgata   1440
gtgagcctca ttgatgatga aaaatttaat gacatggtta taggctctat tgtgagaata   1500
cagattccaa ataatgatga aaaacatgat tttcataggc ttgtccaagt tgtaggcata   1560
agcaagatct ctacaccata cacagtcggt gagaaaacaa ttgatgtgat gcttgatata   1620
ttgaacttgg acaagagaga gtcggtgtct gttcagggga tttctaacca agaatttact   1680
gaggaagaat gcaggcgtct acgccggagc ataaagtgtg ggcttgtcaa acgattcaga   1740
gttagtgaaa ttctggacaa aggaagggaa cttcaagcat tgaagattaa ggatctgctc   1800
caaaaagaga tctctcaact cactcacctc cacgatcaag caagtgagaa gggcaacgtg   1860
gatgaactaa gatattttgc ggagaggtta catcgtctga aatcacctga agaatgccag   1920
cgtaggcttc ttgaaattct tgaagtacgt tctgatccaa ctatggatcc gagttacgag   1980
tctgaagaag ataaggatga atcaaacaag aaaagacaag gaagtctcaa gagatctaga   2040
aattatgact tcgatgaaaa agaggtggag cttacctcac cacgaagagg aaccaattca   2100
aatgttagtg gaagtgatgt acagcaaaat tcgactagta cttcagagca aagtagaaat   2160
attagcttac ttgctcacga gaataaagaa ggtgactgct tggccagtga caggaccggt   2220
gaaacgtcgt gggcaggaag aggtcttgta ccaaataatt ggaatgtacc tagtcaggct   2280
aaaactgcca ctcctttgtc ctctgatggg aattaccaag tggtcttacc tgaagcctca   2340
attccgccac tttctattgg gttaggaact tcttctaatg atgcagaagt ggaaaggata   2400
```

-continued

```
tggcaatacc aggatccgac tggaaaagtt cagggtccat tttctatgac gcagttacgc    2460
aattggaaca atagtggaca cttcactcct gatcttagag tatggaggat aactgaatca    2520
caaaatgacg ctgtactgtt aaccaatgca ttaaatggat gttacaccaa agcatcttcc    2580
atttggcaca acagtcatat tctgagtcta gggcgaggaa atggactttc tttgggtggt    2640
tcagataatc atcataatgg tcaaagtaat ggaggtactg attctggtac aaatttaatt    2700
cggtttggcg tggatcctat caggaatagc aattctgagc agaaagatca tattgcagtt    2760
tgtgatgctg aaaatgagcc catgatgagc actggttcaa gctcaccttc taaagatttg    2820
tgtgcacctg cagacactgt caactctatt cagtctccag ctaggaacct tgaggtagca    2880
cacgagtcat tgaagaacaa taattcgtgg tcctacccat cccttatgaa tttactttca    2940
tcagcgacgt tatctttaca accacctgta actgaagtcc atcaggctaa ggaaaaccac    3000
agccctaata acgaggatca gaattcacag accattactt tgggaggaat tcatagtcaa    3060
accggtcgca agaaacggtc tagtagtgag gattgttcta gtcaatcttc agggcaaaac    3120
tggatcgctc cacctgcaac ggatacttcc tctcgtgaat ggaactctaa ttgtagtggt    3180
ctttctttga tggattcatt caagccatca gagaaaattg gagaaatttt acctgatatt    3240
cctcattcta ccctgaaacc ggtgactgca gatgctgaaa ttaaacaatc tgcatcttca    3300
agtgttcttg ttcagaattc tggccttagc tggagtagcg cctcaagttt accgggtgga    3360
cgacagcttc ctagtcatgt agcagcgggt gcttggggg gtgggtattt ggctgcacca    3420
ggtagagcaa ttgaggactt gaactccagt ttcataactg catctggtat gaaatcatct    3480
gatataatcg acgatcacga gacaactggg gctacaataa attggattga tgatgaaccc    3540
aatgacttca attccttggt cgatgaatct gtctcagatt tgttagcaga agttgaagca    3600
atggaatgct tgagtggttt ggcttccaca gcatcgatga tgaattgtaa cgagggatta    3660
actcgggatt ctagaagtga ttgtttttc tcagtcgatg gtttcaatcc agcagctgag    3720
atggggaagg tggatgcatt aagctccaca gccaatttgc agtttccatt taacatcaaa    3780
gtgaaagatg agcaaccttg a                                                 3801
```

<210> SEQ ID NO 4
<211> LENGTH: 3801
<212> TYPE: DNA
<213> ORGANISM: artificial
<220> FEATURE:
<223> OTHER INFORMATION: cDNA encoding mutant protein of SEQ ID NO: 2

<400> SEQUENCE: 4

```
atggacaaac ccctcgatcc gcctttggat ttctacaaac cccgtcttca acccgatgac      60
cctactccgc cgcctccaga cgcctccgtt ttggggaatt ctcatcaccc tccccacctc     120
atggactccc atatcgacga ttccaagctg gttggagttc cagtcgctgg accccctcctt     180 cctgccgatt cttcacccgc cgctaagctg aatgctaaat caaggacaa ggttcttgtt      240 gtcgacaaaa ctctcgggat tcgccgacga ggtcgtcctc ctcgtggtca agtcaagccc     300
cccccgttac cgccgagaca aaagaaggat gaggaggatg tgtgttttat atgctttgat     360
ggtggcagcc ttgttctctg tgatcgccga gggtgtccaa aggcttatca tccatcatgc     420
attaagcgag atgagtcatt ctttcgatcc aaggctaaat ggaattgtgg atggcacata     480
tgcacaaatt gccagaaggc ttcatattat atgtgctata catgcccgtt ttctctgtgc     540
aagggatgca ttaaaggtgc tgattaccag tgtgttaggg gaaccaaagg gttctgtgga     600
```

-continued

```
acttgtatga aaataataat gctgttcgag aaaagcgcac ctgacggaga atcggtccaa        660
gtcgattttg atgataaaag tagctgggag tatcttttta aagtgtattg gatttacttg        720
aaagaaaaac tctctttaac tgtggatgaa ctcgttcgtg ctaagaattc atggaaagga        780
agcattatca tggaccataa ggtggcttcc agtgagattc tcgatggcag tattgataaa        840
agccaaggag ctcataattc atttagaaac ccaaaatcac aaaggaaaag gcctaacagg        900
caacaaagct ctctgaataa attcggctcc ttagtggaca ggccaagtag taatgagcaa        960
ttttctgtta gcacaaaatg ggcaactaca gagctcatgg actttgttgc ccatgtgaga       1020
aatggtgaca cgacaaggct ttcaccattg gatgtacaag ctttactgct ggagtatgtg       1080
aagaaaaata atcttcgtga tcctcaacag caatcccaaa ttaattgtga tttgaggctt       1140
accaatctat ttgggaaatc acggataggt cactttgaga tgctaaatct tcttcaatct       1200
catgtgcaca taaaaggaac tacagctgat aatgcaacca gctcaggtgc tggtgtagtg       1260
atcaatccag ttgaaagcaa agagaagtat gattgtgaag tagtggatga ttgtgaaaga       1320
aagcgtaaaa cacgcaagaa agctgatgag agcaggcagc aattgcatgc aattgtggat       1380
gaatatgccg caattgacat tcaaaacatt aacttgattt acttgcggcg tgatctgata       1440
gtgagcctca ttgatgatga aaaatttaat gacatggtta taggctctat tgtgagaata       1500
cagattccaa ataatgatga aaaacatgat tttcataggc ttgtccaagt tgtaggcata       1560
agcaagatct ctacaccata cacagtcggt gagaaaacaa ttgatgtgat gcttgatata       1620
ttgaacttgg acaagagaga gtcggtgtct gttcagggga tttctaacca agaatttact       1680
gaggaagaat gcaggcgtct acgccggagc ataaagtgtg ggcttgtcaa acgattcaga       1740
gttagtgaaa ttctggacaa aggaagggaa cttcaagcat tgaagattaa ggatctgctc       1800
caaaaagaga tctctcaact cactcacctc cacgatcaag caagtgagaa gggcaacgtg       1860
gatgaactaa gatattttgc ggagaggtta catcgtctga aatcacctga agaatgccag       1920
cgtaggcttc ttgaaattct tgaagtacgt tctgatccaa ctatggatcc gagttacgag       1980
tctgaagaag ataaggatga atcaaacaag aaaagacaag gaagtctcaa gagatctaga       2040
aattatgact tcgatgaaaa agaggtggag cttacctcac cacgaagagg aaccaattca       2100
aatgttagtg gaagtgatgt acagcaaaat tcgactagta cttcagagca aagtagaaat       2160
attagcttac ttgctcacga gaataaagaa ggtgactgct tggccagtga caggaccggt       2220
gaaacgtcgt gggcaggaag aggtcttgta ccaaataatt ggaatgtacc tagtcaggct       2280
aaaactgcca ctcctttgtc ctctgatggg aattaccaag tggtcttacc tgaagcctca       2340
attccgccac tttctattgg gttaggaact tcttctaatg atgcagaagt ggaaaggata       2400
tggcaatacc aggatccgac tggaaaagtt cagggtccat tttctatgac gcagttacgc       2460
aattggaaca atagtggaca cttcactcct gatcttagag tatggaggat aactgaatca       2520
caaaatgacg ctgtactgtt aaccaatgca ttaaatggat gttacaccaa agcatcttcc       2580
atttggcaca acagtcatat tctgagtcta gggcgaggaa atggactttc tttgggtggt       2640
tcagataatc atcataatgg tcaaagtaat ggaggtactg attctggtac aaatttaatt       2700
cggtttggcg tggatcctat caggaatagc aattctgagc agaaagatca tattgcagtt       2760
tgtgatgctg aaaatgagcc catgatgagc actggttcaa gctcaccttc taaagatttg       2820
tgtgcacctg cagacactgt caactctatt cagtctccag ctaggaacct tgaggtagca       2880
cacgagtcat tgaagaacaa taattcgtgg tcctacccat cccttatgaa tttactttca       2940
tcagcgacgt tatctttaca accacctgta actgaagtcc atcaggctaa ggaaaaccac       3000
```

```
agccctaata acgaggatca gaattcacag accattactt tgggaggaat tcatagtcaa      3060
accggtcgca agaaacggtc tagtagtgag gattgttcta gtcaatcttc agggcaaaac      3120
tggatcgctc cacctgcaac ggatacttcc tctcgtgaat gaaactctaa ttgtagtggt      3180
ctttctttga tggattcatt caagccatca gagaaaattg gagaaatttt acctgatatt      3240
cctcattcta ccctgaaacc ggtgactgca gatgctgaaa ttaaacaatc tgcatcttca      3300
agtgttcttg ttcagaattc tggccttagc tggagtagcg cctcaagttt accgggtgga      3360
cgacagcttc ctagtcatgt agcagcgggt gcttgggggg gtgggtattt ggctgcacca      3420
ggtagagcaa ttgaggactt gaactccagt ttcataactg catctggtat gaaatcatct      3480
gatataatcg acgatcacga dacaactggg gctacaataa attggattga tgatgaaccc      3540
aatgacttca attccttggt cgatgaatct gtctcagatt tgttagcaga agttgaagca      3600
atggaatgct tgagtggttt ggcttccaca gcatcgatga tgaattgtaa cgagggatta      3660
actcgggatt ctagaagtga ttgtttttttc tcagtcgatg gtttcaatcc agcagctgag      3720
atggggaagg tggatgcatt aagctccaca gccaatttgc agtttccatt taacatcaaa      3780
gtgaaagatg agcaaccttg a                                               3801
```

<210> SEQ ID NO 5
<211> LENGTH: 101
<212> TYPE: DNA
<213> ORGANISM: artificial
<220> FEATURE:
<223> OTHER INFORMATION: marker mWM23348403
<220> FEATURE:
<221> NAME/KEY: [G/A] SNP
<222> LOCATION: (51)..(51)

<400> SEQUENCE: 5

```
gggcaaaact ggatcgctcc acctgcaacg gatacttcct ctcgtgaatg aaactctaat       60
tgtagtggtc tttctttgat ggattcattc aagccatcag a                         101
```

<210> SEQ ID NO 6
<211> LENGTH: 8033
<212> TYPE: DNA
<213> ORGANISM: artificial
<220> FEATURE:
<223> OTHER INFORMATION: wild type WAP7.1 genomic sequence

<400> SEQUENCE: 6

```
atggacaaac ccctcgatcc gcctttggat ttctacaaac cccgtcttca acccgatgac       60
cctactccgc cgcctccaga cgcctccgtt ttggggaatt ctcatcaccc tccccacctc      120
atggactccc atatcgacga ttccaagctg gttggagttc cagtcgctgg acccctcctt      180
cctgccgatt cttcacccgc cgctaagctg aatgctaaat tcaaggacaa ggttcttgtt      240
gtcgacaaaa ctctcgggat tcgccgacga ggtcgtcctc ctcgtggtca agtcaagccc      300
cccccgttac cgccgagaca aaagaaggat gaggaggatg tgtgtttttat atgctttgat      360 ggtggcagcc ttgttctctg tgatcgccgg tgagtggact ttgtttgtgc aaatttgttg      420
tgtggcttgc cgcaagtttc ggggacgatg agagattttt tttcccccctc tactttggat      480 ttatggaatc tttgctttgc gcgttcgcct tttatttagg gaattccgtc tcgatcacac      540
ttgagcttgt tgattagttg tagctattta agcggagatt cgctgttaa tataatacgt       600 tgctccaatg aatttatctt gatttagttg aggtgaagga cacggaaata gtaattcttt      660
aattttgtac atctaaggtg agagaaaatt ttccttattt gagcgtaata ttacaatttc      720
```

-continued

```
acctcaattg tttcccattt cgttgtctct tactctttgc atgttctggg ttgtggtata     780
tttgattcgt tccccttaag aaatggtttt catttattgt tatttgacag agggtgtcca     840
aaggcttatc atccatcatg cattaagcga gatgagtcat tctttcgatc caaggctaaa     900
tggaattgtg gtacgtagct ttgtgttttt ggttgttctc cggctgttac ttactgcact     960
gcactcgact gtggatgtca gtataatatt tattttctac ccaatattca ctatcgttta    1020
gaattcaaga tgcaatcttt tttcatcgtt gtgcaggatg gcacatatgc acaaattgcc    1080
agaaggcttc atattatatg tgctatacat gcccgttttc tctgtgcaag ggatgcatta    1140
aaggtgctga ttaccagtgt gttaggggaa ccaaagggtt ctgtggaact tgtatgaaaa    1200
taataatgct gttcgagaaa agcgcacctg acggagaatc ggtatgaaaa aattcgatgt    1260
tgtcttcctg tctatgcatg tatgacattc tattatttat ttctcaagtc tacttatact    1320
tccaattcga tagtggataa tatgaagaaa ttcattcatc atgtggtata tgcatgcaca    1380
ctcaagaaaa tccttctttg ctttccgttt cactcaagtg attcttggtt tgagattcac    1440
attccatctt tttatttgcc tggcgataaa ttcatctagt cgttcggagt atcgtttttg    1500
tttttggacc tggctattaa atgcatatat tagccatttt ctgtacgtca gtttctaatt    1560
tatgccttct atgttgtttc taacatccaa taaattgttc ttaaaatatg caggtccaag    1620
tcgattttga tgataaaagt agctgggagt atcttttaa agtgtattgg atttacttga    1680
aagaaaaact ctctttaact gtggatgaac tcgttcgtgc taagaattca tggaaaggaa    1740
gcattatcat ggaccataag gtggcttcca gtgagattct cgatggcagt attgataaaa    1800
gccaaggagc tcataattca tttagaaacc caaaatcaca aaggaaaagg cctaacaggc    1860
aacaaagctc tctgaataaa ttcggctcct tagtggacag gccaagtagt aatgagcaat    1920
tttctgttag cacaaaatgg gcaactacag agctcatgga ctttgttgcc catgtgagaa    1980
atggtgacac gacaaggctt tcaccattgg atgtacaagc tttactgctg gagtatgtga    2040
agaaaaataa tcttcgtgat cctcaacagc aatcccaaat taattgtgat ttgaggctta    2100
ccaatctatt tgggaaatca cggataggtc actttgagat gctaaatctt cttcaatctc    2160
atgtgcacat aaaaggaact acagctgata atgcaaccag ctcaggtgct ggtgtagtga    2220
tcaatccagt tgaaagcaaa gagaagtatg attgtgaagt agtggatgat tgtgaaagaa    2280
agcgtaaaac acgcaagaaa gctgatgaga gcaggcagca attgcatgca attgtggatg    2340
aatatgccgc aattgacatt caaaacatta acttgattta cttgcggcgt gatctgatag    2400
tgagcctcat tgatgatgaa aaatttaatg acatggttat aggctctatt gtgagaatac    2460
agattccaaa taatgatgaa aaacatgatt tcataggct tgtccaagtt gtaggtatta    2520
atatctaata ttaatgcttg atatgacata caatgatata tacatatttt taccctcgat    2580
cttaacattt tgcatatgtg tttaggcata agcaagatct ctacaccata cacagtcggt    2640
gagaaaacaa ttgatgtgat gcttgatata ttgaacttgg acaagagaga gtcggtgtct    2700
gttcagggga tttctaacca agaatttact gaggttatta aacttacctt attaattgaa    2760
aatgatagtt tcgtcgatct ctggtttaca tggctagttt gatgtcagtg actgatttta    2820
taatggtggt tacatagttt ctattatttt tatgcaagtt aaattcaatt attatgctta    2880
agtccgcaat tgctttggtt ttgtagttga tttgtttgtc tgttcagaat gtctacagaa    2940
catgctacat cttacggtct cacgggtttg cttctagttt aggccatatt gaagtagata    3000
acggttccac acattctaag ttggacccctt gcctcattct caggatttttc tcaaattgtt    3060
```

-continued

```
ttctaaaata taatgatggg gaggaaaagc ccatatttat tatttccaca tgtttagttt   3120
ttttgattgg tttctcatct cttttgattt ccgaagagag attgaattat catttctgtt   3180
ggagaccgaa tgggatgttg attaagaaac tcaacaaaca aaatgaacta attttgggt    3240 tagagaactt tttatgtaaa gctaattgct cggaaatgca actacatgtt tctggctcaa   3300
aacagggaaa aaagaaaaaa gacaccaact taagcaatgt ttgagatact ttttatacaa   3360
gtcatccctc aaatctttc tttgcagtat gattgtgatt ttgaagttcg tgtatcatct     3420
ttatattggc ttcttttgat caaaagagtg gtattgatgg ttggtggtcc cctctttcag   3480
ttgatatgta atgtgatgga catgctactt gtgtcattgt taattttct aagaaatgcg     3540 tgcatgcatt ttacccttcc agtattgatg tattagtata tactcaggaa gaatgcaggc   3600
gtctacgccg gagcataaag tgtgggcttg tcaaacgatt cagagttgta agattacata   3660
tccatagatt ttttatatt tcaacctatt tagctgttgt gcctttaact cctatacagc     3720
ttgtgttgtt tatagaaatt tttgttttg actgcagagt gaaattctgg acaaaggaag     3780
ggaacttcaa gcattgaaga ttaaggatgt gagttcaacc ccacttttgt caatcatgag   3840
actcaattac attctgcttt ggtttttttt tcttttcttt ttttgggtgt gtttctcttt   3900
ttgggggttt agaaattaga gtttatccat cttgaaagca atcagataaa acaaatacca   3960
gagtctaaag actattctcg attctcgaac taatgataat tcagaataac tcacgtccca   4020
taccacacat ctttggtgta tcacatctat cttttgacatc agataggatg cagtagtatc  4080
ttacacgctg tgatgttgaa gtagtgggag tggcttagaa gttagaatca gatctttaat   4140
gaaattttgc attaaaaagg ccaaacccccc caaaaaaaag ggccaaacca aggccacaaa  4200
aggtcaacct ccgcccaaaa ccagatcttt agtgaaaata aacttgcata aattcccatt   4260
atatttggat aggttctatt taaaatggaa aattagttta atcaattttt atatatgata   4320
tttttcttac tcgaaatacc aagcaaacat ctgataattt gagagaggct tcccatccat   4380
ctttgttatt atcctttttt ttttctggga ggggggttctc cctactgccc cgcccctatg  4440
ttgttctctc tctttccttt gattaactcc acatcgtttc ttatctaaaa aaatatagat   4500
aaagaaatag caagcgaacc tcattagaat actttcctga atttttcatc cttatttttc   4560
ttaaccaaaa atatgttcaa ctatttatga gacgatcaac taagtctaag ttgtatgaaa    4620
ttcctttttt tattttttta tttaattttt ttagattaag tttccaacta ttactaaaag   4680 aggggggctaa accatatgat atgttttttt ggataagaaa accatatgat atgttatag a 4740 ttagtagatt acaattatag atgagatgcc taggacttta acatgtatta catagatgga   4800
aactggaata tatgttttga agaaattaat atgcctgata aatcttcttt tcatttaata   4860
gtatttatga tgccaatatg tgagtcctct ctctgtctct gtctttcttt ctttctttct   4920
tctagggtga tgattgctat gaactgaagt ttacataatc actaaatgat taattcttgg   4980
cctagacaat gttgcaaaga caatgatatg tcatacagaa tggtgttata aactgtgata   5040
gaaagtttta atgcaggtgg tagagagatt ttgaaatatt tagtagggaa aatagggga  a  5100 aacagttatc ttgattttat ttatatcatt tttaaaaggg catgttcttt aatggtcgat    5160
gagttggtct cttttcttgg tttggctaag gccagaaaca tatggctggg atagagatgt    5220
tcaaaaggtg tcaagctttg gccaacacac ttaaatagtg tggggagtct tcttgagccc   5280
gtggatcagt tatattttag agtattataa ggctagtaac attaaagaca actttgattg    5340
ttttcatgtt tggtcatgtg attgatttgt ttccgtactg ttctgttttt tgatgtgctt     5400
ggtttggtct tttgttgtat gtgtcataat ttctttccag ctgctccaaa aagagatctc    5460
```

-continued

```
tcaactcact cacctccacg atcaagcaag tgagaagggc aacgtggatg aatatccttt   5520
tatgagatgt cattttgaac tcactctttt atgctatcgt gcttgtcgac aatggtgaat   5580
aaatacctct attttcaaca tatcttcttt ccatttcctc ccgttcttct ttgcatattt   5640
tttttttttt tgtttcatga atattgagta cttgattagt ggcttttccc acaaaagttc   5700
tctcttgaat ttatcaatgc aagctggagg ttctctttaa ttatagtttc atgccttcta   5760
ttttaaattt aacttttgtg acgccttttc aaatgacaag ttatctggct cctggttttt   5820
gttaactaca ttgcacatct gtgcactgaa atatggaatt tgctttacac ccatattcaa   5880
ggactacaag atccactgga gcagagaagt tgaatgttct tcaatttatg cacatttcat   5940
ttgtttaact ttaggctgat gtggatgatt gtatttatag aaaagatttt tagttccttg   6000
actataccat acactaagat attttgcgga gaggttacat cgtctgaaat cacctgaaga   6060
atgccagcgt aggcttcttg aaattcttga agtacgttct gatccaacta tggatccgag   6120
ttacgagtct gaagaagata aggatgaatc aaacaagaaa agacaaggtc tgttaactgt   6180
cttttgttat tatggaacta tttttcaagtt tttccttgag ttagtattct gtaaatttat   6240
gtgtatgtgc aggaagtctc aagagatcta gaaattatga cttcgatgaa aaagaggtgg   6300
agcttacctc accacgaaga ggaaccaatt caaatgttag tggaagtgat gtacagcaaa   6360
attcgactag tacttcagag caaagtagaa atattagctt acttgctcac gagaataaag   6420
aaggtgactg cttggccagt gacaggaccg gtgaaacgtc gtgggcagga agaggtcttg   6480
taccaaataa ttggaatgta cctagtcagg ctaaaactgc cactcctttg tcctctgatg   6540
ggaattacca agtggtctta cctgaagcct caattccgcc actttctatt gggttaggaa   6600
cttcttctaa tgatgcagaa gtggaaagga tatggcaata ccaggatccg actggaaaag   6660
ttcagggtcc attttctatg acgcagttac gcaattggaa caatagtgga cacttcactc   6720
ctgatcttag agtatggagg ataactgaat cacaaaatga cgctgtactg ttaaccaatg   6780
cattaaatgg atgttacacc aaagcatctt ccatttggca caacagtcat attctgagtc   6840
tagggcgagg aaatggactt tctttggggtg gttcagataa tcatcataat ggtcaaagta   6900
atggaggtac tgattctggt acaaatttaa ttcggtttgg cgtggatcct atcaggaata   6960
gcaattctga gcagaaagat catattgcag tttgtgatgc tgaaaatgag cccatgatga   7020
gcactggttc aagctcacct tctaaagatt tgtgtgcacc tgcagacact gtcaactcta   7080
ttcagtctcc agctaggaac cttgaggtag cacacgagtc attgaagaac aataattcgt   7140
ggtcctaccc atcccttatg aatttacttt catcagcgac gttatcttta caaccacctg   7200
taactgaagt ccatcaggct aaggaaaacc acagccctaa taacgaggat cagaattcac   7260
agaccattac tttgggagga attcatagtc aaaccggtcg caagaaacgg tctagtagtg   7320
aggattgttc tagtcaatct tcagggcaaa actggatcgc tccacctgca acggatactt   7380
cctctcgtga atggaactct aattgtagtg gtctttcttt gatggattca ttcaagccat   7440
cagagaaaat tggagaaatt ttacctgata ttcctcattc taccctgaaa ccggtgactg   7500
cagatgctga aattaaacaa tctgcatctt caagtgttct tgttcagaat tctggcctta   7560
gctggagtag cgcctcaagt ttaccgggtg gacgacagct tcctagtcat gtagcagcgg   7620
gtgcttgggg gggtgggtat ttggctgcac caggtagagc aattgaggac ttgaactcca   7680
gtttcataac tgcatctggt atgaaatcat ctgatataat cgacgatcac gagacaactg   7740
gggctacaat aaaattggatt gatgatgaac ccaatgactt caattccttg gtcgatgaat   7800
```

-continued

```
ctgtctcaga tttgttagca gaagttgaag caatggaatg cttgagtggt ttggcttcca    7860
cagcatcgat gatgaattgt aacgagggat taactcggga ttctagaagt gattgttttt    7920
tctcagtcga tggtttcaat ccagcagctg agatggggaa ggtggatgca ttaagctcca    7980
cagccaattt gcagtttcca tttaacatca aagtgaaaga tgagcaacct tga           8033
```

```
<210> SEQ ID NO 7
<211> LENGTH: 8033
<212> TYPE: DNA
<213> ORGANISM: artificial
<220> FEATURE:
<223> OTHER INFORMATION: mutant WAP7.1 genomic sequence

<400> SEQUENCE: 7
```

```
atggacaaac ccctcgatcc gcctttggat ttctacaaac cccgtcttca acccgatgac      60
cctactccgc cgcctccaga cgcctccgtt ttggggaatt ctcatcaccc tccccacctc     120
atggactccc atatcgacga ttccaagctg gttggagttc cagtcgctgg acccctcctt     180
cctgccgatt cttcacccgc cgctaagctg aatgctaaat tcaaggacaa ggttcttgtt     240
gtcgacaaaa ctctcgggat tcgccgacga ggtcgtcctc ctcgtggtca agtcaagccc     300
cccccgttac cgccgagaca aaagaaggat gaggaggatg tgtgttttat atgctttgat     360
ggtggcagcc ttgttctctg tgatcgccgg tgagtggact ttgtttgtgc aaatttgttg     420
tgtggcttgc cgcaagtttc ggggacgatg agagattttt tttccccctc tactttggat     480
ttatggaatc tttgctttgc gcgttcgcct tttatttagg gaattccgtc tcgatcacac     540
ttgagcttgt tgattagttg tagctatttta agcggagatt tcgctgttaa tataatacgt     600
tgctccaatg aatttatctt gatttagttg aggtgaagga cacggaaata gtaattcttt     660
aattttgtac atctaaggtg agagaaaatt ttccttattt gagcgtaata ttacaatttc     720
acctcaattg tttcccattt cgttgtctct tactctttgc atgttctggg ttgtggtata     780
tttgattcgt tcccccttaag aaatggtttt catttattgt tatttgacag agggtgtcca     840
aaggcttatc atccatcatg cattaagcga gatgagtcat tctttcgatc caaggctaaa     900
tggaattgtg gtacgtagct ttgtgttttt ggttgttctc cggctgttac ttactgcact     960
gcactcgact gtggatgtca gtataatatt tattttctac ccaatattca ctatcgttta    1020
gaattcaaga tgcaatcttt tttcatcgtt gtgcaggatg gcacatatgc acaaattgcc    1080
agaaggcttc atattatatg tgctatacat gcccgttttc tctgtgcaag ggatgcatta    1140
aaggtgctga ttaccagtgt gttaggggaa ccaaagggtt ctgtggaact tgtatgaaaa    1200
taataatgct gttcgagaaa agcgcacctg acggagaatc ggtatgaaaa aattcgatgt    1260
tgtcttcctg tctatgcatg tatgacattc tattatttat ttctcaagtc tacttatact    1320
tccaattcga tagtggataa tatgaagaaa ttcattcatc atgtggtata tgcatgcaca    1380
ctcaagaaaa tccttctttg ctttccgttt cactcaagtg attcttggtt tgagattcac    1440
attccatctt tttatttgcc tggcgataaa ttcatctagt cgttcggagt atcgtttttg    1500
tttttggacc tggctattaa atgcatatat tagccatttt ctgtacgtca gtttctaatt    1560
tatgccttct atgttgtttc taacatccaa taaattgttc ttaaaatatg caggtccaag    1620
tcgattttga tgataaaagt agctgggagt atcttttttaa agtgtattgg atttacttga    1680
aagaaaaact ctctttaact gtggatgaac tcgttcgtgc taagaattca tggaaaggaa    1740
gcattatcat ggaccataag gtggcttcca gtgagattct cgatggcagt attgataaaa    1800
gccaaggagc tcataattca tttagaaacc caaaatcaca aaggaaaagg cctaacaggc    1860
```

-continued

```
aacaaagctc tctgaataaa ttcggctcct tagtggacag gccaagtagt aatgagcaat   1920
tttctgttag cacaaaatgg gcaactacag agctcatgga ctttgttgcc catgtgagaa   1980
atggtgacac gacaaggctt tcaccattgg atgtacaagc tttactgctg gagtatgtga   2040
agaaaaataa tcttcgtgat cctcaacagc aatcccaaat taattgtgat ttgaggctta   2100
ccaatctatt tgggaaatca cggataggtc actttgagat gctaaatctt cttcaatctc   2160
atgtgcacat aaaaggaact acagctgata atgcaaccag ctcaggtgct ggtgtagtga   2220
tcaatccagt tgaaagcaaa gagaagtatg attgtgaagt agtggatgat tgtgaaagaa   2280
agcgtaaaac acgcaagaaa gctgatgaga gcaggcagca attgcatgca attgtggatg   2340
aatatgccgc aattgacatt caaaacatta acttgattta cttgcggcgt gatctgatag   2400
tgagcctcat tgatgatgaa aaatttaatg acatggttat aggctctatt gtgagaatac   2460
agattccaaa taatgatgaa aaacatgatt ttcataggct tgtccaagtt gtaggtatta   2520
atatctaata ttaatgcttg atatgacata caatgatata tacatatttt taccctcgat   2580
cttaacattt tgcatatgtg tttaggcata agcaagatct ctacaccata cacagtcggt   2640
gagaaaacaa ttgatgtgat gcttgatata ttgaacttgg acaagagaga gtcggtgtct   2700
gttcagggga tttctaacca agaatttact gaggttatta aacttacctt attaattgaa   2760
aatgatagtt tcgtcgatct ctggtttaca tggctagttt gatgtcagtg actgatttta   2820
taatggtggt tacatagttt ctattatttt tatgcaagtt aaattcaatt attatgctta   2880
agtccgcaat tgctttggtt ttgtagttga tttgtttgtc tgttcagaat gtctacagaa   2940
catgctacat cttacggtct cacgggtttg cttctagttt aggccatatt gaagtagata   3000
acggttccac acattctaag ttggacccct gcctcattct caggattttc tcaaattgtt   3060
ttctaaaata taatgatggg gaggaaaagc ccatatttat tatttccaca tgtttagttt   3120
ttttgattgg tttctcatct cttttgattt ccgaagagag attgaattat catttctgtt   3180
ggagaccgaa tgggatgttg attaagaaac tcaacaaaca aaatgaacta attttttgggt  3240 tagagaactt tttatgtaaa gctaattgct cggaaatgca actacatgtt tctggctcaa   3300
aacagggaaa aaagaaaaaa gacaccaact taagcaatgt ttgagatact tttttatacaa  3360 gtcatccctc aaatctttc tttgcagtat gattgtgatt ttgaagttcg tgtatcatct    3420
ttatattggc ttcttttgat caaaagagtg gtattgatgg ttggtggtcc cctctttcag   3480
ttgatatgta atgtgatgga catgctactt gtgtcattgt taattttct aagaaatgcg    3540 tgcatgcatt ttacccttcc agtattgatg tattagtata tactcaggaa gaatgcaggc   3600
gtctacgccg gagcataaag tgtgggcttg tcaaacgatt cagagttgta agattacata   3660
tccatagatt ttttatatt tcaacctatt tagctgttgt gcctttaact cctatacagc    3720
ttgtgttgtt tatagaaatt tttgtttttg actgcagagt gaaattctgg acaaaggaag   3780
ggaacttcaa gcattgaaga ttaaggatgt gagttcaacc ccacttttgt caatcatgag   3840
actcaattac attctgcttt ggttttttttt tcttttcttt ttttgggtgt gtttctcttt   3900
ttggggtttt agaaattaga gtttatccat cttgaaagca atcagataaa acaaatacca   3960
gagtctaaag actattctcg attctcgaac taatgataat tcagaataac tcacgtccca   4020
taccacacat ctttggtgta tcacatctat ctttgacatc agataggatg cagtagtatc   4080
ttacacgctg tgatgttgaa gtagtgggag tggcttagaa gttagaatca gatctttaat   4140
gaaattttgc attaaaaagg ccaaaccccc caaaaaaaag ggccaaacca aggccacaaa   4200
```

```
aggtcaacct ccgcccaaaa ccagatcttt agtgaaaata aacttgcata aattcccatt   4260
atatttggat aggttctatt taaaatggaa aattagttta atcaattttt atatatgata   4320
tttttcttac tcgaaatacc aagcaaacat ctgataattt gagagaggct tcccatccat   4380
ctttgttatt atcctttttt ttttctggga gggggttctc cctactgccc cgcccctatg   4440
ttgttctctc tctttccttt gattaactcc acatcgtttc ttatctaaaa aaatatagat   4500
aaagaaatag caagcgaacc tcattagaat actttcctga atttttcatc cttatttttc   4560
ttaaccaaaa atatgttcaa ctatttatga gacgatcaac taagtctaag ttgtatgaaa   4620
ttcctttttt tatttttttta tttaattttt ttagattaag tttccaacta ttactaaaag   4680 aggggctaa accatatgat atgttttttt ggataagaaa accatatgat atgttataga   4740
ttagtagatt acaattatag atgagatgcc taggacttta acatgtatta catagatgga   4800
aactggaata tatgttttga agaaattaat atgcctgata aatcttcttt tcatttaata   4860
gtatttatga tgccaatatg tgagtcctct ctctgtctct gtcttctctt ctttctttct   4920
tctagggtga tgattgctat gaactgaagt ttacataatc actaaatgat taattcttgg   4980
cctagacaat gttgcaaaga caatgatatg tcatacagaa tggtgttata aactgtgata   5040
gaaagtttta atgcaggtgg tagagagatt ttgaaatatt tagtagggaa aataggggga   5100
aacagttatc ttgattttat ttatatcatt tttaaagggg catgttcttt aatggtcgat   5160
gagttggtct cttttcttgg tttggctaag gccagaaaca tatggctggg atagagatgt   5220
tcaaaaggtg tcaagctttg gccaacacac ttaaatagtg tggggagtct tcttgagccc   5280
gtggatcagt tatattttag agtattataa ggctagtaac attaaagaca actttgattg   5340
ttttcatgtt tggtcatgtg attgatttgt ttccgtactg ttctgttttt tgatgtgctt   5400
ggtttggtct tttgttgtat gtgtcataat ttctttccag ctgctccaaa aagagatctc   5460
tcaactcact cacctccacg atcaagcaag tgagaagggc aacgtggatg aatatccttt   5520
tatgagatgt cattttgaac tcactctttt atgctatcgt gcttgtcgac aatggtgaat   5580
aaatacctct attttcaaca tatcttcttt ccatttcctc ccgttcttct ttgcatattt   5640 ttttttttt tgtttcatga atattgagta cttgattagt ggcttttccc acaaaagttc   5700
tctcttgaat ttatcaatgc aagctggagg ttctctttaa ttatagtttc atgccttcta   5760
ttttaaattt aacttttgtg acgccttttc aaatgacaag ttatctggct tcctggtttt   5820
gttaactaca ttgcacatct gtgcactgaa atatggaatt tgctttacac ccatattcaa   5880
ggactacaag atccactgga gcagagaagt tgaatgttct tcaatttatg cacatttcat   5940
ttgtttaact ttaggctgat gtggatgatt gtatttatag aaaagatttt tagttccttg   6000
actataccat acactaagat attttgcgga gaggttacat cgtctgaaat cacctgaaga   6060
atgccagcgt aggcttcttg aaattcttga agtacgttct gatccaacta tggatccgag   6120
ttacgagtct gaagaagata aggatgaatc aaacaagaaa agacaaggtc tgttaactgt   6180
cttttgttat tatggaacta ttttcaagtt tttccttgag ttagtattct gtaaatttat   6240
gtgtatgtgc aggaagtctc aagagatcta gaaattatga cttcgatgaa aaagaggtgg   6300
agcttacctc accacgaaga ggaaccaatt caaatgttag tggaagtgat gtacagcaaa   6360
attcgactag tacttcagag caaagtagaa atattagctt acttgctcac gagaataaag   6420
aaggtgactg cttggccagt gacaggaccg gtgaaacgtc gtgggcagga agaggtcttg   6480
taccaaataa ttggaatgta cctagtcagg ctaaaactgc cactcctttg tcctctgatg   6540
ggaattacca agtggtctta cctgaagcct caattccgcc actttctatt gggttaggaa   6600
```

-continued

```
cttcttctaa tgatgcagaa gtggaaagga tatggcaata ccaggatccg actggaaaag    6660
ttcagggtcc attttctatg acgcagttac gcaattggaa caatagtgga cacttcactc    6720
ctgatcttag agtatggagg ataactgaat cacaaaatga cgctgtactg ttaaccaatg    6780
cattaaatgg atgttacacc aaagcatctt ccatttggca caacagtcat attctgagtc    6840
tagggcgagg aaatggactt tctttgggtg gttcagataa tcatcataat ggtcaaagta    6900
atggaggtac tgattctggt acaaatttaa ttcggtttgg cgtggatcct atcaggaata    6960
gcaattctga gcagaaagat catattgcag tttgtgatgc tgaaaatgag cccatgatga    7020
gcactggttc aagctcacct tctaaagatt tgtgtgcacc tgcagacact gtcaactcta    7080
ttcagtctcc agctaggaac cttgaggtag cacacgagtc attgaagaac aataattcgt    7140
ggtcctaccc atcccttatg aatttacttt catcagcgac gttatcttta caaccacctg    7200
taactgaagt ccatcaggct aaggaaaacc acagccctaa taacgaggat cagaattcac    7260
agaccattac tttgggagga attcatagtc aaaccggtcg caagaaacgg tctagtagtg    7320
aggattgttc tagtcaatct tcagggcaaa actggatcgc tccacctgca acggatactt    7380
cctctcgtga atgaaactct aattgtagtg gtctttcttt gatggattca ttcaagccat    7440
cagagaaaat tggagaaatt ttacctgata ttcctcattc taccctgaaa ccggtgactg    7500
cagatgctga aattaaacaa tctgcatctt caagtgttct tgttcagaat tctggcctta    7560
gctggagtag cgcctcaagt ttaccgggtg gacgacagct tcctagtcat gtagcagcgg    7620
gtgcttgggg gggtgggtat ttggctgcac caggtagagc aattgaggac ttgaactcca    7680
gtttcataac tgcatctggt atgaaatcat ctgatataat cgacgatcac gagacaactg    7740
gggctacaat aaaattggatt gatgatgaac ccaatgactt caattccttg gtcgatgaat    7800
ctgtctcaga tttgttagca gaagttgaag caatggaatg cttgagtggt ttggcttcca    7860
cagcatcgat gatgaattgt aacgagggat taactcggga ttctagaagt gattgttttt    7920
tctcagtcga tggtttcaat ccagcagctg agatggggaa ggtggatgca ttaagctcca    7980
cagccaattt gcagtttcca tttaacatca aagtgaaaga tgagcaacct tga           8033
```

<210> SEQ ID NO 8
<211> LENGTH: 1257
<212> TYPE: PRT
<213> ORGANISM: artificial
<220> FEATURE:
<223> OTHER INFORMATION: protein ClCG07G008850

<400> SEQUENCE: 8

```
Met Asp Lys Pro Leu Asp Pro Pro Leu Asp Phe Tyr Lys Pro Arg Leu
1               5                   10                  15

Gln Pro Asp Asp Pro Thr Pro Pro Pro Asp Ala Ser Val Leu Gly
            20                  25                  30

Asn Ser His His Pro Pro His Leu Met Asp Ser His Ile Asp Asp Ser
        35                  40                  45

Lys Leu Val Gly Val Pro Val Ala Gly Pro Leu Leu Pro Ala Asp Ser
    50                  55                  60

Ser Pro Ala Ala Lys Leu Asn Ala Lys Phe Lys Asp Lys Val Leu Val
65                  70                  75                  80

Val Asp Lys Thr Leu Gly Ile Arg Arg Arg Gly Arg Pro Pro Arg Gly
                85                  90                  95

Gln Val Lys Pro Pro Pro Leu Pro Pro Arg Gln Lys Lys Asp Glu Glu
            100                 105                 110
```

-continued

```
Asp Val Cys Phe Ile Cys Phe Asp Gly Gly Ser Leu Val Leu Cys Asp
        115             120             125

Arg Arg Gly Cys Pro Lys Ala Tyr His Pro Ser Cys Ile Lys Arg Asp
        130             135             140

Glu Ser Phe Phe Arg Ser Lys Ala Lys Trp Asn Cys Gly Trp His Ile
145             150             155             160

Cys Thr Asn Cys Gln Lys Ala Ser Tyr Tyr Met Cys Tyr Thr Cys Pro
            165             170             175

Phe Ser Leu Cys Lys Gly Cys Ile Lys Gly Ala Asp Tyr Gln Cys Val
            180             185             190

Arg Gly Thr Lys Gly Phe Cys Gly Thr Cys Met Lys Ile Ile Met Leu
            195             200             205

Phe Glu Lys Ser Ala Pro Asp Gly Glu Ser Val Gln Val Asp Phe Asp
        210             215             220

Asp Lys Ser Ser Trp Glu Tyr Leu Phe Lys Val Tyr Trp Ile Tyr Leu
225             230             235             240

Lys Glu Lys Leu Ser Leu Thr Val Asp Glu Leu Val Arg Ala Lys Asn
            245             250             255

Ser Trp Lys Gly Ser Ile Ile Met Asp His Lys Val Ala Ser Ser Glu
            260             265             270

Ile Leu Asp Gly Ser Ile Asp Lys Ser Gln Gly Ala His Asn Ser Phe
            275             280             285

Arg Asn Pro Lys Ser Gln Arg Lys Pro Asn Arg Gln Gln Ser Ser
        290             295             300

Leu Asn Lys Phe Gly Ser Leu Val Asp Arg Pro Ser Ser Asn Glu Gln
305             310             315             320

Phe Ser Val Ser Thr Lys Trp Ala Thr Thr Glu Leu Met Asp Phe Val
            325             330             335

Ala His Val Arg Asn Gly Asp Thr Thr Arg Leu Ser Pro Leu Asp Val
            340             345             350

Gln Ala Leu Leu Leu Glu Tyr Val Lys Lys Asn Asn Leu Arg Asp Pro
            355             360             365

Gln Gln Gln Ser Gln Ile Asn Cys Asp Leu Arg Leu Thr Asn Leu Phe
        370             375             380

Gly Lys Ser Arg Ile Gly His Phe Glu Met Leu Asn Leu Leu Gln Ser
385             390             395             400

His Val His Ile Lys Gly Thr Thr Ala Asp Asn Ala Thr Ser Ser Gly
            405             410             415

Ala Gly Val Val Ile Asn Pro Val Glu Ser Lys Glu Lys Tyr Asp Cys
            420             425             430

Glu Val Val Asp Asp Cys Glu Arg Lys Arg Lys Thr Arg Lys Lys Ala
            435             440             445

Asp Glu Ser Arg Gln Gln Leu His Ala Ile Val Asp Glu Tyr Ala Ala
        450             455             460

Ile Asp Ile Gln Asn Ile Asn Leu Ile Tyr Leu Arg Arg Asp Leu Ile
465             470             475             480

Val Ser Leu Ile Asp Asp Glu Lys Phe Asn Asp Met Val Ile Gly Ser
            485             490             495

Ile Val Arg Ile Gln Ile Pro Asn Asn Asp Glu Lys His Asp Phe His
            500             505             510

Arg Leu Val Gln Val Val Gly Ile Ser Lys Ile Ser Thr Pro Tyr Thr
            515             520             525
```

```
Val Gly Glu Lys Thr Ile Asp Val Met Leu Asp Ile Leu Asn Leu Asp
    530             535             540

Lys Arg Glu Ser Val Ser Val Gln Gly Ile Ser Asn Gln Glu Phe Thr
545             550             555             560

Glu Glu Glu Cys Arg Arg Leu Arg Arg Ser Ile Lys Cys Gly Leu Val
                565             570             575

Lys Arg Phe Arg Val Ser Glu Ile Leu Asp Lys Gly Arg Glu Leu Gln
            580             585             590

Ala Leu Lys Ile Lys Asp Leu Leu Gln Lys Glu Ile Ser Gln Leu Thr
            595             600             605

His Leu His Asp Gln Ala Ser Glu Lys Gly Asn Arg Leu His Arg Leu
    610             615             620

Lys Ser Pro Glu Glu Cys Gln Arg Arg Leu Leu Glu Ile Leu Glu Val
625             630             635             640

Arg Ser Asp Pro Thr Met Asp Pro Ser Tyr Glu Ser Glu Glu Asp Lys
                645             650             655

Asp Glu Ser Asn Lys Lys Arg Gln Gly Ser Leu Lys Arg Ser Arg Asn
            660             665             670

Tyr Asp Phe Asp Glu Lys Glu Val Glu Leu Thr Ser Pro Arg Arg Gly
            675             680             685

Thr Asn Ser Asn Val Ser Gly Ser Asp Val Gln Gln Asn Ser Thr Ser
    690             695             700

Thr Ser Glu Gln Ser Arg Asn Ile Ser Leu Leu Ala His Glu Asn Lys
705             710             715             720

Glu Gly Asp Cys Leu Ala Ser Asp Arg Thr Gly Glu Thr Ser Trp Ala
                725             730             735

Gly Arg Gly Leu Val Pro Asn Asn Trp Asn Val Pro Ser Gln Ala Lys
            740             745             750

Thr Ala Thr Pro Leu Ser Ser Asp Gly Asn Tyr Gln Val Val Leu Pro
            755             760             765

Glu Ala Ser Ile Pro Pro Leu Ser Ile Gly Leu Gly Thr Ser Ser Asn
    770             775             780

Asp Ala Glu Val Glu Arg Ile Trp Gln Tyr Gln Asp Pro Thr Gly Lys
785             790             795             800

Val Gln Gly Pro Phe Ser Met Thr Gln Leu Arg Asn Trp Asn Asn Ser
                805             810             815

Gly His Phe Thr Pro Asp Leu Arg Val Trp Arg Ile Thr Glu Ser Gln
            820             825             830

Asn Asp Ala Val Leu Leu Thr Asn Ala Leu Asn Gly Cys Tyr Thr Lys
            835             840             845

Ala Ser Ser Ile Trp His Asn Ser His Ile Leu Ser Leu Gly Arg Gly
    850             855             860

Asn Gly Leu Ser Leu Gly Gly Ser Asp Asn His His Asn Gly Gln Ser
865             870             875             880

Asn Gly Gly Thr Asp Ser Gly Thr Asn Leu Ile Arg Phe Gly Val Asp
                885             890             895

Pro Ile Arg Asn Ser Asn Ser Glu Gln Lys Asp His Ile Ala Val Cys
            900             905             910

Asp Ala Glu Asn Glu Pro Met Met Ser Thr Gly Ser Ser Ser Pro Ser
            915             920             925

Lys Asp Leu Cys Ala Pro Ala Asp Thr Val Asn Ser Ile Gln Ser Pro
    930             935             940

Ala Arg Asn Leu Glu Val Ala His Glu Ser Leu Lys Asn Asn Asn Ser
```

```
945                950                955                960

Trp Ser Tyr Pro Ser Leu Met Asn Leu Leu Ser Ser Ala Thr Leu Ser
            965                970                975

Leu Gln Pro Pro Val Thr Glu Val His Gln Ala Lys Glu Asn His Ser
            980                985                990

Pro Asn Asn Glu Asp Gln Asn Ser  Gln Thr Ile Thr Leu  Gly Gly Ile
        995                1000                1005

His Ser  Gln Thr Gly Arg Lys  Lys Arg Ser Ser Ser  Glu Asp Cys
    1010                1015                1020

Ser Ser  Gln Ser Ser Gly Gln  Asn Trp Ile Ala Pro  Pro Ala Thr
    1025                1030                1035

Asp Thr  Ser Ser Arg Glu Trp  Asn Ser Asn Cys Ser  Gly Leu Ser
    1040                1045                1050

Leu Met  Asp Ser Phe Lys Pro  Ser Glu Lys Ile Gly  Glu Ile Leu
    1055                1060                1065

Pro Asp  Ile Pro His Ser Thr  Leu Lys Pro Val Thr  Ala Asp Ala
    1070                1075                1080

Glu Ile  Lys Gln Ser Ala Ser  Ser Ser Val Leu Val  Gln Asn Ser
    1085                1090                1095

Gly Leu  Ser Trp Ser Ser Ala  Ser Ser Leu Pro Gly  Gly Arg Gln
    1100                1105                1110

Leu Pro  Ser His Val Ala Ala  Gly Ala Trp Gly Gly  Gly Tyr Leu
    1115                1120                1125

Ala Ala  Pro Gly Arg Ala Ile  Glu Asp Leu Asn Ser  Ser Phe Ile
    1130                1135                1140

Thr Ala  Ser Gly Met Lys Ser  Ser Asp Ile Ile Asp  Asp His Glu
    1145                1150                1155

Thr Thr  Gly Ala Thr Ile Asn  Trp Ile Asp Asp Glu  Pro Asn Asp
    1160                1165                1170

Phe Asn  Ser Leu Val Asp Glu  Ser Val Ser Asp Leu  Leu Ala Glu
    1175                1180                1185

Val Glu  Ala Met Glu Cys Leu  Ser Gly Leu Ala Ser  Thr Ala Ser
    1190                1195                1200

Met Met  Asn Cys Asn Glu Gly  Leu Thr Arg Asp Ser  Arg Ser Asp
    1205                1210                1215

Cys Phe  Phe Ser Val Asp Gly  Phe Asn Pro Ala Ala  Glu Met Gly
    1220                1225                1230

Lys Val  Asp Ala Leu Ser Ser  Thr Ala Asn Leu Gln  Phe Pro Phe
    1235                1240                1245

Asn Ile  Lys Val Lys Asp Glu  Gln Pro
    1250                1255
```

```
<210> SEQ ID NO 9
<211> LENGTH: 1294
<212> TYPE: PRT
<213> ORGANISM: artificial
<220> FEATURE:
<223> OTHER INFORMATION: protein Cla97C07G135900

<400> SEQUENCE: 9

Met Asp Lys Pro Leu Asp Pro Pro Leu Asp Phe Tyr Lys Pro Arg Leu
1                5                10                15

Gln Pro Asp Asp Pro Thr Pro Pro Pro Asp Ala Ser Val Leu Gly
            20                25                30

Asn Ser His His Pro Pro His Leu Met Asp Ser His Ile Asp Asp Ser
```

```
            35                  40                  45
Lys Leu Val Gly Val Pro Val Ala Gly Pro Leu Leu Pro Ala Asp Ser
    50                  55                  60

Ser Pro Ala Ala Lys Leu Asn Ala Lys Phe Lys Asp Lys Val Leu Val
65                  70                  75                  80

Val Asp Lys Thr Leu Gly Ile Arg Arg Arg Gly Arg Pro Pro Arg Gly
                85                  90                  95

Gln Val Lys Pro Pro Pro Leu Pro Pro Arg Gln Lys Lys Asp Glu Glu
            100                 105                 110

Asp Val Cys Phe Ile Cys Phe Asp Gly Gly Ser Leu Val Leu Cys Asp
            115                 120                 125

Arg Arg Gly Cys Pro Lys Ala Tyr His Pro Ser Cys Ile Lys Arg Asp
    130                 135                 140

Glu Ser Phe Phe Arg Ser Lys Ala Lys Trp Asn Cys Gly Trp His Ile
145                 150                 155                 160

Cys Thr Asn Cys Gln Lys Ala Ser Tyr Tyr Met Cys Tyr Thr Cys Pro
                165                 170                 175

Phe Ser Leu Cys Lys Gly Cys Ile Lys Gly Ala Asp Tyr Gln Cys Val
            180                 185                 190

Arg Gly Thr Lys Gly Phe Cys Gly Thr Cys Met Lys Ile Ile Met Leu
            195                 200                 205

Phe Glu Lys Ser Ala Pro Asp Gly Glu Ser Val Gln Val Asp Phe Asp
    210                 215                 220

Asp Lys Ser Ser Trp Glu Tyr Leu Phe Lys Val Tyr Trp Ile Tyr Leu
225                 230                 235                 240

Lys Glu Lys Leu Ser Leu Thr Val Asp Glu Leu Val Arg Ala Lys Asn
                245                 250                 255

Ser Trp Lys Gly Ser Ile Ile Met Asp His Lys Val Ala Ser Ser Glu
            260                 265                 270

Ile Leu Asp Gly Ser Ile Asp Lys Ser Gln Gly Ala His Asn Ser Phe
            275                 280                 285

Arg Asn Pro Lys Ser Gln Arg Lys Arg Pro Asn Arg Gln Gln Ser Ser
    290                 295                 300

Leu Asn Lys Phe Gly Ser Leu Val Asp Arg Pro Ser Ser Asn Glu Gln
305                 310                 315                 320

Phe Ser Val Ser Thr Lys Trp Ala Thr Thr Glu Leu Met Asp Phe Val
                325                 330                 335

Ala His Val Arg Asn Gly Asp Thr Thr Arg Leu Ser Pro Leu Asp Val
            340                 345                 350

Gln Ala Leu Leu Leu Glu Tyr Val Lys Lys Asn Asn Leu Arg Asp Pro
            355                 360                 365

Gln Gln Gln Ser Gln Ile Asn Cys Asp Leu Arg Leu Thr Asn Leu Phe
    370                 375                 380

Gly Lys Ser Arg Ile Gly His Phe Glu Met Leu Asn Leu Leu Gln Ser
385                 390                 395                 400

His Val His Ile Lys Gly Thr Thr Ala Asp Asn Ala Thr Ser Ser Gly
                405                 410                 415

Ala Gly Val Val Ile Asn Pro Val Glu Ser Lys Glu Lys Tyr Asp Cys
            420                 425                 430

Glu Val Val Asp Asp Cys Glu Arg Lys Arg Lys Thr Arg Lys Lys Ala
            435                 440                 445

Asp Glu Ser Arg Gln Gln Leu His Ala Ile Val Asp Glu Tyr Ala Ala
    450                 455                 460
```

-continued

```
Ile Asp Ile Gln Asn Ile Asn Leu Ile Tyr Leu Arg Arg Asp Leu Ile
465                 470             475             480

Val Ser Leu Ile Asp Asp Glu Lys Phe Asn Asp Met Val Ile Gly Ser
                485             490             495

Ile Val Arg Ile Gln Ile Pro Asn Asn Asp Glu Lys His Asp Phe His
            500             505             510

Arg Leu Val Gln Val Val Gly Ile Ser Lys Ile Ser Thr Pro Tyr Thr
            515             520             525

Val Gly Glu Lys Thr Ile Asp Val Met Leu Asp Ile Leu Asn Leu Asp
            530             535             540

Lys Arg Glu Ser Val Ser Val Gln Gly Ile Ser Asn Gln Glu Phe Thr
545             550             555             560

Glu Glu Glu Cys Arg Arg Leu Arg Arg Ser Ile Lys Cys Gly Leu Val
                565             570             575

Lys Arg Phe Arg Val Ser Glu Ile Leu Asp Lys Gly Arg Glu Leu Gln
                580             585             590

Ala Leu Lys Ile Lys Asp Leu Leu Gln Lys Glu Ile Ser Gln Leu Thr
                595             600             605

His Leu His Asp Gln Ala Ser Glu Lys Gly Asn Val Asp Glu Tyr Pro
            610             615             620

Phe Met Arg Cys His Phe Glu Leu Thr Leu Leu Cys Tyr Arg Ala Cys
625             630             635             640

Arg Gln Trp Thr Thr Arg Ser Thr Gly Ala Glu Lys Tyr Phe Ala Glu
                645             650             655

Arg Leu His Arg Leu Lys Ser Pro Glu Glu Cys Gln Arg Arg Leu Leu
                660             665             670

Glu Ile Leu Glu Val Arg Ser Asp Pro Thr Met Asp Pro Ser Tyr Glu
            675             680             685

Ser Glu Glu Asp Lys Asp Glu Ser Asn Lys Lys Arg Gln Gly Ser Leu
            690             695             700

Lys Arg Ser Arg Asn Tyr Asp Phe Asp Glu Lys Glu Val Glu Leu Thr
705             710             715             720

Ser Pro Arg Arg Gly Thr Asn Ser Asn Val Ser Gly Ser Asp Val Gln
                725             730             735

Gln Asn Ser Thr Ser Thr Ser Glu Gln Ser Arg Asn Ile Ser Leu Leu
                740             745             750

Ala His Glu Asn Lys Glu Gly Asp Cys Leu Ala Ser Asp Arg Thr Gly
                755             760             765

Glu Thr Ser Trp Ala Gly Arg Gly Leu Val Pro Asn Asn Trp Asn Val
            770             775             780

Pro Ser Gln Ala Lys Thr Ala Thr Pro Leu Ser Ser Asp Gly Asn Tyr
785             790             795             800

Gln Val Val Leu Pro Glu Ala Ser Ile Pro Pro Leu Ser Ile Gly Leu
                805             810             815

Gly Thr Ser Ser Asn Asp Ala Glu Val Glu Arg Ile Trp Gln Tyr Gln
                820             825             830

Asp Pro Thr Gly Lys Val Gln Gly Pro Phe Ser Met Thr Gln Leu Arg
            835             840             845

Asn Trp Asn Asn Ser Gly His Phe Thr Pro Asp Leu Arg Val Trp Arg
            850             855             860

Ile Thr Glu Ser Gln Asn Asp Ala Val Leu Leu Thr Asn Ala Leu Asn
865             870             875             880
```

-continued

```
Gly Cys Tyr Thr Lys Ala Ser Ser Ile Trp His Asn Ser His Ile Leu
            885                 890                 895

Ser Leu Gly Arg Gly Asn Gly Leu Ser Leu Gly Gly Ser Asp Asn His
            900                 905                 910

His Asn Gly Gln Ser Asn Gly Gly Thr Asp Ser Gly Thr Asn Leu Ile
            915                 920                 925

Arg Phe Gly Val Asp Pro Ile Arg Asn Ser Asn Ser Glu Gln Lys Asp
    930                 935                 940

His Ile Ala Val Cys Asp Ala Glu Asn Glu Pro Met Met Ser Thr Gly
945                 950                 955                 960

Ser Ser Ser Pro Ser Lys Asp Leu Cys Ala Pro Ala Asp Thr Val Asn
            965                 970                 975

Ser Ile Gln Ser Pro Ala Arg Asn Leu Glu Val Ala His Glu Ser Leu
            980                 985                 990

Lys Asn Asn Asn Ser Trp Ser Tyr Pro Ser Leu Met Asn Leu Leu Ser
            995                 1000                1005

Ser Ala Thr Leu Ser Leu Gln Pro Pro Val Thr Glu Val His Gln
    1010                1015                1020

Ala Lys Glu Asn His Ser Pro Asn Asn Glu Asp Gln Asn Ser Gln
    1025                1030                1035

Thr Ile Thr Leu Gly Gly Ile His Ser Gln Thr Gly Arg Lys Lys
    1040                1045                1050

Arg Ser Ser Ser Glu Asp Cys Ser Ser Gln Ser Ser Gly Gln Asn
    1055                1060                1065

Trp Ile Ala Pro Pro Ala Thr Asp Thr Ser Ser Arg Glu Trp Asn
    1070                1075                1080

Ser Asn Cys Ser Gly Leu Ser Leu Met Asp Ser Phe Lys Pro Ser
    1085                1090                1095

Glu Lys Ile Gly Glu Ile Leu Pro Asp Ile Pro His Ser Thr Leu
    1100                1105                1110

Lys Pro Val Thr Ala Asp Ala Glu Ile Lys Gln Ser Ala Ser Ser
    1115                1120                1125

Ser Val Leu Val Gln Asn Ser Gly Leu Ser Trp Ser Ser Ala Ser
    1130                1135                1140

Ser Leu Pro Gly Gly Arg Gln Leu Pro Ser His Val Ala Ala Gly
    1145                1150                1155

Ala Trp Gly Gly Gly Tyr Leu Ala Ala Pro Gly Arg Ala Ile Glu
    1160                1165                1170

Asp Leu Asn Ser Ser Phe Ile Thr Ala Ser Gly Met Lys Ser Ser
    1175                1180                1185

Asp Ile Ile Asp Asp His Glu Thr Thr Gly Ala Thr Ile Asn Trp
    1190                1195                1200

Ile Asp Asp Glu Pro Asn Asp Phe Asn Ser Leu Val Asp Glu Ser
    1205                1210                1215

Val Ser Asp Leu Leu Ala Glu Val Glu Ala Met Glu Cys Leu Ser
    1220                1225                1230

Gly Leu Ala Ser Thr Ala Ser Met Met Asn Cys Asn Glu Gly Leu
    1235                1240                1245

Thr Arg Asp Ser Arg Ser Asp Cys Phe Phe Ser Val Asp Gly Phe
    1250                1255                1260

Asn Pro Ala Ala Glu Met Gly Lys Val Asp Ala Leu Ser Ser Thr
    1265                1270                1275

Ala Asn Leu Gln Phe Pro Phe Asn Ile Lys Val Lys Asp Glu Gln
```

-continued

```
                1280                1285                1290

Pro

<210> SEQ ID NO 10
<211> LENGTH: 372
<212> TYPE: PRT
<213> ORGANISM: Citrullus lanatus

<400> SEQUENCE: 10

Met Asp Lys Pro Leu Asp Pro Pro Leu Asp Phe Tyr Lys Pro Arg Leu
1               5                   10                  15

Gln Pro Asp Asp Pro Thr Pro Pro Pro Asp Ala Ser Val Leu Gly
            20                  25                  30

Asn Ser His His Pro Pro His Leu Met Asp Ser His Ile Asp Asp Ser
            35                  40                  45

Lys Leu Val Gly Val Pro Val Ala Gly Pro Leu Leu Pro Ala Asp Ser
        50                  55                  60

Ser Pro Ala Ala Lys Leu Asn Ala Lys Phe Lys Asp Lys Val Leu Val
65                  70                  75                  80

Val Asp Lys Thr Leu Gly Ile Arg Arg Arg Gly Arg Pro Pro Arg Gly
                85                  90                  95

Gln Val Lys Pro Pro Pro Leu Pro Pro Arg Gln Lys Lys Asp Glu Glu
            100                 105                 110

Asp Val Cys Phe Ile Cys Phe Asp Gly Gly Ser Leu Val Leu Cys Asp
            115                 120                 125

Arg Arg Gly Cys Pro Lys Ala Tyr His Pro Ser Cys Ile Lys Arg Asp
        130                 135                 140

Glu Ser Phe Phe Arg Ser Lys Ala Lys Trp Asn Cys Gly Trp His Ile
145                 150                 155                 160

Cys Thr Asn Cys Gln Lys Ala Ser Tyr Tyr Met Cys Tyr Thr Cys Pro
                165                 170                 175

Phe Ser Leu Cys Lys Gly Cys Ile Lys Gly Ala Asp Tyr Gln Cys Val
            180                 185                 190

Arg Gly Thr Lys Gly Phe Cys Gly Thr Cys Met Lys Ile Ile Met Leu
            195                 200                 205

Phe Glu Lys Ser Ala Pro Asp Gly Glu Ser Val Gln Val Asp Phe Asp
        210                 215                 220

Asp Lys Ser Ser Trp Glu Tyr Leu Phe Lys Val Tyr Trp Ile Tyr Leu
225                 230                 235                 240

Lys Glu Lys Leu Ser Leu Thr Val Asp Glu Leu Val Arg Ala Lys Asn
                245                 250                 255

Ser Trp Lys Gly Ser Ile Ile Met Asp His Lys Val Ala Ser Ser Glu
            260                 265                 270

Ile Leu Asp Gly Ser Ile Asp Lys Ser Gln Gly Ala His Asn Ser Phe
        275                 280                 285

Arg Asn Pro Lys Ser Gln Arg Lys Arg Pro Asn Arg Gln Gln Ser Ser
        290                 295                 300

Leu Asn Lys Phe Gly Ser Leu Val Asp Arg Pro Ser Ser Asn Glu Gln
305                 310                 315                 320

Phe Ser Val Ser Thr Lys Trp Ala Thr Thr Glu Leu Met Asp Phe Val
                325                 330                 335

Ala His Val Arg Asn Gly Asp Thr Thr Arg Leu Ser Pro Leu Asp Val
            340                 345                 350

Gln Ala Leu Leu Leu Glu Tyr Val Lys Lys Asn Asn Leu Arg Asp Pro
```

-continued

```
                355                 360                 365

Gln Gln Gln Ser
    370

<210> SEQ ID NO 11
<211> LENGTH: 1266
<212> TYPE: PRT
<213> ORGANISM: Citrullus lanatus

<400> SEQUENCE: 11

Met Asp Lys Pro Leu Asp Pro Pro Leu Asp Phe Tyr Lys Pro Arg Leu
1               5                   10                  15

Gln Pro Asp Asp Pro Thr Pro Pro Pro Asp Ala Ser Val Leu Gly
            20                  25                  30

Asn Ser His His Pro Pro His Leu Met Asp Ser His Ile Asp Asp Ser
        35                  40                  45

Lys Leu Val Gly Val Pro Val Ala Gly Pro Leu Leu Pro Ala Asp Ser
    50                  55                  60

Ser Pro Ala Ala Lys Leu Asn Ala Lys Phe Lys Asp Lys Val Leu Val
65                  70                  75                  80

Val Asp Lys Thr Leu Gly Ile Arg Arg Arg Gly Arg Pro Pro Arg Gly
                85                  90                  95

Gln Val Lys Pro Pro Pro Leu Pro Pro Arg Gln Lys Lys Asp Glu Glu
            100                 105                 110

Asp Val Cys Phe Ile Cys Phe Asp Gly Gly Ser Leu Val Leu Cys Asp
        115                 120                 125

Arg Arg Gly Cys Pro Lys Ala Tyr His Pro Ser Cys Ile Lys Arg Asp
    130                 135                 140

Glu Ser Phe Phe Arg Ser Lys Ala Lys Trp Asn Cys Gly Trp His Ile
145                 150                 155                 160

Cys Thr Asn Cys Gln Lys Ala Ser Tyr Tyr Met Cys Tyr Thr Cys Pro
                165                 170                 175

Phe Ser Leu Cys Lys Gly Cys Ile Lys Gly Ala Asp Tyr Gln Cys Val
            180                 185                 190

Arg Gly Thr Lys Gly Phe Cys Gly Thr Cys Met Lys Ile Ile Met Leu
        195                 200                 205

Phe Glu Lys Ser Ala Pro Asp Gly Glu Ser Val Gln Val Asp Phe Asp
    210                 215                 220

Asp Lys Ser Ser Trp Glu Tyr Leu Phe Lys Val Tyr Trp Ile Tyr Leu
225                 230                 235                 240

Lys Glu Lys Leu Ser Leu Thr Val Asp Glu Leu Val Arg Ala Lys Asn
                245                 250                 255

Ser Trp Lys Gly Ser Ile Ile Met Asp His Lys Val Ala Ser Ser Glu
            260                 265                 270

Ile Leu Asp Gly Ser Ile Asp Lys Ser Gln Gly Ala His Asn Ser Phe
        275                 280                 285

Arg Asn Pro Lys Ser Gln Arg Lys Arg Pro Asn Arg Gln Gln Ser Ser
    290                 295                 300

Leu Asn Lys Phe Gly Ser Leu Val Asp Arg Pro Ser Ser Asn Glu Gln
305                 310                 315                 320

Phe Ser Val Ser Thr Lys Trp Ala Thr Thr Glu Leu Met Asp Phe Val
                325                 330                 335

Ala His Val Arg Asn Gly Asp Thr Thr Lys Leu Ser Pro Leu Asp Val
            340                 345                 350
```

```
Gln Ala Leu Leu Leu Glu Tyr Val Lys Lys Asn Asn Leu Arg Asp Pro
        355                 360                 365

Gln Gln Gln Ser Gln Ile Asn Cys Asp Leu Arg Leu Thr Asn Leu Phe
        370                 375                 380

Gly Lys Ser Arg Ile Gly His Phe Glu Met Leu Asn Leu Leu Gln Ser
385                 390                 395                 400

His Val His Ile Lys Gly Thr Thr Ala Asp Asn Ala Thr Ser Ser Gly
                405                 410                 415

Ala Gly Val Val Ile Asn Pro Val Glu Ser Lys Glu Lys Tyr Asp Cys
                420                 425                 430

Glu Val Val Asp Asp Cys Glu Arg Lys Arg Lys Thr Arg Lys Lys Ala
                435                 440                 445

Asp Glu Ser Arg Gln Gln Leu His Ala Ile Val Asp Glu Tyr Ala Ala
        450                 455                 460

Ile Asp Ile Gln Asn Ile Asn Leu Ile Tyr Leu Arg Arg Asp Leu Ile
465                 470                 475                 480

Val Ser Leu Ile Asp Asp Glu Lys Phe Asn Asp Met Val Ile Gly Ser
                485                 490                 495

Ile Val Arg Ile Gln Ile Pro Asn Asn Asp Glu Lys His Asp Phe His
                500                 505                 510

Arg Leu Val Gln Val Val Gly Ile Ser Lys Ile Ser Thr Pro Tyr Thr
                515                 520                 525

Val Gly Glu Lys Thr Ile Asp Val Met Leu Asp Ile Leu Asn Leu Asp
        530                 535                 540

Lys Arg Glu Ser Val Ser Val Gln Gly Ile Ser Asn Gln Glu Phe Thr
545                 550                 555                 560

Glu Glu Glu Cys Arg Arg Leu Arg Arg Ser Ile Lys Cys Gly Leu Val
                565                 570                 575

Lys Arg Phe Arg Val Ser Glu Ile Leu Asp Lys Gly Arg Glu Leu Gln
                580                 585                 590

Ala Leu Lys Ile Lys Asp Leu Leu Gln Lys Glu Ile Ser Gln Leu Thr
        595                 600                 605

His Leu His Asp Gln Ala Ser Glu Lys Gly Asn Val Asp Glu Leu Arg
        610                 615                 620

Tyr Phe Ala Glu Arg Leu His Arg Leu Lys Ser Pro Glu Glu Cys Gln
625                 630                 635                 640

Arg Arg Leu Leu Glu Ile Leu Glu Val Arg Ser Asp Pro Thr Met Asp
                645                 650                 655

Pro Ser Tyr Glu Ser Glu Glu Asp Lys Asp Glu Ser Asn Lys Lys Arg
                660                 665                 670

Gln Gly Ser Leu Lys Arg Ser Arg Asn Tyr Asp Phe Asp Glu Lys Glu
        675                 680                 685

Val Glu Leu Thr Ser Pro Arg Arg Gly Thr Asn Ser Asn Val Ser Gly
        690                 695                 700

Ser Asp Val Gln Gln Asn Ser Thr Ser Thr Ser Glu Gln Ser Arg Asn
705                 710                 715                 720

Ile Ser Leu Leu Ala His Glu Asn Lys Glu Gly Asp Cys Leu Ala Ser
                725                 730                 735

Asp Arg Thr Gly Glu Thr Ser Trp Ala Gly Arg Gly Leu Val Pro Asn
                740                 745                 750

Asn Trp Asn Val Pro Ser Gln Ala Lys Thr Ala Thr Pro Leu Ser Ser
        755                 760                 765

Asp Gly Asn Tyr Gln Val Val Leu Pro Glu Ala Ser Ile Pro Pro Leu
```

```
        770           775           780

Ser Ile Gly Leu Gly Thr Ser Ser Asn Asp Ala Glu Val Glu Arg Ile
785               790             795             800

Trp Gln Tyr Gln Asp Pro Thr Gly Lys Val Gln Gly Pro Phe Ser Met
                805             810             815

Thr Gln Leu Arg Asn Trp Asn Asn Ser Gly His Phe Thr Pro Asp Leu
            820             825             830

Arg Val Trp Arg Ile Thr Glu Ser Gln Asn Asp Ala Val Leu Leu Thr
        835             840             845

Asn Ala Leu Asn Gly Cys Tyr Thr Lys Ala Ser Ser Ile Trp His Asn
    850             855             860

Ser His Ile Leu Ser Leu Gly Arg Gly Asn Gly Leu Ser Leu Gly Gly
865             870             875             880

Ser Asp Asn His His Asn Gly Gln Ser Asn Gly Gly Thr Asp Ser Gly
            885             890             895

Thr Asn Leu Ile Arg Phe Gly Val Asp Pro Ile Arg Asn Ser Asn Ser
        900             905             910

Glu Gln Lys Asp His Ile Ala Val Cys Asp Ala Glu Asn Glu Pro Met
        915             920             925

Met Ser Thr Gly Ser Ser Ser Pro Ser Lys Asp Leu Cys Ala Pro Ala
    930             935             940

Asp Thr Val Asn Ser Ile Gln Ser Pro Ala Arg Asn Leu Glu Val Ala
945             950             955             960

His Glu Ser Leu Lys Asn Asn Asn Ser Trp Ser Tyr Pro Ser Leu Met
            965             970             975

Asn Leu Leu Ser Ser Ala Thr Leu Ser Leu Gln Pro Pro Val Thr Glu
            980             985             990

Val His Gln Ala Lys Glu Asn His  Ser Pro Asn Asn Glu  Asp Gln Asn
        995             1000                1005

Ser Gln  Thr Ile Thr Leu Gly  Gly Ile His Ser Gln  Thr Gly Arg
    1010            1015                1020

Lys Lys  Arg Ser Ser Ser Glu  Asp Cys Ser Ser Gln  Ser Ser Gly
    1025            1030                1035

Gln Asn  Trp Ile Ala Pro Pro  Ala Thr Asp Thr Ser  Ser Arg Glu
    1040            1045                1050

Trp Asn  Ser Asn Cys Ser Gly  Leu Ser Leu Met Asp  Ser Phe Lys
    1055            1060                1065

Pro Ser  Glu Lys Ile Gly Glu  Ile Leu Pro Asp Ile  Pro His Ser
    1070            1075                1080

Thr Leu  Lys Pro Val Thr Ala  Asp Ala Glu Ile Lys  Gln Ser Ala
    1085            1090                1095

Ser Ser  Ser Val Leu Val Gln  Asn Ser Gly Leu Ser  Trp Ser Ser
    1100            1105                1110

Ala Ser  Ser Leu Pro Gly Gly  Arg Gln Leu Pro Ser  His Val Ala
    1115            1120                1125

Ala Gly  Ala Trp Gly Gly Gly  Tyr Leu Ala Ala Pro  Gly Arg Ala
    1130            1135                1140

Ile Glu  Asp Leu Asn Ser Ser  Phe Ile Thr Ala Ser  Gly Met Lys
    1145            1150                1155

Ser Ser  Asp Ile Ile Asp Asp  His Glu Thr Thr Gly  Ala Thr Ile
    1160            1165                1170

Asn Trp  Ile Asp Asp Glu Pro  Asn Asp Phe Asn Ser  Leu Val Asp
    1175            1180                1185
```

-continued

```
Glu Ser  Val Ser Asp Leu Leu  Ala Glu Val Glu Ala  Met Glu Cys
    1190             1195             1200

Leu Ser  Gly Leu Ala Ser Thr  Ala Ser Met Met Asn  Cys Asn Glu
    1205             1210             1215

Gly Leu  Thr Arg Asp Ser Arg  Ser Asp Cys Phe Phe  Ser Val Asp
    1220             1225             1230

Gly Phe  Asn Pro Ala Ala Glu  Met Gly Lys Val Asp  Ala Leu Ser
    1235             1240             1245

Ser Thr  Ala Asn Leu Gln Phe  Pro Phe Asn Ile Lys  Val Lys Asp
    1250             1255             1260

Glu Gln  Pro
    1265

<210> SEQ ID NO 12
<211> LENGTH: 1266
<212> TYPE: PRT
<213> ORGANISM: Citrullus lanatus

<400> SEQUENCE: 12

Met Asp Lys Pro Leu Asp Pro Pro Leu Asp Phe Tyr Lys Pro Arg Leu
1               5                   10                  15

Gln Pro Asp Asp Pro Thr Pro Pro Pro Asp Ala Ser Val Leu Gly
            20              25              30

Asn Ser His His Pro Pro His Leu Met Asp Ser His Ile Asp Asp Ser
        35              40                  45

Lys Leu Val Gly Val Pro Val Ala Gly Pro Leu Leu Pro Ala Asp Ser
    50              55                  60

Ser Pro Ala Ala Lys Leu Asn Ala Lys Phe Lys Asp Lys Val Leu Val
65              70                  75                  80

Val Asp Lys Thr Leu Gly Ile Arg Arg Arg Gly Arg Pro Pro Arg Gly
                85              90                  95

Gln Val Lys Pro Pro Pro Leu Pro Pro Arg Gln Lys Lys Asp Glu Glu
            100             105                 110

Asp Val Cys Phe Ile Cys Phe Asp Gly Gly Ser Leu Val Leu Cys Asp
            115             120                 125

Arg Arg Gly Cys Pro Lys Ala Tyr His Pro Ser Cys Ile Lys Arg Asp
    130             135                 140

Glu Ser Phe Phe Arg Ser Lys Ala Lys Trp Asn Cys Gly Trp His Ile
145             150                 155                 160

Cys Thr Asn Cys Gln Lys Ala Ser Tyr Tyr Met Cys Tyr Thr Cys Pro
            165             170                 175

Phe Ser Leu Cys Lys Gly Cys Ile Lys Gly Ala Asp Tyr Gln Cys Val
            180             185                 190

Arg Gly Thr Lys Gly Phe Cys Gly Thr Cys Met Lys Ile Ile Met Leu
            195             200                 205

Phe Glu Lys Ser Ala Pro Asp Gly Glu Ser Val Gln Val Asp Phe Asp
    210             215                 220

Asp Lys Ser Ser Trp Glu Tyr Leu Phe Lys Val Tyr Trp Ile Tyr Leu
225             230                 235                 240

Lys Glu Lys Leu Ser Leu Thr Val Asp Glu Leu Val Arg Ala Lys Asn
            245                 250                 255

Ser Trp Lys Gly Ser Ile Ile Met Asp His Lys Val Ala Ser Ser Glu
            260                 265                 270

Ile Leu Asp Gly Ser Ile Asp Lys Ser Gln Gly Ala His Asn Ser Phe
```

-continued

```
             275                 280                 285

Arg Asn Pro Lys Ser Gln Arg Lys Arg Pro Asn Arg Gln Gln Ser Ser
    290                 295                 300

Leu Asn Lys Phe Gly Ser Leu Val Asp Arg Pro Ser Ser Asn Glu Gln
305                 310                 315                 320

Phe Ser Val Asn Thr Lys Trp Ala Thr Thr Glu Leu Met Asp Phe Val
                325                 330                 335

Ala His Val Arg Asn Gly Asp Thr Thr Arg Leu Ser Pro Leu Asp Val
                340                 345                 350

Gln Ala Leu Leu Leu Glu Tyr Val Lys Lys Asn Asn Leu Arg Asp Pro
                355                 360                 365

Gln Gln Gln Ser Gln Ile Asn Cys Asp Leu Arg Leu Thr Asn Leu Phe
    370                 375                 380

Gly Lys Ser Arg Ile Gly His Phe Glu Met Leu Asn Leu Leu Gln Ser
385                 390                 395                 400

His Val His Ile Lys Gly Thr Thr Ala Asp Asn Ala Thr Ser Ser Gly
                405                 410                 415

Ala Gly Val Val Ile Asn Pro Val Glu Ser Lys Glu Lys Tyr Asp Cys
                420                 425                 430

Glu Val Val Asp Asp Cys Glu Arg Lys Arg Lys Thr Arg Lys Lys Ala
                435                 440                 445

Asp Glu Ser Arg Gln Gln Leu His Ala Ile Val Asp Glu Tyr Ala Ala
    450                 455                 460

Ile Asp Ile Gln Asn Ile Asn Leu Ile Tyr Leu Arg Arg Asp Leu Ile
465                 470                 475                 480

Val Ser Leu Ile Asp Asp Glu Lys Phe Asn Asp Met Val Ile Gly Ser
                485                 490                 495

Ile Val Arg Ile Gln Ile Pro Asn Asn Asp Glu Lys His Asp Phe His
                500                 505                 510

Arg Leu Val Gln Val Val Gly Ile Ser Lys Ile Ser Thr Pro Tyr Thr
                515                 520                 525

Val Gly Glu Lys Thr Ile Asp Val Met Leu Asp Ile Leu Asn Leu Asp
    530                 535                 540

Lys Arg Glu Ser Val Ser Val Gln Gly Ile Ser Asn Gln Glu Phe Thr
545                 550                 555                 560

Glu Glu Glu Cys Arg Arg Leu Arg Arg Ser Ile Lys Cys Gly Leu Val
                565                 570                 575

Lys Arg Phe Arg Val Ser Glu Ile Leu Asp Lys Gly Arg Glu Leu Gln
                580                 585                 590

Ala Leu Lys Ile Lys Asp Leu Leu Gln Lys Glu Ile Ser Gln Leu Thr
                595                 600                 605

His Leu His Asp Gln Ala Ser Glu Lys Gly Asn Val Asp Glu Leu Arg
    610                 615                 620

Tyr Phe Ala Glu Arg Leu His Arg Leu Lys Ser Pro Glu Glu Cys Gln
625                 630                 635                 640

Arg Arg Leu Leu Glu Ile Leu Glu Val Arg Ser Asp Pro Thr Met Asp
                645                 650                 655

Pro Ser Tyr Glu Ser Glu Glu Asp Lys Asp Glu Ser Asn Lys Lys Arg
                660                 665                 670

Gln Gly Ser Leu Lys Arg Ser Arg Asn Tyr Asp Phe Asp Glu Lys Glu
                675                 680                 685

Val Glu Leu Thr Ser Pro Arg Arg Gly Thr Asn Ser Asn Val Ser Gly
    690                 695                 700
```

```
Ser Asp Val Gln Gln Asn Ser Thr Ser Thr Ser Glu Gln Ser Arg Asn
705                 710                 715                 720

Ile Ser Leu Leu Ala His Glu Asn Lys Glu Gly Asp Cys Leu Ala Ser
                725                 730                 735

Asp Arg Thr Gly Glu Thr Ser Trp Ala Gly Arg Gly Leu Val Pro Asn
            740                 745                 750

Asn Trp Asn Val Pro Ser Gln Ala Lys Thr Ala Thr Pro Leu Ser Ser
            755                 760                 765

Asp Gly Asn Tyr Gln Val Val Leu Pro Glu Ala Ser Ile Pro Pro Leu
        770                 775                 780

Ser Ile Gly Leu Gly Thr Ser Ser Asn Asp Ala Glu Val Glu Arg Ile
785                 790                 795                 800

Trp Gln Tyr Gln Asp Pro Thr Gly Lys Val Gln Gly Pro Phe Ser Met
                805                 810                 815

Thr Gln Leu Arg Asn Trp Asn Asn Ser Gly His Phe Thr Pro Asp Leu
                820                 825                 830

Arg Val Trp Arg Ile Thr Glu Ser Gln Asn Asp Ala Val Leu Leu Thr
            835                 840                 845

Asn Ala Leu Asn Gly Cys Tyr Thr Lys Ala Ser Ser Ile Trp His Asn
        850                 855                 860

Ser His Ile Leu Ser Leu Gly Arg Gly Asn Gly Leu Ser Leu Gly Gly
865                 870                 875                 880

Ser Asp Asn His His Asn Gly Gln Ser Asn Gly Gly Thr Asp Ser Gly
                885                 890                 895

Thr Asn Leu Ile Arg Phe Gly Val Asp Pro Ile Arg Asn Ser Asn Ser
            900                 905                 910

Glu Gln Lys Asp His Ile Ala Val Cys Asp Ala Glu Asn Glu Pro Met
            915                 920                 925

Met Ser Thr Gly Ser Ser Ser Pro Ser Lys Asp Leu Cys Ala Pro Ala
        930                 935                 940

Asp Thr Val Asn Ser Ile Gln Ser Pro Ala Arg Asn Leu Glu Val Ala
945                 950                 955                 960

His Glu Ser Leu Lys Asn Asn Asn Ser Trp Ser Tyr Pro Ser Leu Met
                965                 970                 975

Asn Leu Leu Ser Ser Ala Thr Leu Ser Leu Gln Pro Pro Val Thr Glu
                980                 985                 990

Val His Gln Ala Lys Glu Asn His  Ser Pro Asn Asn Glu  Asp Gln Asn
            995                 1000                1005

Ser Gln  Thr Ile Thr Leu Gly  Gly Ile His Ser Gln  Thr Gly Arg
    1010                1015                1020

Lys Lys  Arg Ser Ser Ser Glu  Asp Cys Ser Ser Gln  Ser Ser Gly
    1025                1030                1035

Gln Asn  Trp Ile Ala Pro Pro  Ala Thr Asp Thr Ser  Ser Arg Glu
    1040                1045                1050

Trp Asn  Ser Asn Cys Ser Gly  Leu Ser Leu Met Asp  Ser Phe Lys
    1055                1060                1065

Pro Ser  Glu Lys Ile Gly Glu  Ile Leu Pro Asp Ile  Pro His Ser
    1070                1075                1080

Thr Leu  Lys Pro Val Thr Ala  Asp Ala Glu Ile Lys  Gln Ser Ala
    1085                1090                1095

Ser Ser  Ser Val Leu Val Gln  Asn Ser Gly Leu Ser  Trp Ser Ser
    1100                1105                1110
```

-continued

```
Ala Ser  Ser Leu Pro Gly Gly  Arg Gln Leu Pro Ser  His Val Ala
    1115             1120             1125

Ala Gly  Ala Trp Gly Gly Gly  Tyr Leu Ala Ala Pro  Gly Arg Ala
    1130             1135             1140

Ile Glu  Asp Leu Asn Ser Ser  Phe Ile Thr Ala Ser  Gly Met Lys
    1145             1150             1155

Ser Ser  Asp Ile Ile Asp Asp  His Glu Thr Thr Gly  Ala Thr Ile
    1160             1165             1170

Asn Trp  Ile Asp Asp Glu Pro  Asn Asp Phe Asn Ser  Leu Val Asp
    1175             1180             1185

Glu Ser  Val Ser Asp Leu Leu  Ala Glu Val Glu Ala  Met Glu Cys
    1190             1195             1200

Leu Ser  Gly Leu Ala Ser Thr  Ala Ser Met Met Asn  Cys Asn Glu
    1205             1210             1215

Gly Leu  Thr Arg Asp Ser Arg  Ser Asp Cys Phe Phe  Ser Val Asp
    1220             1225             1230

Gly Phe  Asn Pro Ala Ala Glu  Met Gly Lys Val Asp  Ala Leu Ser
    1235             1240             1245

Ser Thr  Ala Asn Leu Gln Phe  Pro Phe Asn Ile Lys  Val Lys Asp
    1250             1255             1260

Glu Gln  Pro
    1265

<210> SEQ ID NO 13
<211> LENGTH: 1266
<212> TYPE: PRT
<213> ORGANISM: Citrullus lanatus

<400> SEQUENCE: 13

Met Asp Lys Pro Leu Asp Pro Pro Leu Asp Phe Tyr Lys Pro Arg Leu
1               5               10              15

Gln Pro Asp Asp Pro Thr Pro Pro Pro Asp Ala Ser Val Leu Gly
        20              25              30

Asn Ser His His Pro Pro His Leu Met Asp Ser His Ile Asp Asp Ser
        35              40              45

Lys Leu Val Gly Val Pro Val Ala Gly Pro Leu Leu Pro Ala Asp Ser
    50              55              60

Ser Pro Ala Ala Lys Leu Asn Ala Lys Phe Lys Asp Lys Val Leu Val
65              70              75              80

Val Asp Lys Thr Leu Gly Ile Arg Arg Arg Gly Arg Pro Pro Arg Gly
            85              90              95

Gln Val Lys Pro Pro Pro Leu Pro Pro Arg Gln Lys Lys Asp Glu Glu
            100             105             110

Asp Val Cys Phe Ile Cys Phe Asp Gly Gly Ser Leu Val Leu Cys Asp
            115             120             125

Arg Arg Gly Cys Pro Lys Ala Tyr His Pro Ser Cys Ile Lys Arg Asp
        130             135             140

Glu Ser Phe Phe Arg Ser Lys Ala Lys Trp Asn Cys Gly Trp His Ile
145             150             155             160

Cys Thr Asn Cys Gln Lys Ala Ser Tyr Tyr Met Cys Tyr Thr Cys Pro
            165             170             175

Phe Ser Leu Cys Lys Gly Cys Ile Lys Gly Ala Asp Tyr Gln Cys Val
            180             185             190

Arg Gly Thr Lys Gly Phe Cys Gly Thr Cys Met Lys Ile Ile Met Leu
        195             200             205
```

-continued

```
Phe Glu Lys Ser Ala Pro Asp Gly Glu Ser Val Gln Val Asp Phe Asp
    210             215             220

Asp Lys Ser Ser Trp Glu Tyr Leu Phe Lys Val Tyr Trp Ile Tyr Leu
225             230             235             240

Lys Glu Lys Leu Ser Leu Thr Val Asp Glu Leu Val Arg Ala Lys Asn
            245             250             255

Ser Trp Lys Gly Ser Ile Ile Met Asp His Lys Val Ala Ser Ser Glu
            260             265             270

Ile Leu Asp Gly Ser Ile Asp Lys Ser Gln Gly Ala His Asn Ser Phe
        275             280             285

Arg Asn Pro Lys Ser Gln Arg Lys Arg Pro Asn Arg Gln Gln Ser Ser
    290             295             300

Leu Asn Lys Phe Gly Ser Leu Val Asp Arg Pro Ser Ser Asn Glu Gln
305             310             315             320

Phe Ser Val Ser Thr Lys Trp Ala Thr Thr Glu Leu Met Asp Phe Val
            325             330             335

Ala His Val Arg Asn Gly Asp Thr Thr Arg Leu Ser Pro Leu Asp Val
            340             345             350

Gln Ala Leu Leu Leu Glu Tyr Val Lys Lys Asn Asn Leu Arg Asp Pro
        355             360             365

Gln Gln Gln Ser Gln Ile Asn Cys Asp Leu Arg Leu Thr Asn Leu Phe
    370             375             380

Gly Lys Ser Arg Ile Gly His Phe Glu Met Leu Asn Leu Leu Gln Ser
385             390             395             400

His Val His Ile Lys Gly Thr Thr Ala Asp Asn Ala Thr Ser Ser Gly
            405             410             415

Ala Gly Val Val Ile Asn Pro Val Glu Ser Lys Glu Lys Tyr Asp Cys
            420             425             430

Glu Val Val Asp Asp Cys Glu Arg Lys Arg Lys Thr Arg Lys Lys Ala
            435             440             445

Asp Glu Ser Arg Gln Gln Leu His Ala Ile Val Asp Glu Tyr Ala Ala
        450             455             460

Ile Asp Ile Gln Asn Ile Asn Leu Ile Tyr Leu Arg Arg Asp Leu Ile
465             470             475             480

Val Ser Leu Ile Asp Asp Glu Lys Phe Asn Asp Met Val Ile Gly Ser
            485             490             495

Ile Val Arg Ile Gln Ile Pro Asn Asn Asp Glu Lys His Asp Phe His
            500             505             510

Arg Leu Val Gln Val Val Gly Ile Ser Lys Ile Ser Thr Pro Tyr Thr
        515             520             525

Val Gly Glu Lys Thr Ile Asp Val Met Leu Asp Ile Leu Asn Leu Asp
    530             535             540

Lys Arg Glu Ser Val Ser Val Gln Gly Ile Ser Asn Gln Glu Phe Thr
545             550             555             560

Glu Glu Glu Cys Arg Arg Leu Arg Arg Ser Ile Lys Cys Gly Leu Val
            565             570             575

Lys Arg Phe Arg Val Ser Glu Ile Leu Asp Lys Gly Arg Glu Leu Gln
            580             585             590

Ala Leu Lys Ile Lys Asp Leu Leu Gln Lys Glu Ile Ser Gln Leu Thr
        595             600             605

His Leu His Asp Gln Ala Ser Glu Lys Gly Asn Val Asp Glu Leu Arg
    610             615             620
```

```
Tyr Phe Ala Glu Arg Leu His Arg Leu Lys Ser Pro Glu Glu Cys Gln
625                 630                 635                 640

Arg Arg Leu Leu Glu Ile Leu Glu Val Arg Ser Asp Pro Thr Met Asp
                    645                 650                 655

Pro Ser Tyr Glu Ser Glu Glu Asp Lys Asp Glu Ser Asn Lys Lys Arg
                660                 665                 670

Gln Gly Ser Leu Lys Arg Ser Arg Asn Tyr Asp Phe Asp Glu Lys Glu
            675                 680                 685

Val Glu Leu Thr Ser Pro Arg Arg Gly Thr Asn Ser Asn Val Ser Gly
    690                 695                 700

Ser Asp Val Gln Gln Asn Ser Thr Ser Thr Ser Glu Gln Ser Arg Asn
705                 710                 715                 720

Ile Ser Leu Leu Ala His Glu Asn Lys Glu Gly Asp Cys Leu Ala Ser
                725                 730                 735

Asp Arg Thr Gly Glu Thr Ser Trp Ala Gly Arg Gly Leu Val Pro Asn
                740                 745                 750

Asn Trp Asn Val Pro Ser Gln Ala Lys Thr Ala Thr Pro Leu Ser Ser
            755                 760                 765

Asp Gly Asn Tyr Gln Val Val Leu Pro Glu Ala Ser Ile Pro Pro Leu
    770                 775                 780

Ser Ile Gly Leu Gly Thr Ser Ser Asn Asp Ala Glu Val Glu Arg Ile
785                 790                 795                 800

Trp Gln Tyr Gln Asp Pro Thr Gly Lys Val Gln Gly Pro Phe Ser Met
                805                 810                 815

Thr Gln Leu Arg Asn Trp Asn Asn Ser Gly His Phe Thr Ser Asp Leu
                820                 825                 830

Arg Val Trp Arg Ile Thr Glu Ser Gln Asn Asp Ala Val Leu Leu Thr
                835                 840                 845

Asn Ala Leu Asn Gly Cys Tyr Thr Lys Ala Ser Ser Ile Trp His Asn
    850                 855                 860

Ser His Ile Leu Ser Leu Gly Arg Gly Asn Gly Leu Ser Leu Gly Gly
865                 870                 875                 880

Ser Asp Asn His His Asn Gly Gln Ser Asn Gly Gly Thr Asp Ser Gly
                885                 890                 895

Thr Asn Leu Ile Arg Phe Gly Val Asp Pro Ile Arg Asn Ser Asn Ser
                900                 905                 910

Glu Gln Lys Asp His Ile Ala Val Cys Asp Ala Glu Asn Glu Pro Met
            915                 920                 925

Met Ser Thr Gly Ser Ser Ser Pro Ser Lys Asp Leu Cys Ala Pro Ala
    930                 935                 940

Asp Thr Val Asn Ser Ile Gln Ser Pro Ala Arg Asn Leu Glu Val Ala
945                 950                 955                 960

His Glu Ser Leu Lys Asn Asn Asn Ser Trp Ser Tyr Pro Ser Leu Met
                965                 970                 975

Asn Leu Leu Ser Ser Ala Thr Leu Ser Leu Gln Pro Pro Val Thr Glu
                980                 985                 990

Val His Gln Ala Lys Glu Asn His  Ser Pro Asn Asn Glu  Asp Gln Asn
            995                 1000                1005

Ser Gln  Thr Ile Thr Leu Gly  Gly Ile His Ser Gln  Thr Gly Arg
    1010                1015                1020

Lys Lys  Arg Ser Ser Ser Glu  Asp Cys Ser Ser Gln  Ser Ser Gly
    1025                1030                1035

Gln Asn  Trp Ile Ala Pro Pro  Ala Thr Asp Thr Ser  Ser Arg Glu
```

-continued

```
            1040                 1045                 1050

Trp Asn  Ser Asn Cys Ser Gly  Leu Ser Leu Met Asp  Ser Phe Lys
    1055                 1060                 1065

Pro Ser  Glu Lys Ile Gly Glu  Ile Leu Pro Asp Ile  Pro His Ser
    1070                 1075                 1080

Thr Leu  Lys Pro Val Thr Ala  Asp Ala Glu Ile Lys  Gln Ser Ala
    1085                 1090                 1095

Ser Ser  Ser Val Leu Val Gln  Asn Ser Gly Leu Ser  Trp Ser Ser
    1100                 1105                 1110

Ala Ser  Ser Leu Pro Gly Gly  Arg Gln Leu Pro Ser  His Val Ala
    1115                 1120                 1125

Ala Gly  Ala Trp Gly Gly Gly  Tyr Leu Ala Ala Pro  Gly Arg Ala
    1130                 1135                 1140

Ile Glu  Asp Leu Asn Ser Ser  Phe Ile Thr Ala Ser  Gly Met Lys
    1145                 1150                 1155

Ser Ser  Asp Ile Ile Asp Asp  His Glu Thr Thr Gly  Ala Thr Ile
    1160                 1165                 1170

Asn Trp  Ile Asp Asp Glu Pro  Asn Asp Phe Asn Ser  Leu Val Asp
    1175                 1180                 1185

Glu Ser  Val Ser Asp Leu Leu  Ala Glu Val Glu Ala  Met Glu Cys
    1190                 1195                 1200

Leu Ser  Gly Leu Ala Ser Thr  Ala Ser Met Met Asn  Cys Asn Glu
    1205                 1210                 1215

Gly Leu  Thr Arg Asp Ser Arg  Ser Asp Cys Phe Phe  Ser Val Asp
    1220                 1225                 1230

Gly Phe  Asn Pro Ala Ala Glu  Met Gly Lys Val Asp  Ala Leu Ser
    1235                 1240                 1245

Ser Thr  Ala Asn Leu Gln Phe  Pro Phe Asn Ile Lys  Val Lys Asp
    1250                 1255                 1260

Glu Gln  Pro
    1265
```

<210> SEQ ID NO 14
<211> LENGTH: 1266
<212> TYPE: PRT
<213> ORGANISM: Citrullus lanatus

<400> SEQUENCE: 14

```
Met Asp Lys Pro Leu Asp Pro Pro Leu Asp Phe Tyr Lys Pro Arg Leu
1               5                   10                  15

Gln Pro Asp Asp Pro Thr Pro Pro Pro Asp Ala Ser Val Leu Gly
            20                  25                  30

Asn Ser His His Pro Pro His Leu Met Asp Ser His Ile Asp Asp Ser
        35                  40                  45

Lys Leu Val Gly Val Pro Val Ala Gly Pro Leu Leu Pro Ala Asp Ser
    50                  55                  60

Ser Pro Ala Ala Lys Leu Asn Ala Lys Phe Lys Asp Lys Val Leu Val
65                  70                  75                  80

Val Asp Lys Thr Leu Gly Ile Arg Arg Arg Gly Arg Pro Pro Arg Gly
                85                  90                  95

Gln Val Lys Pro Pro Pro Leu Pro Pro Arg Gln Lys Lys Asp Glu Glu
            100                 105                 110

Asp Val Cys Phe Ile Cys Phe Asp Gly Gly Ser Leu Val Leu Cys Asp
            115                 120                 125
```

```
Arg Arg Gly Cys Pro Lys Ala Tyr His Pro Ser Cys Ile Lys Arg Asp
130             135             140

Glu Ser Phe Phe Arg Ser Lys Ala Lys Trp Asn Cys Gly Trp His Ile
145             150             155             160

Cys Thr Asn Cys Gln Lys Ala Ser Tyr Tyr Met Cys Tyr Thr Cys Pro
                165             170             175

Phe Ser Leu Cys Lys Gly Cys Ile Lys Gly Ala Asp Tyr Gln Cys Val
            180             185             190

Arg Gly Thr Lys Gly Phe Cys Gly Thr Cys Met Lys Ile Ile Met Leu
            195             200             205

Phe Glu Lys Ser Ala Pro Asp Gly Glu Ser Val Gln Val Asp Phe Asp
    210             215             220

Asp Lys Ser Ser Trp Glu Tyr Leu Phe Lys Val Tyr Trp Ile Tyr Leu
225             230             235             240

Lys Glu Lys Leu Ser Leu Thr Val Asp Glu Leu Val Arg Ala Lys Asn
            245             250             255

Ser Trp Lys Gly Ser Ile Ile Met Asp His Lys Val Ala Ser Ser Glu
            260             265             270

Ile Leu Asp Gly Ser Ile Asp Lys Ser Gln Gly Ala His Asn Ser Phe
    275             280             285

Arg Asn Pro Lys Ser Gln Arg Lys Arg Pro Asn Arg Gln Gln Ser Ser
    290             295             300

Leu Asn Lys Phe Gly Ser Leu Val Asp Arg Pro Ser Ser Asn Glu Gln
305             310             315             320

Phe Ser Val Ser Thr Lys Trp Thr Thr Thr Glu Leu Met Asp Phe Val
            325             330             335

Ala His Val Arg Asn Gly Asp Thr Thr Arg Leu Ser Pro Leu Asp Val
            340             345             350

Gln Ala Leu Leu Leu Glu Tyr Val Lys Lys Asn Asn Leu Arg Asp Pro
    355             360             365

Gln Gln Gln Ser Gln Ile Asn Cys Asp Leu Arg Leu Thr Asn Leu Phe
    370             375             380

Gly Lys Ser Arg Ile Gly His Phe Glu Met Leu Asn Leu Leu Gln Ser
385             390             395             400

His Val His Ile Lys Gly Thr Thr Ala Asp Asn Ala Thr Ser Ser Gly
            405             410             415

Ala Gly Val Val Ile Asn Pro Val Glu Ser Lys Glu Lys Tyr Asp Cys
            420             425             430

Glu Val Val Asp Asp Cys Glu Arg Lys Arg Lys Thr Arg Lys Lys Ala
            435             440             445

Asp Glu Ser Arg Gln Gln Leu His Ala Ile Val Asp Glu Tyr Ala Ala
    450             455             460

Ile Asp Ile Gln Asn Ile Asn Leu Ile Tyr Leu Arg Arg Asp Leu Ile
465             470             475             480

Val Ser Leu Ile Asp Asp Glu Lys Phe Asn Asp Met Val Ile Gly Ser
            485             490             495

Ile Val Arg Ile Gln Ile Pro Asn Asn Asp Glu Lys His Asp Phe His
            500             505             510

Arg Leu Val Gln Val Val Gly Ile Ser Lys Ile Ser Thr Pro Tyr Thr
            515             520             525

Val Gly Glu Lys Thr Ile Asp Val Met Leu Asp Ile Leu Asn Leu Asp
    530             535             540

Lys Arg Glu Ser Val Ser Val Gln Gly Ile Ser Asn Gln Glu Phe Thr
```

-continued

```
545            550            555            560

Glu Glu Glu Cys Arg Arg Leu Arg Arg Ser Ile Lys Cys Gly Leu Val
                565            570            575

Lys Arg Phe Arg Val Ser Glu Ile Leu Asp Lys Gly Arg Glu Leu Gln
                580            585            590

Ala Leu Lys Ile Lys Asp Leu Leu Gln Lys Glu Ile Ser Gln Leu Thr
                595            600            605

His Leu His Asp Gln Ala Ser Glu Lys Gly Asn Val Asp Glu Leu Arg
            610            615            620

Tyr Phe Ala Glu Arg Leu His Arg Leu Lys Ser Pro Glu Glu Cys Gln
625            630            635            640

Arg Arg Leu Leu Glu Ile Leu Glu Val Arg Ser Asp Pro Thr Met Asp
                645            650            655

Pro Ser Tyr Glu Ser Glu Glu Asp Lys Asp Glu Ser Asn Lys Lys Arg
                660            665            670

Gln Gly Ser Leu Lys Arg Ser Arg Asn Tyr Asp Phe Asp Glu Lys Glu
                675            680            685

Val Glu Leu Thr Ser Pro Arg Arg Gly Thr Asn Ser Asn Val Ser Gly
            690            695            700

Ser Asp Val Gln Gln Asn Ser Thr Ser Thr Ser Glu Gln Ser Arg Asn
705            710            715            720

Ile Ser Leu Leu Ala His Glu Asn Lys Glu Gly Asp Cys Leu Ala Ser
                725            730            735

Asp Arg Thr Gly Glu Thr Ser Trp Ala Gly Arg Gly Leu Val Pro Asn
                740            745            750

Asn Trp Asn Val Pro Ser Gln Ala Lys Thr Ala Thr Pro Leu Ser Ser
                755            760            765

Asp Gly Asn Tyr Gln Val Val Leu Pro Glu Ala Ser Ile Pro Pro Leu
            770            775            780

Ser Ile Gly Leu Gly Thr Ser Ser Asn Asp Ala Glu Val Glu Arg Ile
785            790            795            800

Trp Gln Tyr Gln Asp Pro Thr Gly Lys Val Gln Gly Pro Phe Ser Met
                805            810            815

Thr Gln Leu Arg Asn Trp Asn Asn Ser Gly His Phe Thr Pro Asp Leu
                820            825            830

Arg Val Trp Arg Ile Thr Glu Ser Gln Asn Asp Ala Val Leu Leu Thr
                835            840            845

Asn Ala Leu Asn Gly Cys Tyr Thr Lys Ala Ser Ser Ile Trp His Asn
            850            855            860

Ser His Ile Leu Ser Leu Gly Arg Gly Asn Gly Leu Ser Leu Gly Gly
865            870            875            880

Ser Asp Asn His His Asn Gly Gln Ser Asn Gly Gly Thr Asp Ser Gly
                885            890            895

Thr Asn Leu Ile Arg Phe Gly Val Asp Pro Ile Arg Asn Ser Asn Ser
            900            905            910

Glu Gln Lys Asp His Ile Ala Val Cys Asp Ala Glu Asn Glu Pro Met
            915            920            925

Met Ser Thr Gly Ser Ser Ser Pro Ser Lys Asp Leu Cys Ala Pro Ala
            930            935            940

Asp Thr Val Asn Ser Ile Gln Ser Pro Ala Arg Asn Leu Glu Val Ala
945            950            955            960

His Glu Ser Leu Lys Asn Asn Asn Ser Trp Ser Tyr Pro Ser Leu Met
                965            970            975
```

-continued

```
Asn Leu Leu Ser Ser Ala Thr Leu Ser Leu Gln Pro Pro Val Thr Glu
            980                 985                 990

Val His Gln Ala Lys Glu Asn His  Ser Pro Asn Asn Glu  Asp Gln Asn
        995                 1000                 1005

Ser Gln  Thr Ile Thr Leu Gly  Gly Ile His Ser Gln  Thr Gly Arg
    1010                 1015                 1020

Lys Lys  Arg Ser Ser Ser Glu  Asp Cys Ser Ser Gln  Ser Ser Gly
    1025                 1030                 1035

Gln Asn  Trp Ile Ala Pro Pro  Ala Thr Asp Thr Ser  Ser Arg Glu
    1040                 1045                 1050

Trp Asn  Ser Asn Cys Ser Gly  Leu Ser Leu Met Asp  Ser Phe Lys
    1055                 1060                 1065

Pro Ser  Glu Lys Ile Gly Glu  Ile Leu Pro Asp Ile  Pro His Ser
    1070                 1075                 1080

Thr Leu  Lys Pro Val Thr Ala  Asp Ala Glu Ile Lys  Gln Ser Ala
    1085                 1090                 1095

Ser Ser  Ser Val Leu Val Gln  Asn Ser Gly Leu Ser  Trp Ser Ser
    1100                 1105                 1110

Ala Ser  Ser Leu Pro Gly Gly  Arg Gln Leu Pro Ser  His Val Ala
    1115                 1120                 1125

Ala Gly  Ala Trp Gly Gly Gly  Tyr Leu Ala Ala Pro  Gly Arg Ala
    1130                 1135                 1140

Ile Glu  Asp Leu Asn Ser Ser  Phe Ile Thr Ala Ser  Gly Met Lys
    1145                 1150                 1155

Ser Ser  Asp Ile Ile Asp Asp  His Glu Thr Thr Gly  Ala Thr Ile
    1160                 1165                 1170

Asn Trp  Ile Asp Asp Glu Pro  Asn Asp Phe Asn Ser  Leu Val Asp
    1175                 1180                 1185

Glu Ser  Val Ser Asp Leu Leu  Ala Glu Val Glu Ala  Met Glu Cys
    1190                 1195                 1200

Leu Ser  Gly Leu Ala Ser Thr  Ala Ser Met Met Asn  Cys Asn Glu
    1205                 1210                 1215

Gly Leu  Thr Arg Asp Ser Arg  Ser Asp Cys Phe Phe  Ser Val Asp
    1220                 1225                 1230

Gly Phe  Asn Pro Ala Ala Glu  Met Gly Lys Val Asp  Ala Leu Ser
    1235                 1240                 1245

Ser Thr  Ala Asn Leu Gln Phe  Pro Phe Asn Ile Lys  Val Lys Asp
    1250                 1255                 1260

Glu Gln  Pro
    1265
```